(12) United States Patent
Dulay et al.

(10) Patent No.: US 9,129,785 B2
(45) Date of Patent: Sep. 8, 2015

(54) METAL ORGANIC POLYMER MATRICES AND SYSTEMS FOR CHEMICAL AND BIOCHEMICAL MASS SPECTROMETRY AND METHODS OF USE THEREOF

(71) Applicant: The Board of Trustees of the Leland Stanford Junior University, Palo Alto, CA (US)

(72) Inventors: Maria T. Dulay, Sunnyvale, CA (US); Richard N. Zare, Stanford, CA (US); Livia Schiavinato Eberlin, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/448,329

(22) Filed: Jul. 31, 2014

(65) Prior Publication Data

US 2015/0037828 A1    Feb. 5, 2015

Related U.S. Application Data

(60) Provisional application No. 61/861,234, filed on Aug. 1, 2013, provisional application No. 61/919,495, filed on Dec. 20, 2013.

(51) Int. Cl.
*H01J 49/04*    (2006.01)
*H01J 49/00*    (2006.01)
*H01J 49/16*    (2006.01)

(52) U.S. Cl.
CPC ......... *H01J 49/0409* (2013.01); *H01J 49/0031* (2013.01); *H01J 49/16* (2013.01)

(58) Field of Classification Search
USPC ....................................................... 250/288
See application file for complete search history.

(56) References Cited

U.S. PATENT DOCUMENTS 6,288,390 B1 *  9/2001  Siuzdak et al. ............... 250/288
6,866,785 B2    3/2005  Zare et al.
(Continued)

FOREIGN PATENT DOCUMENTS

EP    1507574 B1    5/2009
EP    1418997 B1    4/2010
(Continued)

OTHER PUBLICATIONS

Dulay, et al. "Photopolymerized Sol-Gel Monoliths for Capillary Electrochromatography", Anal. Chem. 2001, 73, 3921-3926.
(Continued)

*Primary Examiner* — Kiet T Nguyen
(74) *Attorney, Agent, or Firm* — Khin K. Chin; Bret E. Field; Bozicevic, Field & Francis LLP

(57) ABSTRACT

Aspects of the disclosure include methods for analyzing an analyte composition by mass spectrometry employing a macroporous metal organic polymer matrix. In practicing methods according to certain embodiments an analyte composition is applied to a macroporous metal organic polymer matrix, a voltage is applied to the macroporous metal organic polymer matrix sufficient to produce and expel analyte ions from the macroporous metal organic polymer matrix and the analyte ions are analyzed by mass spectrometry. In other embodiments, a composition having biological macromolecules is applied onto a surface-modified macroporous metal organic polymer matrix and analytes produced by reaction (e.g., enzymatic cleavage of the biological macromolecules) at or near the surface of the macroporous metal organic polymer matrix are measured by mass spectrometry. Mass spectrometry emitters made from the subject macroporous metal organic polymer matrix, mass spectrometry systems employing macroporous metal organic polymer matrices of interest and kits suitable for practicing the subject methods are also described.

19 Claims, 35 Drawing Sheets

(56) References Cited

U.S. PATENT DOCUMENTS

| | | |
|---|---|---|
| 6,875,348 B2 | 4/2005 | Zare et al. |
| 6,884,346 B2 | 4/2005 | Zare et al. |
| 6,924,478 B1 | 8/2005 | Zubarev et al. |
| 6,986,841 B2 | 1/2006 | Zare et al. |
| 7,145,133 B2 | 12/2006 | Thomson |
| 7,229,834 B2 | 6/2007 | Chace |
| 7,507,953 B2 | 3/2009 | Makarov et al. |
| 7,531,793 B2 | 5/2009 | Satoh et al. |
| 7,534,996 B2 | 5/2009 | Suits et al. |
| 2007/0023627 A1* | 2/2007 | Finch et al. .................. 250/282 |
| 2007/0284308 A1 | 12/2007 | Zare et al. |
| 2008/0128608 A1* | 6/2008 | Northen et al. ............... 250/282 |
| 2013/0112866 A1 | 5/2013 | Ouyang et al. |

FOREIGN PATENT DOCUMENTS

| | | |
|---|---|---|
| WO | 2012125552 A2 | 9/2012 |
| WO | 2012167126 A1 | 12/2012 |

OTHER PUBLICATIONS

Hench, et al. "The Sol-Gel Process", Chem. Rev. 1990, 90, 33-72.

Huang, et al. "Ambient Ionization Mass Spectrometry", Annu. Rev. Anal. Chem. 2010. 3:43-65.

Schottner, Gerhard. "Hybrid Sol-Gel-Derived Polymers: Applications of Multifunctional Materials", Chem. Mater. 2001, 13, 3422-3435.

Wang, et al. "Paper Spray for Direct Analysis of Complex Mixtures Using Mass Spectrometry", Angew. Chem. Int. Ed. 2010, 49, 877-880.

Yang, et al. "Paper spray ionization devices for direct, biomedical analysis using mass spectrometry", International Journal of Mass Spectrometry 312 (2012) 201-207.

Zhang, et al. "Silica Coated Paper Substrate for Paper-Spray Analysis of Therapeutic Drugs in Dried Blood Spots", Anal. Chem. 2012, 84, 931-938.

* cited by examiner

Top View

Side View

Inlet of heated capillary at MS nozzle

OSX material (triangle shape)

METAL ORGANIC POLYMER MATRICES AND SYSTEMS FOR CHEMICAL AND BIOCHEMICAL MASS SPECTROMETRY AND METHODS OF USE THEREOF

CROSS-REFERENCE TO RELATED APPLICATIONS

Pursuant to 35 U.S.C. §119 (e), this application claims priority to the filing date of U.S. Provisional Patent Application Ser. No. 61/861,234 filed on Aug. 1, 2013 and U.S. Provisional Patent Application Ser. No. 61/919,495, filed on Dec. 20, 2014; the disclosure of which applications are herein incorporated by reference.

INTRODUCTION

Mass spectrometry is a sensitive method for the analysis of compounds that has been used in the quantitative and qualitative analysis of compounds in areas of study ranging from chemistry to agriculture, medicine, toxicology, biology and homeland security. For example, mass spectrometry is a technique employed to analyze components of complex mixtures in therapeutic drug monitoring, pharmaceutical drug discovery, drug screenings, toxic, hazardous, explosive and other dangerous materials detection systems, forensic and clinical toxicology, genomics and proteomics among many other mass spectrometry applications.

There is a constant need for the development of simplified and miniaturized complex mixture analysis methods and devices requiring lower quantities of analyte composition and more efficient ways to obtain isolated and purified analytical samples.

SUMMARY

Aspects of the invention include methods for analyzing an analyte composition by mass spectrometry employing a macroporous metal organic polymer matrix. In practicing methods according to certain embodiments an analyte composition is applied to a macroporous metal organic polymer matrix, a voltage is applied to the macroporous metal organic polymer matrix sufficient to produce and expel analyte ions from the macroporous metal organic polymer matrix and the analyte ions are analyzed by mass spectrometry. In other embodiments, a composition having biological macromolecules is applied onto a surface-modified macroporous metal organic polymer matrix and analytes produced by reaction (e.g., enzymatic cleavage of the biological macromolecules) at or near the surface of the macroporous metal organic polymer matrix are measured by mass spectrometry. Mass spectrometry emitters made from the subject macroporous metal organic polymer matrix, mass spectrometry systems employing macroporous metal organic polymer matrices of interest and kits suitable for practicing the subject methods are also described.

In embodiments of the present invention, an analyte composition is applied to the macroporous metal organic polymer matrix. In some instances, the analyte composition is dissolved in a solvent and then applied to the macroporous metal organic polymer matrix. In other instances, the analyte composition is applied to the macroporous metal organic polymer matrix without solvent. The analyte composition may be applied to the macroporous metal organic polymer matrix in discrete Fs or may be continuously applied for a predetermined period of time.

In some embodiments, the components of the analyte composition are separated prior to analysis. In some instances, the components of the analyte composition are separated using the macroporous metal organic polymer matrix in electrokinetic separation protocols, as a chromatography substrate (e.g., a reverse phase chromatography substrate, an affinity chromatography substrate, a size-exclusion chromatography substrate, etc.), as a filtration material (e.g., a size exclusion filter or an affinity filter such as when the macroporous metal organic polymer matrix includes binding or recognition components) and the like. For example, the components of the analyte composition may be separated (e.g., by an electrokinetic protocol) along an axis orthogonal to the axis for producing and expelling analyte ions from the macroporous metal organic polymer matrix. In other instances, the components of the analyte composition are separated along the same axis used to produce and expel analyte ions from the macroporous metal organic polymer matrix. In certain instances, separation of the components of the analyte composition prior to analysis includes a multi-step separation protocol where the analyte composition is separated with a first separation protocol (e.g., liquid chromatography, capillary electrophoresis) and then further separated using the macroporous metal organic polymer matrix as a second separation protocol.

In certain embodiments, methods also include analyzing an analyte composition produced in situ within the pores of the macroporous metal organic polymer matrix by: 1) a chemical reaction performed on the surface or within the pores of the macroporous metal organic polymer matrix; 2) a biochemical reaction performed on the surface or within the pores of the macroporous metal organic polymer matrix; 3) whole cells on the surface or within the pores of the macroporous metal organic polymer matrix; or 4) microorganisms on the surface or within the pores of the macroporous metal organic polymer matrix.

In certain instances, macroporous metal organic polymer matrices of interest include one or more enzymes covalently bonded to the macroporous metal organic polymer matrix at or near the surface. Where macroporous metal organic polymer matrices include one or more surface bound enzymes, methods may further include contacting the surface of the macroporous metal organic polymer matrix with an analyte composition having one or more biological macromolecules, such as proteins, enzymes, antibodies or other peptide-containing macromolecule and maintaining the analyte composition in contact with the macroporous metal organic polymer matrix in a manner sufficient to enzymatically cleave the biological macromolecule into fragments. In these embodiments, the cleavage fragments may be analyzed by mass spectrometry.

Embodiments of the invention according to certain embodiments include ionization of analytes in the analyte composition by applying a voltage to the macroporous metal organic polymer matrix sufficient to produce and expel the analyte ions from the macroporous metal organic polymer matrix. In other embodiments, ionization of analytes includes surface desorption ionization (e.g., desorption electrospray ionization) to produce and expel analyte ions at or near the surface of the macroporous metal organic polymer matrix. Ionization of the analytes may be ambient ionization or in an environment having a reduced pressure atmosphere.

Analyte ions are subsequently analyzed to determine the chemical make-up of the analyte composition. In certain embodiments, the analyte ions are analyzed by a mass spectrometer.

Aspects of the present invention also include macroporous metal organic polymer matrices suitable for practicing the subject methods. Macroporous metal organic polymer matrices according to certain embodiments are castable, sol-gel compositions prepared from metal alkoxide precursors. In some embodiments, macroporous metal organic polymer matrix precursors have the formula:

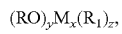

where x is an integer from 1 to 4;
y is an integer from 0 to 4;
z is an integer from 0 to 4;
where at least one of y or z is 1 or greater;
M is aluminum, barium, antimony, calcium, chromium, copper, erbium, germanium, iron, lead, lithium, phosphorus, potassium, silicon, tantalum, tin, titanium, vanadium, zinc, zirconium or combinations thereof;
R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
$R_1$ is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl.

In certain embodiments, the macroporous metal organic polymer matrix is an organosiloxane polymer matrix. Where the macroporous metal organic polymer matrix is an organosiloxane polymer matrix, precursors may include, but are not limited to methyltrimethoxysilane, dimethyldimethoxysilane, tetraethoxysilane, methacryloxypropyltrimethoxysilane, bis(triethoxysilyl)ethane, bis(triethoxysilyl)butane, bis(triethoxysilyl)pentane, bis(triethoxysilyl)hexane, bis(triethoxysilyl)heptane and bis(triethoxysilyl)octane.

Subject macroporous metal organic polymer matrices may be functionalized with one or more functional groups, such as for example but not limited to alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl, aldehyde, amine, substituted amine, amide, substituted amide, alkoxy, substituted alkoxy, carboxylic acid, substituted carboxylic acid, ester, substituted ester, ether, hydroxyl, imine, isocyanate, and thionyl. In certain embodiments, the subject macroporous metal organic polymer matrix is functionalized at discrete locations on the surface of the macroporous metal organic polymer matrix. Each discrete location may include the same or different functional groups, as desired.

In embodiments, the subject macroporous metal organic polymer matrix may also include a biologically active compound such as peptides, proteins, polysaccharides, oligonucleotides, enzymes, antibodies, cellular components (including cell membranes, organelles, etc.), whole cells, microorganisms (e.g., bacteria), organic polymers (e.g., polyalkylene oxides, including polyethylene glycol), luminescent compounds (such as fluorophores, phosphores, among others) and combinations thereof. Where macroporous metal organic polymer matrices include a biologically active compound, these compounds may be physically associated (e.g., encapsulated) or covalently bound within the pores of the macroporous metal organic polymer matrix. In some embodiments, the biologically active compounds are covalently bonded through one or more functional groups at the surface of the macroporous metal organic polymer matrix and are configured to catalyze a reaction on the surface of the macroporous metal organic polymer matrix. In certain instances, one or more different protease enzymes are covalently bonded at or near the surface of the macroporous metal organic polymer matrix and are configured for proteolysis of proteins (including glycoproteins), enzymes, antibodies or other peptide-containing macromolecules applied to the surface of the macroporous metal organic polymer matrix. The covalently bonded biologically active compounds may cover all or part of the macroporous metal organic polymer matrix surface or be positioned at discrete locations, such as in an array configuration. Where biologically active compounds are covalently bonded at or near the surface of the macroporous metal organic polymer matrix at discrete locations, each discrete location may include the same or different biologically active compound. In these embodiments, analyte compositions are may be applied to the surface of the biologically active compound-bonded macroporous metal organic polymer matrix as a fluidic sample (e.g., urine, blood, plasma, serum, saliva, etc.) or as a solid sample (e.g., tissue). Macroporous metal organic polymer matrices of interest may be porous and can be planar or take a three-dimensional shape. For example, the macroporous metal organic polymer matrix may be conical, triangular, in the shape of a half circle, square, rectangle or other suitable shape as desired. Depending on the shape of the matrix, the macroporous metal organic polymer matrix may have one or more vertices. In certain embodiments, the subject macroporous metal organic polymer matrix is cast on a substrate, such as a glass or plastic substrate. In some embodiments, the macroporous metal organic polymer matrix is flexible. In certain embodiments, the macroporous metal organic polymer matrix is reusable.

In some embodiments, the macroporous metal organic polymer matrix is configured for separating one or more components of an analyte composition. The macroporous metal organic polymer matrix may be configured to be a filtration material (e.g., a size exclusion filter or an affinity filter such as when the macroporous metal organic polymer matrix includes binding or recognition components), a chromatography material (e.g., a reverse phase chromatography substrate, an affinity chromatography substrate, a size-exclusion chromatography substrate, etc.) or an electrokinetic separation material.

Aspects of the present disclosure also include systems suitable for practicing the subject methods that include one or more of the subject macroporous metal organic polymer matrices and a mass analyzer. In some embodiments, the mass analyzer is a mass spectrometer. In certain embodiments, systems may also include one more sources of solvent, one or more sampling devices for applying the analyte composition to the macroporous metal organic polymer matrix, as well as high throughput and computer controlled systems for practicing methods according to certain embodiments.

DEFINITION OF SELECT CHEMICAL TERMINOLOGY

Figure 1:
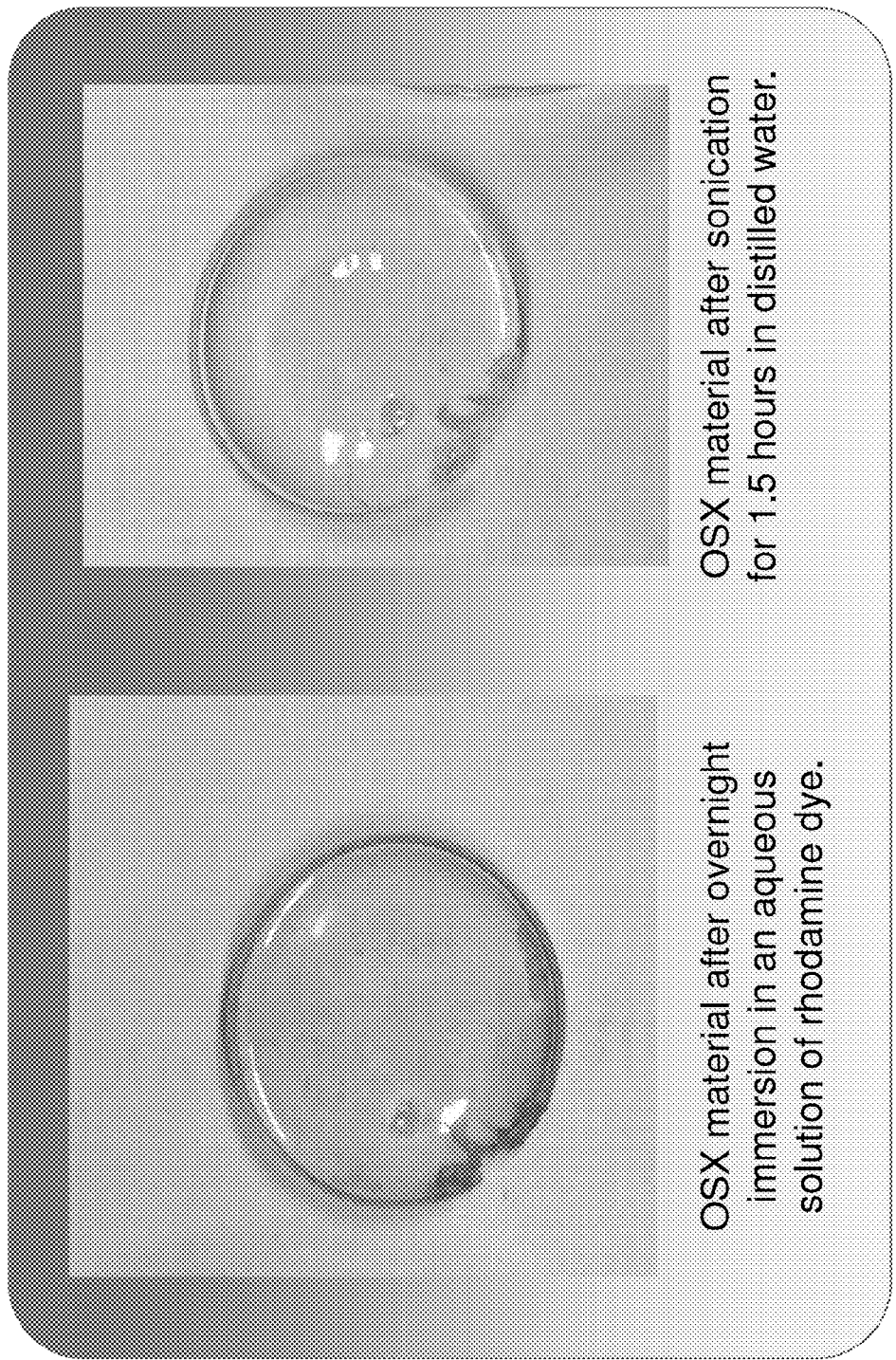
FIG. 1 shows an example of an organosiloxane polymer matrix having absorbed rhodamine dye and the organosiloxane polymer matrix after dye removal from the pores by sonication according to certain embodiments.

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —$C(O)OR^{31}$ where $R^{31}$ represents an alkyl or cycloalkyl group as defined herein.

Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is $(C_3-C_{10})$ cycloalkyl. In certain embodiments, the cycloalkyl group is $(C_3-C_7)$ cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N— NR$^{39}$R$^{40}$, —PR$^{41}$—, P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)O R$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)N R$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$ R$^{60}$, —P(O)(OR$^{60}$)(O$^-$), —OP(O)(OR$^{60}$)(O R$^{61}$), —C(O)R$^{60}$, —C(O)OR$^{60}$, —C(O)NR$^{60}$R$^{61}$, —C(O)O$^-$. In certain embodiments, substituents include -M, —R—OR$^{60}$, =O, —OR$^{60}$, —SR$^{60}$, —NR$^{60}$R$^{61}$, CF$_3$, —CN, —NO$_2$, —S(O)$_2$ R$^{60}$, —OP(O)(OR$^{60}$)(O R$^{61}$), —C(O)OR$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

Aspects of the invention include methods for analyzing an analyte composition by mass spectrometry employing a macroporous metal organic polymer matrix. In practicing methods according to certain embodiments an analyte composition is applied to a macroporous metal organic polymer matrix, a voltage is applied to the macroporous metal organic polymer matrix sufficient to produce and expel analyte ions from the macroporous metal organic polymer matrix and the analyte ions are analyzed by mass spectrometry. In other embodiments, a composition having biological macromolecules is applied onto a surface-modified macroporous metal organic polymer matrix and analytes produced by reaction (e.g., enzymatic cleavage of the biological macromolecules) at the surface of the macroporous metal organic polymer matrix are measured by mass spectrometry. Mass spectrometry emitters made from the subject macroporous metal organic polymer matrix, mass spectrometry systems employing macroporous metal organic polymer matrices of interest and kits suitable for practicing the subject methods are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present disclosure provides methods for analyzing an analyte composition by mass spectrometry employing a macroporous metal organic polymer matrix. In further describing embodiments of the disclosure, methods for analyzing an analyte composition are first described in greater detail. Next macroporous metal organic polymer matrices suitable for practicing the subject methods are next described. Systems and kits including the subject macroporous metal organic polymer matrices are also described.

Methods for Analyzing an Analyte Composition

As summarized above, aspects of the disclosure include methods for analyzing an analyte composition. In practicing the subject methods according to certain embodiments, a voltage is applied to an analyte containing macroporous metal organic polymer matrix sufficient to produce and expel analyte ions from the macroporous metal organic polymer matrix and the analyte ions are characterized by a mass analyzer. In other embodiments, a composition having biological macromolecules is applied onto a modified macroporous metal organic polymer matrix and analytes produced by reaction (e.g., enzymatic cleavage of the biological macromolecules) at or near the surface of the macroporous metal organic polymer matrix are measured by mass spectrometry. In some instances, methods also include applying the analyte composition to the macroporous metal organic polymer matrix to produce the analyte containing macroporous metal organic polymer matrix.

As described in greater detail below, the subject macroporous metal organic polymer matrices include metal organic, or metalorganic, polymers, where the term metal organic, or metalorganic, refers to a material that include an organic ligand attached to a metal atom or a metalloid atom. Macroporous metal organic polymer matrices of the invention are castable, porous sol-gel polymers prepared from metal organic monomeric precursors. A precursor of the macroporous metal organic polymer may be a metal alkoxide or mixture of metal alkoxides, where the term metal alkoxide refers to a metal organic, or metalorganic, material, that has a metal-oxygen-carbon linkage or metalloid-oxygen-carbon linkage. Suitable metals according to certain embodiments include but are not limited to aluminum, barium, antimony, calcium, chromium, copper, erbium, germanium, iron, lead, lithium, phosphorus, potassium, silicon, tantalum, tin, titanium, vanadium, zinc, zirconium or combinations thereof.

In some embodiments, precursors of macroporous metal organic polymer matrices of interest may be of the formula:

where x is an integer from 1 to 4;
y is an integer from 0 to 4;
z is an integer from 0 to 4;
where at least one of y or z is 1 or greater;
M is aluminum, barium, antimony, calcium, chromium, copper, erbium, germanium, iron, lead, lithium, phosphorus, potassium, silicon, tantalum, tin, titanium, vanadium, zinc or zirconium;
R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
$R_1$ is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl.

In certain embodiments, macroporous metal organic polymer matrices of interest are organosiloxane polymer matrices and are prepared from organosiloxane precursors. For example, organosiloxane polymer matrices of interest include polymeric composition prepared from organosiloxane precursors which may include, but are not limited to methyltrimethoxysilane, dimethyldimethoxysilane, tetraethoxysilane, methacryloxypropyltrimethoxysilane, bis(triethoxysilyl)ethane, bis(triethoxysilyl)butane, bis(triethoxysilyl)pentane, bis(triethoxysilyl)hexane, bis(triethoxysilyl)heptane, bis(triethoxysilyl)octane, and combinations thereof.

In embodiments of the invention, analyte compositions may be any composition where analysis is desired and can be characterized by mass analysis. Analyte compositions may be solids or liquids. For example, analyte compositions may include but are not limited to chemicals used in agriculture (e.g., pesticides, fertilizers, pollination enhancers, etc.), pharmaceutical compositions, toxicology specimens, drug screening specimens, chemical and biological weapons and precursor compositions, explosives, among others. In some embodiments, analyte compositions include compounds obtained through chemical synthesis, such as organic, organometallic, inorganic and photochemical synthesis. In other embodiments, analyte compositions include compounds obtained through biochemical reactions (e.g., enzyme catalyzed reaction). In yet other embodiments, analyte compositions include biological macromolecules, such as proteins (including glycoproteins), enzymes, antibodies and other peptide-containing macromolecules. Certain analyte compositions also include compounds produced by cleavage of the biological macromolecules. In still other embodiments, analyte compositions include compounds produced by cells or microorganisms.

In certain embodiments, analyte compositions include biological samples. The term "biological sample" as used herein refers to a material or mixture of materials, typically, although not necessarily, in liquid form, containing one or more analytes of interest. In one instance, the term as used in its broadest sense, refers to any plant, animal or bacterial material, such as for example, tissue or fluid isolated from an individual (including without limitation blood, plasma, serum, cerebrospinal fluid, lymph, tears, saliva, urine, semen, vaginal fluids, amniotic fluid, cord blood, mucus, synovial fluid, and tissue sections) or from in vitro cell culture constituents, as well as samples from the environment. As used herein, the term "a biological sample" can refer to a whole organism or a subset of its tissues, cells or component parts as well as a homogenate, lysate or extract prepared from a whole organism or a subset of its tissues, cells or components therein, or a fraction or portion thereof. In certain embodiments, the sample has been removed from an animal or plant. Biological samples may also include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The analyte composition may be applied to the macroporous metal organic polymer matrix by any convenient protocol. In some embodiments, the analyte composition is applied to the surface of the macroporous metal organic polymer matrix. For example, the analyte composition may be applied to the surface of the macroporous metal organic polymer matrix in the form of a droplet, such as when dispensed using a syringe, dropper or pipet. In another example, the analyte composition is sprayed onto the surface of the macroporous metal organic polymer matrix. In yet other example, the analyte composition may be printed onto the surface of the macroporous metal organic polymer matrix. In still other examples, the analyte composition may be a solid (e.g., tissue section) and may be laid onto the surface of the macroporous metal organic polymer matrix. Where the analyte composition is applied to the surface of the macroporous metal organic polymer matrix, in certain instances, the analyte composition subsequently diffuses into the interior pores of the macroporous metal organic polymer matrix. In other instances, a composition may be contacted with the surface of the macroporous metal organic polymer matrix and analytes of interest are those produced by reaction at or near the surface of the macroporous metal organic polymer matrix. For example, analytes produced by reaction at or near the surface of the macroporous metal organic polymer matrix may include compounds produced by enzymatic cleavage of biological macromolecules (e.g., peptide fragments) by surface bound enzymes.

In other embodiments, applying the analyte composition to the macroporous metal organic polymer matrix includes injecting the composition directly into the interior space of the macroporous metal organic polymer matrix, such as by using a syringe with an attached needle or connecting the macroporous metal organic polymer matrix to a conduit in fluid communication with a source of the analyte composition. In certain embodiments the source of analyte composition connected to the macroporous metal organic polymer matrix is a separation system such as a liquid chromatography or capillary electrophoresis system.

In embodiments, the analyte composition can be applied to the macroporous metal organic polymer matrix as a neat sample or may further include one or more solvents. Where the analyte composition includes one or more solvents, the analyte composition may be first applied as a neat sample and then dissolved in a solvent on the macroporous metal organic polymer matrix. Alternatively, the analyte composition may be dissolved in a solvent prior to applying to the macroporous metal organic polymer matrix. Where the analyte composition is a solid, such as a tissue sample, the analyte composition may be initially processed (e.g., mechanically grinded) or may be applied without modification.

Depending on the analysis protocol desired, application of the analyte composition to the macroporous metal organic polymer matrix may be discrete or continuous. For example, application of the analyte composition to the macroporous metal organic polymer matrix may be completed before analyte ionization (e.g., surface desorption ionization or by applying a voltage to the macroporous metal organic polymer matrix) and analyzing the analyte ions. Alternatively, the analyte composition may be continuously applied (e.g., such as by a syringe pump) to the macroporous metal organic polymer matrix while during analyte ionization (e.g., applying the voltage) as well as during analysis of the analyte ions by mass spectrometry.

All or part of the analyte composition may be applied prior to ionization of analytes of interest. For example, 10% or more of the analyte sample may be applied to the macroporous metal organic polymer matrix before analyte ionization, such as 20% or more, such as 30% or more, such as 40% or more, such as 50% or more, such as 60% or more, such as 70% or more, such as 80% or more and including applying 90% or more of the analyte composition to the macroporous metal organic polymer matrix before analyte ionization. In certain embodiments, the entire (i.e., 100%) analyte composition of interest is applied to the macroporous metal organic polymer matrix before ionization of analytes from the macroporous metal organic polymer matrix. Where analytes are ionized by applying a voltage to the macroporous metal organic polymer matrix, the voltage in certain instances, is applied to the macroporous metal organic polymer matrix concurrently while the analyte composition is applied.

The amount of analyte composition applied to the subject macroporous metal organic polymer matrix may vary depending on the type of sample, concentration of analytes and method of application (e.g., discrete or continuous). For example, where a discrete amount of analyte composition is applied to the macroporous metal organic polymer matrix, the amount applied may range from 0.001 µg to 100 µg, such as 0.005 µg to 95 µg, such as 0.01 µg to 90 µg, such as 0.05 µg to 85 µg, such as 0.1 µg to 80 µg, such as 0.5 µg to 75 µg, such as 1 µg to 70 µg, and including applying between 5 µg to 50 µg of the analyte composition to the macroporous metal organic polymer matrix. Alternatively, where the analyte composition is continuously applied to the macroporous metal organic polymer matrix, the amount of analyte composition which is applied may be 0.01 mL or greater, such as 0.05 mL or greater, such as 0.1 mL or greater, such as 0.5 mL or greater, such as 1 mL or greater, such as 2 mL or greater, such as 5 mL or greater, such as 10 mL or greater, such as 15 mL or greater, such as 25 mL or greater and including 100 mL or greater or may range such as from 0.01 mL to 1000 mL, such as from 0.05 mL to 900 mL, such as from 0.1 mL to 500 mL, such as from 0.5 mL to 400 mL, such as from 1 mL to 300 mL and including from 10 mL to 250 mL. In certain embodiments, where the analyte composition applied to the surface of the macroporous metal organic polymer matrix is a solid sample (e.g., tissue sample), the solid sample may be an amount sufficient to cover 1% or more of the macroporous metal organic polymer matrix surface, such as 2% or more, such as 5% or more and including 10% or more of the macroporous metal organic polymer matrix surface. For example, the solid biological sample may be an amount sufficient to cover between 1% and 10% of the macroporous metal organic polymer matrix surface, such as 2% to 9% of the macroporous metal organic polymer matrix surface and including from 3% to 7% of the macroporous metal organic polymer matrix surface. In these embodiments, the solid sample may have thickness which varies, ranging from 1 µm to 10,000 µm, such as from 5 µm to 1000 µm and including a thickness from 10 µm to 100 µm.

In practicing methods of the invention according to certain embodiments, a voltage is applied to the macroporous metal organic polymer matrix sufficient to produce analyte ions within the pores of the macroporous metal organic polymer matrix and expel the analyte ions from the macroporous metal organic polymer matrix. In embodiments of the invention, application of the voltage ionizes analytes of the analyte composition and produces a plume of analyte ions emanating from one or more vertices of the macroporous metal organic polymer matrix. The plume of analyte ions may be directed to the inlet of a mass analyzer such as a mass sprectrometer (as described in greater detail below) or the analyte ions emanating from the macroporous metal organic polymer matrix may be directed to a conduit (e.g., an ion separator) in communication with a mass analyzer.

The applied voltage may be any suitable voltage so long as it is sufficient to produce and expel analyte ions from the macroporous metal organic polymer matrix and may be 1 kV or greater, such as 2 kV or greater, such as 3 kV or greater, such as 4 kV or greater, such as 5 kV or greater, such as 7 kV or greater and including 10 kV or greater. For example, in certain embodiments the applied voltage may range from 1.5 kV to 9.5 kV, such as 2.5 kV to 8.5 kV, such as 3.5 kV to 7.5 kV and including 4.5 kV to 6.5 kV. The applied voltage may be in positive ion mode or negative ion mode.

The duration of applying voltage may vary depending on the analyte composition or analysis protocol and may be 0.01 minutes or longer, such as 0.05 minutes or longer, such as 0.1 minutes or longer, such as 0.5 minutes or longer, such as 1 minute or longer, such as 5 minutes or longer, such as 10 minutes or longer, such as 15 minutes or longer, such as 30 minutes or longer, such as 45 minutes or longer and including applying a voltage for 60 minutes or longer or may range such as from 0.01 minutes to 60 minutes, such as from 0.1 minutes to 45 minutes, such as from 1 minute to 30 minutes and including from 5 minutes to 15 minutes.

Voltage may be applied to the analyte containing macroporous metal organic polymer matrix using any convenient protocol, such as for example by connecting the macroporous metal organic polymer matrix to a source of an electric field or to electrodes configured to deliver a current to the macroporous metal organic polymer matrix.

In some embodiments, a voltage is continuously applied to the macroporous metal organic polymer matrix during certain steps of the subject methods. In some instances, the voltage is continuously applied to the macroporous metal organic polymer matrix before the analyte composition is applied, while the analyte composition is being applied and after the analyte composition has been applied to the macroporous metal organic polymer matrix. In other instances, a voltage is continuously applied to the macroporous metal organic polymer matrix before the analyte composition is applied and after the analyte composition has been applied to the macroporous metal organic polymer matrix. In yet other instances, a voltage is continuously applied to the macroporous metal organic polymer matrix while the analyte composition is being applied and is continued for the remainder of analysis.

Where necessary, the applied voltage may be changed at any time during methods of the invention. For example, a first voltage may be applied to the macroporous metal organic polymer matrix while the analyte composition is being applied to the macroporous metal organic polymer matrix and a second voltage is applied to the macroporous metal organic polymer matrix during analysis of the analyte ions. In another example a first voltage may be applied to the macroporous metal organic polymer matrix before the analyte composition is applied to the macroporous metal organic polymer matrix and a second voltage is applied during application of the analyte composition. In other words, the voltage may vary during different steps of the invention and any suitable combination of voltages may be employed.

In some embodiments, a voltage is applied immediately after the analyte composition is applied to the macroporous metal organic polymer matrix. In other embodiments, a voltage is applied after a predetermined period of time after the analyte composition is applied to the macroporous metal organic polymer matrix. For example, a voltage may be applied 0.0005 hours or more after the analyte composition is applied to the macroporous metal organic polymer matrix, such as 0.001 hours or more, such as 0.005 hours or more, such as 0.01 hours or more, such as 0.05 hours or more, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more and including applying a voltage 168 hours or more after the analyte composition is applied to the macroporous metal organic polymer matrix.

As such, methods according to certain embodiments may include a storage or prefabrication step where an analyte composition is preloaded onto the macroporous metal organic polymer matrix and is stored for a predetermined period of time before ionization and analysis of analyte ions. The amount of time the analyte composition is preloaded onto the macroporous metal organic polymer matrix before analysis may vary, such as 0.1 hours or more before analysis, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading an analyte composition onto the macroporous metal organic polymer matrix 240 hours or more before analysis or may range such as from 0.1 hours to 240 hours before analysis, such as from 0.5 hours to 216 hours, such as from 1 hour to 192 hours and including from 5 hours to 168 hours before analysis. For example, a biological sample (e.g., blood, urine, saliva, etc.) may be obtained and preloaded onto the macroporous metal organic polymer matrix at a remote location (e.g., at home using an at-home kit or in a physician's office) and sent to a laboratory for mass analysis.

In other embodiments, methods include contacting the surface of the macroporous metal organic polymer matrix with an analyte composition having biological macromolecules, such as proteins (including glycoproteins), enzymes, antibodies or other peptide-containing macromolecules, and maintaining the analyte composition in contact with the macroporous metal organic polymer matrix surface in a manner sufficient to cleave the biological macromolecules into fragments (e.g., peptide fragments).

In these embodiments, analyte ionization includes ionization of the products (e.g. peptide fragments) produced at or near the surface of the macroporous metal organic polymer matrix. For example, analyte ions may be produced by applying an ionization source (e.g., electrospray) to the surface of the analyte-containing macroporous metal organic polymer matrix and desorbing the analyte ions from the macroporous metal organic polymer matrix at or near the surface and directing the analyte ions to the inlet of a mass analyzer such as a mass sprectrometer (as described in greater detail below) or the analyte ions emanating from the macroporous metal organic polymer matrix surface may be directed to a conduit (e.g., an ion separator) in communication with a mass analyzer.

Surface and near surface ionization can include any convenient protocol so long as it is sufficient to produce and expel analyte ions from the macroporous metal organic polymer matrix. For example, suitable surface ionization protocols may include, but are not limited to, desorption electrospray (DESI), liquid extraction surface analysis, nano-DESI, laser assisted electrospray ionization, matrix-assisted laser desorption electrospray ionization, laser ablation electrospray ionization (LAESI) including infrared laser assisted desorption electrospray ionization (IR-LADESI) as well as desorption atmospheric pressure photoionization (DAPPI).

The duration of the applied surface ionization source (e.g., electrospray) may vary and may be 0.01 minutes or longer, such as 0.05 minutes or longer, such as 0.1 minutes or longer, such as 0.5 minutes or longer, such as 1 minute or longer, such as 5 minutes or longer, such as 10 minutes or longer, such as 15 minutes or longer, such as 30 minutes or longer, such as 45 minutes or longer and including applying a voltage for 60 minutes or longer or may range such as from 0.01 minutes to 60 minutes, such as from 0.1 minutes to 45 minutes, such as from 1 minute to 30 minutes and including from 5 minutes to 15 minutes.

The incident angle at which the ionization source (e.g., electrospray) is applied to the surface of the macroporous metal organic polymer matrix may also vary depending on the analyte composition (e.g., high or low molecular weight analytes) or analysis protocol and may range from 30° to 90°, such as from 35° to 85°, such as from 40° to 80°, such as from 45° to 75° and including from 50° to 70°. In some embodiments, the incident angle ranges from 70° to 90°. In other embodiments, the incident angle ranges from 35° to 50°. In certain embodiments, the incident angle at which the ionization source is applied to the macroporous metal organic polymer matrix surface is optimized based on the configuration of the analysis protocol. For example, where the analysis protocol is a mass spectrometer, the incident angle of surface ionization may be configured to optimize directing the analyte ions to the inlet of the mass spectrometer. This may, for example, be accomplished by using a movable contacting apparatus when applying the ionization source to the macroporous metal organic polymer matrix surface and adjusting the position of the macroporous metal organic polymer matrix with respect to the mass spectrometer inlet.

In some embodiments, ionization begins immediately after applying the composition to the macroporous metal organic polymer matrix surface. In other embodiments, ionization begins at a predetermined period of time after applying the composition to the macroporous metal organic polymer matrix surface. For example, ionization may be begin 0.01 minutes or longer, such as 0.05 minutes or longer, such as 0.1 minutes or longer, such as 0.5 minutes or longer, such as 1 minute or longer, such as 5 minutes or longer, such as 10 minutes or longer, such as 15 minutes or longer, such as 30 minutes or longer, such as 45 minutes or longer and including 60 minutes or longer after applying the composition to the macroporous metal organic polymer matrix.

In certain instances, a composition having biological macromolecules is applied to a macroporous metal organic polymer matrix having enzymes covalently bonded at or near the surface of the macroporous metal organic polymer matrix and maintained in contact with the enzyme-modified macroporous metal organic polymer matrix for a predetermined amount of time before ionization, such as 0.01 minutes or longer, such as 0.05 minutes or longer, such as 0.1 minutes or longer, such as 0.5 minutes or longer, such as 1 minute or longer, such as 5 minutes or longer, such as 10 minutes or longer, such as 15 minutes or longer, such as 30 minutes or longer, such as 45 minutes or longer and including maintaining the composition in contact with the enzyme-modified macroporous metal organic polymer matrix for 60 minutes before ionization of the analytes (e.g., cleavage products) produced at or near the surface of the enzyme-modified macroporous metal organic polymer matrix. For example, the composition may be maintained in contact with the enzyme-modified macroporous metal organic polymer matrix before ionization for a duration which ranges from 0.01 minutes to 60 minutes, such as from 0.1 minutes to 45 minutes, such as from 1 minute to 30 minutes and including from 5 minutes to 15 minutes. In other words, methods may include an incubation or storage period so that reactions (e.g., proteolysis) catalyzed by enzymes covalently bonded at or near the macroporous metal organic polymer matrix surface can occur.

Where necessary, the parameters of the surface ionization protocol may be changed at any time during methods of the invention. For example, parameters of the surface ionization protocol may be changed one or more times during the subject methods, such as two or more times, such as three or more times and including changing parameters of the surface ionization protocol five or more times.

In some embodiments, the incident angle at which the ionization source (e.g., electrospray) is applied to the surface of the macroporous metal organic polymer matrix may be changed during ionization. For example, the incident angle may be increased or decreased by 5° or more, such as by 8° or more, such as by 10° or more and including by 15° or more.

In other embodiments, the distance of the ionization source is positioned from the macroporous metal organic polymer matrix surface may be changed during the subject methods. For example, the ionization source may be positioned closer or further from the macroporous metal organic polymer matrix surface, as desired, by 1 mm or more, such as by 2 mm or more, such as by 5 mm or more, such as by 10 mm or more and including positioning the ionization source closer or further from the surface of the macroporous metal organic polymer matrix by 25 mm or more.

In yet other embodiments, where surface ionization includes an electrospray ionization protocol, parameters of the electrospray may be changed during the subject methods. For example, the gas and liquid flow rates of the electrospray may be increased or decreased by 10% or more, such as by 15% or more, such as by 25% or more and including by 50% or more. In other instances, the electrospray voltage may be changed, such as by increasing or decreasing electrospray voltage by 5% or more, such as by 10% or more, such as by 25% or more, such as by 50% or more, such as by 75% or more and including increasing or decreasing electrospray voltage by 90% or more.

In embodiments of the invention, methods include ionization of the analyte composition to produce and expel analyte ions from the macroporous metal organic polymer matrix. In some embodiments, ionization of the analyte composition is ambient ionization. The term "ambient ionization" is used in its conventional sense to refer to the formation of analytes ions outside of a mass spectrometer under atmospheric conditions at or near room temperature with little or no sample preparation or separation. In other embodiments, ionization of the analyte composition may be ionization under reduced pressure. In certain embodiments, methods include ion mobility coupled with mass spectrometry. The term "ion mobility" is used in its conventional sense to refer to the analytical technique used to separate and identify ionized molecules in gas phase based on their mobility in a carrier buffer gas. For example, ion-mobility may be in certain instances, drift-time ion mobility.

In some embodiments, methods also include applying a solvent to the macroporous metal organic polymer matrix. The solvent applied to the macroporous metal organic polymer matrix may be any suitable solvent including but not limited to water, methanol, ethanol, propanol, isopropanol, hexanes, acetonitrile, ethyl acetate, dimethylformamide, tetrahydrofuran, acetone, benzene, toluene among other solvents and combinations thereof. Solvent may be applied to the macroporous metal organic polymer matrix by any convenient protocol. In some embodiments, the solvent is applied to the surface of the macroporous metal organic polymer matrix. For example, solvent may be applied to the surface of the macroporous metal organic polymer matrix in the form of a droplet, such as when dispensed using a syringe, dropper or pipet. In another example, the solvent is sprayed onto the surface of the macroporous metal organic polymer matrix. In certain instances, solvent is applied to the surface of the macroporous metal organic polymer matrix in discrete amounts. In other instances, solvent is continuously applied to the surface of the macroporous metal organic polymer matrix, such as by a syringe pump. Where solvent is applied to the surface of the macroporous metal organic polymer matrix, the solvent subsequently diffuses into the interior pores of the macroporous metal organic polymer matrix.

In other embodiments, applying solvent to the macroporous metal organic polymer matrix includes injecting the solvent directly into the interior space of the macroporous metal organic polymer matrix. In some instances, solvent is injected into the macroporous metal organic polymer matrix in discrete amounts. In other instances, solvent is continuously injected into the macroporous organic polymer matrix, such as by using a syringe pump.

The amount of solvent applied to the macroporous metal organic polymer matrix at any given time may vary and may be 0.001 mL or greater, such as 0.005 mL or greater, such as 0.01 mL or greater, such as 0.05 mL or greater, such as 0.1 mL or greater, such as 0.5 mL or greater, such as 1 mL or greater, such as 5 mL or greater, such as 10 mL or greater, such as 15 mL or greater, such as 25 mL or greater, such as 50 mL or greater, such as 100 mL or greater, such as 250 mL or greater, such as 500 mL or greater and including 1000 mL or greater or may range such as from 0.001 mL to 1000 mL, such as from 0.01 mL to 900 mL, such as from 0.1 mL to 800 mL, such as from 1 mL to 600 mL, such as from 2 mL to 500 mL and including from 5 mL to 400 mL.

Solvent may be applied to the macroporous metal organic polymer matrix at any time during methods of the invention. In some embodiments, solvent is applied to the macroporous metal organic polymer matrix before application of the analyte composition, such as for example to prewet the macroporous metal organic polymer matrix. In other embodiments, solvent is applied immediately after the analyte composition is applied to the macroporous metal organic polymer matrix. In yet other embodiments solvent is applied simultaneously with application of the analyte composition to the macroporous metal organic polymer matrix.

In other embodiments, solvent is continuously applied to the macroporous metal organic polymer matrix during certain steps of the subject methods. In some instances, a solvent is continuously applied to the macroporous metal organic polymer matrix during analysis of the analyte ions. In other instances, solvent is continuously applied to the macroporous metal organic polymer matrix before the analyte composition is applied and while the analyte composition is being applied to the macroporous metal organic polymer matrix.

As described above, solvent may be applied to the analyte composition to dissolve the analyte composition in the macroporous metal organic polymer matrix. Alternatively, solvent may be used to dissolve the analyte composition prior to application to the macroporous metal organic polymer matrix.

In certain embodiments, methods include separating components of the analyte composition using the macroporous metal organic polymer matrix prior to ionization of the analyte composition. The term "separating" is used herein in its conventional sense to refer to the physical separation of a plurality of elements based on a particular property of each component including but not limited to separating components of the analyte composition by size, charge, affinity, or some other property.

Components of the analyte composition may be separated on the macroporous metal organic polymer matrix by any convenient protocol, including but not limited to filtration protocols, electrokinetic protocols, chromatagraphy protocols, among other separation protocols. In some embodiments, methods include separating components of the analyte composition using the macroporous metal organic polymer matrix by electrophoresis. In other embodiments, methods include separating components of the analyte composition using the macroporous metal organic polymer matrix by liquid chromatography (e.g., a reverse phase chromatography, an affinity chromatography, a size-exclusion chromatography, etc.). In yet other embodiments, methods include separating components of the analyte composition using the macroporous metal organic polymer matrix by filtration (e.g., size exclusion filtration or affinity filtration such as when the macroporous metal organic polymer matrix includes binding or recognition components). The macroporous metal organic polymer matrix in certain embodiments serves to extract the analytes from solution as well as provides the stationary phase for chromatographic separation of the analytes. In certain embodiments, analytes may be separated by performing normal phase, reverse phase, ion exchange, affinity, hydrophobic interaction, size-exclusion, or chiral chromatography on the macroporous metal organic polymer matrix.

Where components of the analyte composition are separated on the macroporous metal organic polymer matrix, separation may be conducted on an axis which is orthogonal to the axis for ionizing the analyte composition and producing and expelling analyte ions from the macroporous metal organic polymer matrix. In other embodiments, separation may be conducted on an axis which is parallel to the axis for ionizing the analyte composition and producing and expelling analyte ions from the macroporous metal organic polymer matrix.

In some instances, one or more components of the analyte composition may be concentrated in the macroporous metal organic polymer matrix. By concentrating, undesirable components of the analyte composition may be removed and the one or more components of the analyte composition of interest may be analyzed using methods of the invention described above. For example, the analyte composition may be applied to the macroporous metal organic polymer matrix and washed with solvent one or more times in order to reduce the amount of undesirable components of the analyte composition. In certain instances, a solvent gradient may be employed to enhance preconcentration of the analytes. In these instances, the analyte composition may be solvated using a solvent having a higher concentration of a water than in the solvent used during separation. The higher concentration of the water in the solvated analyte composition increases the affinity of the analyte composition to the macroporous metal organic polymer matrix.

Alternatively, components in an analyte composition may be separated by electrokinetic protocols such as by electrophoresis where application of an electric field to the macroporous metal organic polymer results in focusing of the desired components (i.e., compound stacking) at a concentration boundary where the electrophoretic velocity decreases in the macroporous metal organic polymer matrix. Where the analyte composition may be separated by electrokinetic protocols prior to analyte ionization, the electric field applied to the analyte containing macroporous metal organic polymer matrix may be from the same source or different electric field source as employed to ionize the analyte composition. For example, electrokinetic protocols may employ electrodes connected to the analyte-containing macroporous metal organic polymer matrix applying a voltage which is lower than used to ionize the analyte composition.

In certain embodiments, methods of the invention include analyzing compounds produced in situ at the surface or within the pores of the macroporous metal organic polymer matrix. In certain embodiments, compounds produced in situ are produced by a chemical reaction at the surface or within the pores of the macroporous metal organic polymer matrix. In other embodiments, compounds produced in situ are produced by a biochemical reaction at the surface or within the pores of the macroporous metal organic polymer matrix. In yet other embodiments, compounds produced in situ are produced by cells positioned at the surface or in the pores of the macroporous metal organic polymer matrix (e.g., metabolites produced by the cells). In yet other embodiments, compounds produced in situ are produced by microorganisms positioned at the surface or within the pores of the macroporous metal organic polymer matrix (e.g., metabolites produced by the microorganism).

Where compounds produced in situ are produced by a chemical reaction, one or more of the reactants may be preloaded onto the surface or into the pores of the macroporous metal organic polymer matrix such that when the analyte composition is applied to the macroporous metal organic polymer matrix, a chemical reaction occurs within the pores of the macroporous metal organic polymer matrix and the analytes produced by the chemical reaction may be analyzed by methods of the invention.

In some embodiments, compounds produced in situ are produced by a biochemical reaction (e.g., an enzyme catalyzed reaction). In these embodiments, a bioactive compound (e.g., enzyme) may be preloaded onto the surface or into the pores of the macroporous metal organic polymer matrix and an analyte composition containing one or more substrates of the bioactive compound may be applied to the macroporous metal organic polymer matrix and the analytes produced by the biochemical reaction may be analyzed by methods of the invention. For example, as discussed above, the analyte composition may include biological macromolecules such as proteins (including glycoproteins), enzymes, antibodies or other peptide-containing macromolecules and peptide fragments produced in situ at or near the macroporous metal organic polymer matrix surface by enzymatic proteolysis are analyzed by methods of the invention.

In these embodiments, any suitable bioactive compound may be bonded to the macroporous metal organic polymer matrix (either on the surface or within the pores), as desired. In certain embodiments, macroporous metal organic polymer matrices of interest include protease enzymes. The term "protease enzyme" is used herein in its conventional sense to refer to the class of enzymes which conduct proteolysis and may include serine proteases, threonine proteases, cysteine proteases, aspartate proteases, glutamic acid proteases and metalloproteases, acid proteases, alkaline proteases, among other types of proteolytic enzymes. For example, proteases of interest may include, but are not limited to, trypsin, chymotrypsin, pepsin, papain, bromelain, serratia peptidase, subtilisin, elastases, dipeptidase E, penicillin G acylase, DmpA aminopeptidase, prolyl oligopeptidase, D-Ala-D-Ala peptidase C, signal peptidase, cytomegalovirus assembling, Lon-A peptidase, peptidase C1p, E. coli phage K1F endosialidase, nucleoporin, lactoferrin, murein tetrapeptidase LD-carboxypeptidase, rhomboid-1, fecal elastase, archaean proteasome, ornithine acetyltransferase, TEV protease, amidophosphoribosyltransferase, gamma-glutamyl hydrolase, hedgehog protein, caspase-1, separase, adenain, pyroglutamyl-peptidase, sortase A, dipeptidyl-peptidase VI, DeSI-1 peptidase, Beta-secretase 1, Cathepsin D, Cathepsin E, Chymosin, Napsin, Nepenthesin, calpain, plasmepsin, presenilin, renin, disintegrin and metalloproteinases, ADAM proteins, as well as other types of exopeptidases and endopeptidases.

In certain embodiments, methods include analyzing compounds such as metabolites produced by cells or microorganisms. The term "metabolites" is used herein its conventional sense to refer to one or more compounds found which are the substrates or products of metabolic process which occur within a cell. As such, metabolites may include substrates or products which are produced by metabolic processes including, but not limited to glycolysis, tricarboxylic acid cycle (i.e., TCA cycle, Krebs cycle), reductive pentose phosphate cycle (i.e., Calvin cycle), glycogen metabolism, pentose phosphate pathway, among other metabolic processes. Accordingly, metabolites of interest may include but are not limited to glucose, glucose-6-phosphate, fructose-6-phosphate, fructose-1,6-phosphate, glyceraldehyde 3-phosphate, dihydroxyacetone phosphate, 1,3-bisphosphoglycerate, 3-phosphoglycerate, 2-phosphoglycerate, phosphoenolpyruvate, pyruvate, acetyl CoA, citrate, cis-aconitate, d-isocitrate, α-ketoglutarate, succinyl CoA, succinate, fumarate, malate, oxaloacetate, ribulose 1,5-bisphosphate, 3-phosphoglycerate, 1,3-bisphosphoglycerate, glyceraldehyde 3-phosphate, ribulose-5-phosphate, ethanol, acetaldehyde, pyruvic acid, 6-phosphogluconolactone, 6-phosphogluconate, ribose-5-phosphate, xylulose-5-phosphate, sedoheptulose 7-phosphate, erythrose 4-phosphate, among other metabolites. In these embodiments, the cells or microorganisms may be preloaded onto the surface or into the pores of the macroporous metal organic polymer matrix and analytes produced by the microorganism may be analyzed by methods of the invention.

As summarized above, methods of the invention also include analyzing the analyte ions. By "analyzing" is meant characterizing the chemical make-up of the analyte composition, including but not limited to the amount and types of compounds in the analyte composition as well as any impurities present. Chemical analysis may be conducted using any convenient protocol which measures the mass-to-charge ratio of the analyte ions and may include, but is not limited to mass spectrometry, infrared spectroscopy, UV-vis spectroscopy, ion mobility spectrometry and ion spectroscopy. In some embodiments, chemical analysis is conducted by mass spectrometry. In certain embodiments, chemical analysis is conducted by ion-mobility mass spectrometry.

Analysis of the analyte ions may begin at any time after ionization of the analyte from the macroporous metal organic polymer matrix. In some embodiments, analysis begins immediately after application of the voltage to the macroporous metal organic polymer matrix. In other embodiments, analysis begins after a predetermined period of time after application of the voltage, such as after 0.001 minutes or more, such as 0.005 minutes or more, such as 0.01 minutes or more, such as after 0.05 minutes or more, such as after 0.1 minutes or more, such as after 0.5 minutes or more, such as after 1 minute or more and including after 5 minutes or more or may range such as from 0.0005 minutes to 10 minutes, such as from 0.001 minutes to 9.5 minutes, such as from 0.01 minutes to 9 minutes, such as from 0.05 minutes to 7 minutes and including from 0.1 minutes to 5 minutes after application of the voltage. In certain embodiments, analysis may begin prior to application of the voltage to the macroporous metal organic polymer matrix, such as for example to measure background signal or as a control measurement. In these embodiments, analysis may begin 0.0005 minutes or more before application of the voltage, such as 0.001 minutes or more, such as 0.05 minutes or more, such as 0.5 minutes or more, such as 1 minutes or more and including beginning analysis 5 minutes or more before application of the voltage or may range such as from 0.01 minutes to 10 minutes, such as from 0.1 minutes to 9 minutes, such as from 0.5 minutes to 7 minutes and including from 1 minute to 5 minutes before application of the voltage.

In other embodiments where analytes produced at or near the surface of the macroporous metal organic polymer matrix are analyzed, analysis may begin immediately after application of the source of ionization to the macroporous metal organic polymer matrix surface (e.g., immediately after beginning desorption electrospray ionization). In other embodiments, analysis begins after a predetermined period of time after application of the source of ionization to the macroporous metal organic polymer matrix surface, such as after 0.001 minutes or more, such as 0.005 minutes or more, such as 0.01 minutes or more, such as after 0.05 minutes or more, such as after 0.1 minutes or more, such as after 0.5 minutes or more, such as after 1 minute or more and including after 5 minutes or more or may range such as from 0.0005 minutes to 10 minutes, such as from 0.001 minutes to 9.5 minutes, such as from 0.01 minutes to 9 minutes, such as from 0.05 minutes to 7 minutes and including from 0.1 minutes to 5 minutes after application of the source of ionization to the macroporous metal organic polymer matrix surface. In certain embodiments, analysis begins prior to application of the source of ionization to the macroporous metal organic polymer matrix surface, such as for example to measure background signal or as a control measurement. In these embodiments, analysis may begin 0.0005 minutes or more before application of the source of ionization to the macroporous metal organic polymer matrix surface, such as 0.001 minutes or more, such as 0.05 minutes or more, such as 0.5 minutes or more, such as 1 minutes or more and including beginning analysis 5 minutes or more before application of the source of surface analyte ionization or may range such as from 0.01 minutes to 10 minutes, such as from 0.1 minutes to 9 minutes, such as from 0.5 minutes to 7 minutes and including from 1 minute to 5 minutes before application of the source of ionization to the macroporous metal organic polymer matrix surface.

Depending on the analysis protocol (e.g., type of mass spectrometer), analysis of the analyte ions may be discrete or continuous. In some embodiments, analyte ions may be analyzed at discrete, predetermined times. For example, measurements such as by a mass spectrometer may be taken every 0.01 minutes, such as 0.05 minutes, such as every 0.1 minutes, such as every 0.5 minutes, such as every 1 minute, such as every 5 minutes, such as every 10 minutes and including taking a measurement every 30 minutes. Alternatively, analyte ions may be continuously analyzed and measurements are reported in real-time.

In some embodiments, the subject macroporous metal organic polymer matrix is reusable. By "reusable" is meant that the macroporous metal organic polymer matrix is capable of more than a single use where there is little to no degradation or reduction in performance by the macroporous metal organic polymer matrix after each use in methods of the invention. As such, the subject macroporous metal organic polymer matrice may be reused 1 more or times, such as 2 or more times, such as 3 or more times, such as 5 or more times, such as 10 or more times, such as 25 or more times, such as 50 or more times and including 100 or more times.

In embodiments of the invention, macroporous metal organic polymer matrices show little to no degradation or reduction in performance after each use. The subject macroporous metal organic polymer matrices degrade by 5% or less during each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including degrading by 0.1% or less during each use. In certain embodiments, there is no degradation of the macroporous metal organic polymer matrix during each use. Likewise, the performance of the macroporous metal organic polymer matrix is reduced by by 5% or less after each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including a reduction in performance by 0.1% or less after each use. In certain embodiments, the performance of the macroporous metal organic polymer matrix is entirely unaffected by each use.

Where the macroporous metal organic polymer matrix is reused, methods may further include washing the macroporous metal organic polymer matrix after use or prior to subsequent use. The macroporous metal organic polymer matrix may be washed by any convenient protocol, such as by washing with a solvent with or without applying a voltage. Alternatively, the macroporous metal organic polymer matrix may be washed using heat, electromagnetic radiation (e.g., ultraviolet light) or by ultrasound, among other washing protocols.

Macroporous Metal Organic Polymer Matrices

As summarized above, aspects of the invention also include macroporous metal organic polymer matrices suitable for practicing the subject methods (e.g., macroporous metal organic polymer matrix mass spectrometry emitters). Macroporous metal organic polymer matrices of interest includes a metal organic, or metalorganic polymer. Macroporous metal organic polymer matrices of the invention are porous sol-gel polymeric substrates prepared from metal organic monomeric precursors. A precursor of the macroporous metal organic polymer may be a metal alkoxide or mixture of metal alkoxides having a metal-oxygen-carbon linkage or metalloid-oxygen-carbon linkage. Suitable metals according to certain embodiments include but are not limited to aluminum, barium, antimony, calcium, chromium, copper, erbium, germanium, iron, lead, lithium, phosphorus, potassium, silicon, tantalum, tin, titanium, vanadium, zinc, zirconium or combinations thereof.

In some embodiments, precursors of macroporous metal organic polymer matrices of interest may be of the formula:

$$(RO)_y M_x (R_1)_z,$$

where x is an integer from 1 to 4;
y is an integer from 0 to 4;
z is an integer from 0 to 4;
where at least one of y or z are 1 or greater;
M is aluminum, barium, antimony, calcium, chromium, copper, erbium, germanium, iron, lead, lithium, phosphorus, potassium, silicon, tantalum, tin, titanium, vanadium, zinc or zirconium;
R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
$R_1$ is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl.

In certain embodiments, macroporous metal organic polymer matrices of interest are organosiloxane polymer matrices and are prepared from organosiloxane precursors. For example, organosiloxane polymer matrices of interest include polymeric composition prepared from organosiloxane precursors which may include, but are not limited to methyltrimethoxysilane, dimethyldimethoxysilane, tetraethoxysilane, methacryloxypropyltrimethoxysilane, bis(triethoxysilyl)ethane, bis(triethoxysilyl)butane, bis(triethoxysilyl)pentane, bis(triethoxysilyl)hexane, bis(triethoxysilyl)heptane, bis(triethoxysilyl)octane, and combinations thereof.

In preparing the subject macroporous metal organic polymer matrices, the metal organic precursors may be combined with a catalyst (e.g., an acid or base) to hydrolyze the precursor. For example, where the macroporous metal organic polymer matrix is an organosiloxane polymer, silane precursors may undergo hydrolysis to form a hydrolyzed silane. Depending on the desired macroporous metal organic polymer matrix, the precursors may be fully or partially hydrolyzed.

A porogen or a mixture of porogens may be mixed with the metal organic precursors and the catalyst, such that the metal organic precursors undergo a condensation reaction to form the macroporous polymeric metal organic matrix. The porogen provides a molecular template to form pores within the matrix. For example, the porogen may be a solvent (e.g., toluene), a polymer (e.g., cellulose, poly(methyl methacrylate) or polystyrene), or an inorganic salt (e.g, powdered sodium chloride or sodium sulfate). Any suitable porogen may be employed so long as it is sufficient to form pores within the desired pores in the macroporous metal organic polymer matrix. The porosity of the subject macroporous metal organic polymer matrices may be controlled by the type of porogen, volume or concentration in the reaction mixture.

In certain embodiments, the macroporous metal organic polymer matrix is formed on the surface of a substrate (e.g., by casting the macroporous metal organic polymer matrix on the surface or in a mold placed on the surface of the substrate). The term "substrate" is used herein to refer to a solid surface which can suitably contain or accommodate one or more of the applied macroporous metal organic polymer matrices described herein. The substrate may be any substrate so long as analyte ions can be produced and expelled from the macroporous metal organic polymer matrix positioned on the substrate. Suitable materials for substrates may include, but are not limited to glass, plastic or polymeric materials such as thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate). The thickness of the substrate may vary ranging from 0.001 mm to 1 mm, such as 0.005 mm to 0.5 mm including ranging from 0.01 mm to 0.1 mm. Likewise, the thickness of the macroporous metal organic polymer matrix may vary ranging from 0.001 mm to 25 mm, such as 0.005 mm to 15 mm including ranging from 0.01 mm to 10 mm. In certain embodiments, the macroporous metal organic polymer matrix is covalently bonded to the substrate. In other embodiments, the macroporous metal organic polymer matrix is physically associated with the substrate (i.e., by non-covalent bonds). The macroporous metal organic polymer matrix formed on the surface of a substrate (e.g., glass or plastic) may cover all or part of the substrate. In some embodiments, the macroporous metal organic polymer matrix may be formed on 5% or more of the substrate surface, such as 10% or more, such as 25% or more, such as 35% or more, such as 50% or more, such as 75% or more, such as 90% or more, such as 95% or more and including 99% or more. In certain embodiments, the macroporous metal organic polymer matrix covers the entire surface of the substrate.

In certain instances, the macroporous metal organic polymer matrix is formed on the surface of the substrate at discrete locations. The positions of the discrete locations on the substrate surface may be in a random pattern or non-random pattern, including in patterns of specific shapes (circle, square, triangle or other polygon), letter or number configurations or image configurations, as desired. For example, the macroporous metal organic polymer matrix may be formed in a multi-site array pattern. Each discrete location may be the same or different size, as desired and may range from 0.01 to 5 cm$^2$, such as 0.05 to 5 cm$^2$, such as 0.1 to 4.5 cm$^2$, such as 0.25 to 4.5 cm$^2$, such as 0.5 to 4 cm$^2$ and including 1 to 4 cm$^2$.

Depending on the types of metal alkoxide precursors, polymeric material or conditions used to prepare the macroporous metal organic polymer matrix, the macroporous metal organic polymer matrix at each discrete location may have the same or different macrostructure from each other with respect to one or more physical property, such as pore size, opacity, hardness, electrical conductivity, flexibility, surface wettability, etc. For example, in some embodiments each discrete location includes a macroporous metal organic polymer matrix having macrostructure which differs in one or more physical properties. In these instances, the discrete locations may include macroporous metal organic polymer matrices having macrostructure which differ in one or more of pore size, opacity, hardness, electrical conductivity, flexibility, surface wettability, etc.

In embodiments where the macroporous metal organic polymer matrix is further modified, such as by covalently bonding one or more enzymes, the macroporous metal organic polymer matrix may, in certain instances, cover all or part of the glass or plastic substrate, but are modified only at discrete locations. In these embodiments, the glass or plastic substrate is uniformly covered with the macroporous metal organic polymer matrix, but reactivity by the bonded biologically active compound is found only at distinct locations at or near the macroporous metal organic polymer matrix surface. Each discrete location may have the same or different modification (e.g., biologically active compound), as desired. For example, the macroporous metal organic polymer matrix may have two or more discrete modified locations having different biologically active compounds, such as three or more discrete surface-modified locations, such as 5 or more discrete surface-modified locations, such as 10 or more discrete surface-modified locations, such as 16 or more discrete surface-modified locations, such as 64 more discrete surface-modified locations and including 96 or more discrete surface-modified locations having different biologically active compound. In other embodiments, each discrete location may be surface-modified with the same biologically active compound, but the biologically active compound is present at each discrete location in different amounts. The size of each modified location on the macroporous metal organic polymer matrix surface may be the same or different size, as desired and may range from 0.01 to 5 cm$^2$, such as 0.05 to 5 cm$^2$, such as 0.1 to 4.5 cm$^2$, such as 0.25 to 4.5 cm$^2$, such as 0.5 to 4 cm$^2$ and including 1 to 4 cm$^2$.

Depending on the chemical constitution of specific metal organic precursors and reaction conditions employed, the physical properties (e.g., opacity, flexibility, hardness, porosity) of macroporous metal organic polymer matrices of interest may vary. In certain embodiments, the subject macroporous metal organic polymer matrix is a sol-gel.

Macroporous metal organic polymer matrices are porous polymeric substrates. Depending on the chemical constitution of specific metal organic precursors and porogens employed, pore sizes may vary, ranging from 0.01 µm to 50 µm, such as from 0.1 µm to 49 µm, such as 0.05 µm to 45 µm, such as 0.1 µm to 40 µm, such as 0.5 µm to 35 µm, such as 1 µm to 30 µm and including 5 µm to 25 µm. Where the pores of the macroporous metal organic polymer matrix are employed to encapsulate or covalently bind a bioactive compound (e.g., enzyme, antibody, etc. as described in greater detail below), macroporous metal organic polymer matrices include pore sizes sufficient to contain the bioactive compound within the matrix. As such, the pore size may be 0.01 µm or greater, such as 0.05 µm or greater, such as 0.1 µm or greater, such as 0.5 µm or greater, such as 1 µm or greater, such as 5 µm and including 10 µm or greater. In certain embodiments, metal organic polymer matrices have no pores.

As discussed in detail above, in embodiments where a voltage is applied to the macroporous metal organic polymer matrix, analyte ions are produced and expelled based on the high electric field generated at a sharp point of the macroporous metal organic polymer matrix. As such, macroporous metal organic polymer matrices of interest, in these embodiments, are configured with one or more vertices. The tip angle of the subject macroporous metal organic polymer matrix may vary, having a tip angle which ranges from 0.1° to 170°, such as from 0.5° to 165°, such as from 1° to 160°, such as from 5° to 155°, such as from 10° to 150°, such as from 20° to 145°, such as from 25° to 140°, such as from 30° to 135°, such as from 35° to 130°, such as from 40° to 125° and including a tip angle which varies from 45° to 120°. In some embodiments, the macroporous metal organic polymer matrix includes one or more vertices having a tip angle of 30°. In other embodiments, the macroporous metal organic polymer matrix includes one or more vertices having a tip angle of 60°. In yet other embodiments, the macroporous metal organic polymer matrix includes one or more vertices having a tip angle of 90°. In still other embodiments, the macroporous metal organic polymer matrix includes one or more vertices having a tip angle of 120°. The size of the vertices of the subject macroporous metal organic polymer matrix may also vary, as desired and may be 1 µm or wider, such as 2 µm or wider, such as 5 µm or wider, such as 10 µm or wider, such as 25 µm or wider and including 50 µm or wider or may range such as from 1 µm to 100 µm, such as from 2 µm to 75 µm, such as from 3 µm to 50 µm and including from 5 µm to 25 µm.

In other embodiments, macroporous metal organic polymer matrices may be any desired shape, such a circle, oval, half-circle, crescent-shaped, star-shaped, square, triangle, rhomboid, pentagon, hexagon, heptagon, octagon, rectangle or other suitable polygon. In other embodiments, macroporous metal organic polymer matrices are three-dimensional, such as in the shape of a cube, cone, half sphere, star, triangular prism, rectangular prism, hexagonal prism or other suitable polyhedron.

In some embodiments, macroporous metal organic polymer matrices are castable compositions where the term "castable" is used in its conventional sense to refer to a composition which can be molded into a desired shape (e.g., by placing the composition into a shaped mold or substrate) and may be subsequently hardened to form the final macroporous metal organic polymer matrix. As such, the subject macroporous metal organic polymer matrix may be formed into any convenient shape and size. For example, macroporous metal organic polymer matrices may be planar and in the shape of a triangle, square, rectangle, rhomboid, pentagon, hexagon, heptagon, octagon, half circle, crescent-shaped, star shaped, or some other convenient shape. In other embodiments, macroporous metal organic polymer matrices are three-dimensional, such as in the shape of a cube, cone, half sphere, star, triangular prism, rectangular prism, hexagonal prism or other polyhedron. In certain instances, the subject macroporous metal organic polymer matrices may be produced by cutting sheets of the polymer matrix into the desired shape. For example, a macroporous metal organic polymer matrix may be cast as a square, circular, rectangular (or some other shaped) sheet and cutting out the desired shape (such as by scissors or any other convenient cutting tool). In certain instances, where the desired shape of macroporous metal organic polymer matrix is a polygon, the sheet from which it is cut may be a rectangle, square or some other polygon, as convenient. In other instances, where the desired shape of macroporous metal organic polymer matrix is a crescent or half circle, the sheet from which it is cut may be a circle.

The size of the macroporous metal organic polymer matrix may vary. Where the macroporous metal organic polymer matrix is planar, the surface area may range from 0.1 to 5 cm$^2$, such as 0.5 to 5 cm$^2$, such as 1.0 to 5 cm$^2$, such as 1.5 to 4.5 cm$^2$, such as 2.0 to 4 cm$^2$, such as 2.5 to 3.5 cm$^2$, and including 2 to 3 cm$^2$. Where the macroporous metal organic polymer matrix is three-dimensional, the size may range from 0.1 to 5 cm$^3$, such as 0.5 to 5 cm$^3$, such as 1.0 to 5 cm$^3$, such as 1.5 to 4.5 cm$^3$, such as 2.0 to 4 cm$^3$, such as 2.5 to 3.5 cm$^3$, and including 2 to 3 cm$^3$.

In certain embodiments, the macroporous metal organic polymer matrix is flexible. The term "flexible" is used in its conventional sense to mean that the macroporous metal organic polymer matrix is capable of being bent without breaking or otherwise able to be turned, bowed, or twisted, without breaking. In these embodiments, the macroporous metal organic polymer matrix may be pliable and is not rigid or stiff. In other embodiments, the macroporous metal organic polymer matrix is rigid. The term "rigid" is used in its conventional sense to mean that the macroporous metal organic polymer matrix is stiff and not capable of substantially being bent without breaking.

Depending on the chemical constitution of specific metal organic precursors and reaction conditions employed, the durometer hardness of macroporous metal organic polymer matrices of interest may vary. In certain embodiments, the durometer hardness of subject macroporous metal organic polymer matrices ranges from 10 Shore OO to 100 Shore OO, such as 20 Shore OO to 90 Shore OO, such as 30 Shore OO to 80 Shore OO and including 40 Shore OO to 70 Shore OO. In other embodiments, the durometer hardness of subject macroporous metal organic polymer matrices ranges from 10 Shore A to 100 Shore A, such as 20 Shore A to 90 Shore A, such as 30 Shore A to 80 Shore A and including 40 Shore A to 70 Shore A.

The opacity of macroporous metal organic polymer matrices to visible light may vary. In some embodiments, macroporous metal organic polymer matrices are transparent. In other embodiments, macroporous metal organic polymer matrices are translucent to visible light. In yet other embodiments, macroporous metal organic polymer matrices are opaque to visible light.

Depending on the types of metal alkoxide precursors, polymeric material or conditions used to prepare the macroporous metal organic polymer matrix, the macroporous metal organic polymer matrix may include two or more distinct regions of macrostructure which differ from each other with respect to one or more physical property, such as pore size, hardness, opacity, flexibility, etc. For example, in some embodiments macroporous metal organic polymer matrices of interest include two distinct regions of macrostructure differing in one or more physical properties. In other embodiments, macroporous metal organic polymer matrices of interest include three distinct regions of macrostructure differing in one or more physical properties. In some instances the distinct regions of macrostructure differ in terms of pore size. In other instances, the distinct regions of macrostructure differ in terms of opacity. In yet other instances, the distinct regions of macrostructure differ in terms of hardness. In yet other instances, the distinct regions of macrostructure differ in terms of pore size and opacity. In yet other instances, the distinct regions of macrostructure differ in terms of pore size and hardness. In yet other instances, the distinct regions of macrostructure differ in terms of opacity and hardness. In yet other instances, the distinct regions of macrostructure differ in terms of pore size, opacity and hardness. Where the macroporous metal organic polymer matrix includes more than two or more distinct regions of macrostructure, the percentage of each region may be 5% or greater, such as 10% or greater, such as 25% or greater, such as 50% or greater, such as 75% or greater and including 90% or greater. As such the size of each region may range from 0.5 to 5 cm$^2$, such as 1.0 to 5 cm$^2$, such as 1.5 to 4.5 cm$^2$, such as 2.0 to 4 cm$^2$, such as 2.5 to 3.5 cm$^2$, and including 2 to 3 cm$^2$.

The physical properties of the subject macroporous metal organic polymer matrices may be varied as desired based on parameters in preparing the matrix such as, but not limited to:

Variations in metal:water ratio (e.g., Si:water);

Variations in metal organic monomer:water:catalyst ratio (e.g., MTMS:DMDMS:water:acid catalyst ratio);

Variations in metal organic monomer:water:catalyst:urea ratio (e.g., MTMS:DMDMS:water:acid catalyst:urea ratios);

Additions of surfactants, such as CTAB, to suppress phase separation in the reaction;

Variations in the reaction temperature from 0° C. to 85° C.;

Variations in catalysis using either acid or a 2-step acid/base catalyst system;

Additions of pore templates such as polyethylene glycol (PEG) with molecular weights, ranging from 1,000 to 10,000 daltons;

Different types of molds made from plasma-oxidized polystyrene to polycarbonate to polydimethylsiloxane (PDMS) to polypropylene;

Variations in the stirring time (i.e., hydrolysis reaction);

Variations in the gelation and aging times (i.e., condensation reaction);

Macroporous metal organic polymer matrices of interest may be functionalized with different functional groups as desired by preparing the subject macroporous metal organic polymer matrices with the precursors having the desired functional group. Alternatively, the macroporous metal organic polymer matrix may be derivatized with functional groups after polymerization of precursor components. The subject macroporous metal organic polymer matrices may include any functional group, including but are not limited to alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl, substituted arylalkyl, aldehyde, amine, amide, alkoxy, carboxylic acid, ester, ether, hydroxyl, imine, isocyanate, acyl, formyl, and thionyl, among other functional groups.

In some embodiments, aspects of the invention further include one or more bioactive compounds (e.g., biomolecules) covalently bonded to the surface or within the pores of the subject macroporous metal organic polymer matrices. For example, macroporous metal organic polymer matrices may contain compounds such as, but not limited to polymers, peptides, proteins, enzymes, polysaccharides, antibodies, oligonucleotides, luminescent compounds, cellular components, whole cells, microorganisms among other active compounds. In certain instances, macroporous metal organic polymer matrices of interest include enzymes bonded at or near the surface. For example, these enzymes may be protease enzymes. As discussed above, a "protease enzyme" is an enzyme which conducts proteolysis and may include serine proteases, threonine proteases, cysteine proteases, aspartate proteases, glutamic acid proteases and metalloproteases, acid proteases, alkaline proteases, among other types of proteolytic enzymes. For example, proteases of interest may include, but are not limited to, trypsin, chymotrypsin, pepsin, papain, bromelain, *serratia* peptidase, subtilisin, elastases, dipeptidase E, penicillin G acylase, DmpA aminopeptidase, prolyl oligopeptidase, D-Ala-D-Ala peptidase C, signal peptidase, cytomegalovirus assembling, Lon-A peptidase, peptidase C1p, *E. coli* phage K1F endosialidase, nucleoporin, lactoferrin, murein tetrapeptidase LD-carboxypeptidase, rhomboid-1, fecal elastase, archaean proteasome, ornithine acetyltransferase, TEV protease, amidophosphoribosyltransferase, gamma-glutamyl hydrolase, hedgehog protein, caspase-1, separase, adenain, pyroglutamyl-peptidase, sortase A, dipeptidyl-peptidase VI, DeSI-1 peptidase, Beta-secretase 1, Cathepsin D, Cathepsin E, Chymosin, Napsin, Nepenthesin, calpain, plasmepsin, presenilin, renin, disintegrin and metalloproteinases, ADAM proteins, as well as other types of exopeptidases and endopeptidases, In certain instances, the protease enzyme is trypsin, chymotrypsin or pepsin among other protease enzymes.

Bioactive compounds may be covalently bonded to the macroporous metal organic polymer matrix. As such, one or more covalent bonds is formed between the macroporous metal organic polymer matrix and the bioactive compound of interest, such as for example a covalent bond formed between the bioactive compound and the surface of the macroporous metal organic polymer matrix or along the pore walls of the macroporous metal organic polymer matrix. In one example, an enzyme is bonded by one or more covalent bonds to the macroporous metal organic polymer matrix. For example, the enzyme may be covalently bonded to the surface of the macroporous metal organic polymer matrix. In certain instances, macroporous metal organic polymer matrices of interest include a protease enzyme covalently bonded to the surface of the macroporous metal organic polymer matrix. In other instances, a protease enzyme is covalently bonded at the surface and within the pores of the macroporous metal organic polymer matrix. In a second example, a protein is bonded to the macroporous metal organic polymer matrix by one or more covalent bonds. In a third example, an antibody is bonded to the macroporous metal organic polymer matrix by one or more covalent bonds. In a fourth example, an oligonucleotide is bonded to the macroporous metal organic polymer matrix by one or more covalent bonds.

Alternatively, bioactive compounds may be physically associated with the macroporous metal organic polymer matrix such as by adsorption to the surface of the macroporous metal organic polymer matrix, encapsulation within the pores of the matrix, or by non-covalent bonds, including ionic interactions, van der Waals forces, hydrogen bonding, dipole-dipole interactions, ion-dipole interactions, among other types of non-covalent interactions. For example, in one instance, an enzyme may be encapsulated within the pores of the macroporous metal organic polymer matrix. In another instance, an oligonucleotide is encapsulated within the pores of the macroporous metal organic polymer matrix. In yet another instance, one or more whole cells are encapsulated within the pores of the macroporous metal organic polymer matrix. In still another instance, one or more microorganisms are encapsulated within the pores of the macroporous metal organic polymer matrix.

Where one or more bioactive compounds are associated (covalently or non-covalently) with the macroporous metal organic polymer matrix, the amount (i.e., mass) of bioactive compound present may vary ranging from 0.001 mg to 100 mg, such as 0.01 mg to 50 mg, such as 0.1 mg to 25 mg, such as 0.5 mg to 10 mg, such as 1 mg to 5 mg, including 2 mg to 3 mg. As such, the bioactive compound may be present in the macroporous metal organic polymer matrix in an amount ranging from 0.05% to 35% w/w, such as 0.1% to 30% w/w, such as 0.5% to 25% w/w, such as 0.75% to 20% w/w, such as 1% to 15% w/w, such as 1.5% to 12.5% w/w and including 2% to 10% w/w. Where the bioactive compound is positioned on the surface of the macroporous metal organic polymer matrix, the bioactive compound may cover 1% or more of the macroporous metal organic polymer matrix surface, such as 5% or more, such as 10% or more, such as 25% or more, such as 35% or more, such as 50% or more, such as 75% or more, such as 90% or more, such as 95% or more and including 99% or more of the macroporous metal organic polymer matrix surface. In certain embodiments, bioactive compounds positioned (e.g., covalently or non-covalently) on the surface of the macroporous metal organic polymer matrix cover the entire macroporous metal organic polymer matrix surface.

The one or more bioactive compounds can be introduced to the subject macroporous metal organic polymer matrix by any convenient protocol. For example, the one or more active compounds may be added to a macroporous metal organic polymer matrix precursor composition and the one or more bioactive compounds may be encapsulated when forming the final macroporous metal organic polymer matrix. Alternatively, an already formed macroporous metal organic polymer matrix may be incubated in the presence of the one or more bioactive compounds with or without a solvent for a predetermined amount of time, such as for 1 hour or more, 5 hours or more, 10 hours or more, 12 hours or more, 24 hours or more, 3 days or more and including 1 week or more, to allow the macroporous metal organic polymer matrix to physically incorporate the one of more active compounds into the matrix.

In some embodiments, the one of more bioactive compounds are covalently bonded to the macroporous metal organic polymer matrix. Where the bioactive compound is covalently bonded, macroporous metal organic polymer matrices of interest may be covalently bonded with the bioactive compound by preparing the subject macroporous metal organic polymer matrices with precursors covalently bonded to the desired bioactive compound. Alternatively, the bioactive compound may be covalently bonded to the macroporous metal organic polymer matrix through functional groups found on the surface of the macroporous metal organic polymer matrix or along the pore walls of the macroporous metal organic polymer matrix. In certain instances, the bioactive compound is an enzyme (e.g., protease enzyme) and the enzyme is covalently bonded to the surface of the macroporous metal organic polymer matrix through one or more reactive groups (e.g., aldehyde) functionalized on the macroporous metal organic polymer matrix surface.

As discussed above, in certain embodiments components of an analyte composition may be separated using the macroporous metal organic polymer matrix. As such, in these embodiments the macroporous metal organic polymer matrix includes macrostructure configured to separate one or more compounds. For example, in some instances the subject macroporous metal organic polymer matrix is a chromatography matrix (e.g., a reverse phase chromatography substrate, an affinity chromatography substrate, a size-exclusion chromatography substrate, etc.). In other instances, the subject macroporous metal organic polymer matrix is a filtration matrix (e.g., a size exclusion filter or an affinity filter such as when the macroporous metal organic polymer matrix includes binding or recognition components). In certain instances, the macroporous metal organic polymer matrix is an matrix configured for an electrokinetic protocol. All or part of the macroporous metal organic polymer matrix may include macrostructure configured to separate one or more compounds. For example, 5% or more of the macroporous metal organic polymer matrix may include macrostructure configured to separate components of an analyte composition, such as 10% or more, such as 25% or more, such as 50% or more, such as 75% or more, such as 90% or more and including 95% or more of the macroporous metal organic polymer matrix may include macrostructure configured to separate components of an analyte composition. In certain embodiments, the entire macroporous metal organic polymer matrix includes macrostructure configured to separate components of an analyte composition. The macroporous metal organic polymer matrix may be composed of one or more types of macrostructure configured to separate components of an analyte composition. In some embodiments, the macroporous metal organic polymer matrix may include 2 or more types of macrostructure configured to separate components of an analyte composition, such as 3 or more and including 4 or more types of macrostructure. For example, the macroporous metal organic matrix may include a first macrostructure region configured for separating components of an analyte composition by an electrokinetic protocol and a second macrostructure region configured for separating components of an analyte composition by chromatography. In another example, the macroporous metal organic matrix may include a first macrostructure region that is an affinity chromatography matrix (i.e., has specific binding moieties) and a second macrostructure region that is a reverse-phase chromatography matrix. Where the macroporous metal organic polymer matrix includes more than one different macrostructure region, the size of each region may vary as desired, the surface area ranging from 0.1 to 5 cm$^2$, such as from 0.5 to 5 cm$^2$, such as 1.0 to 5 cm$^2$, such as 1.5 to 4.5 cm$^2$, such as 2.0 to 4 cm$^2$, such as 2.5 to 3.5 cm$^2$, and including 2 to 3 cm$^2$.

Mass Analyzing Systems Having Macroporous Metal Organic Polymer Matrices for Analyzing Analyte Compositions Aspects of the invention further include systems for practicing the subject methods. In certain embodiments, a system for analysis of an analyte composition is provided, where the system includes one or more macroporous metal organic polymer matrices sampling device configured for applying one or more analyte compositions to the macroporous metal organic polymer matrix and a solvent chamber configured to provide one or more solvents to the macroporous metal organic polymer matrix.

In some embodiments, systems include a sampling device for applying one or more analyte compositions to the macroporous metal organic polymer matrix. The sample device may be any suitable apparatus which allows for the analyte composition to be contacted with the macroporous metal organic polymer matrix. For example, the sampling device may be a syringe, syringe mounted on a pump, a pipet, a piston pipet or a conduit connected to an analyte composition reservoir such as a conduit in fluid communication with a chromatography (e.g., HPLC) system or capillary electrophoresis system. Where the analyte composition is a solid sample (e.g., tissue sample), the sampling device may be a set of tweezers, mechanical clamps or spatula configured for applying the solid sample to the surface of the macroporous metal organic polymer matrix.

Systems of the invention may further include a solvent chamber configured to deliver one or more solvents to the macroporous metal organic polymer matrix. The solvent chamber may be any suitable solvent reservoir that is capable of storing and providing one or more solvents to the macroporous metal organic polymer matrix. The solvent chamber in certain embodiments is a syringe with a preloaded solvent. In other embodiments, the solvent chamber may be a reservoir that is in fluid communication with one or more sources of solvent and may be a single high throughput storage reservoir which can provide solvent as desired for contacting with the macroporous metal organic polymer matrix. Sources of one or more solvents may also be individual vials having a discrete amount of solvent. The source of one or more solvents may also be a reservoir with pre-measured aliquots. The one or more sources may include a single type of solvent or may be capable of providing a plurality of different types of solvents. For example, the source may be capable of storing and providing 2 different solvents or more, such as 3 different solvents or more, such as 5 different solvents or more, and including 10 different solvents or more. Depending on the particular design of the solvent chamber, the chamber may further include one or more inlets for delivering the solvent to the macroporous metal organic polymer matrix. In certain embodiments, systems of the invention include one or more inlets for injecting solvent into the macroporous metal organic polymer matrix.

Certain systems may also include a surface ionization protocol sufficient to produce and expel analyte ions from the macroporous metal organic polymer matrix surface. For example, surface ionization protocols may include, but are not limited to, desorption electrospray (DESI), liquid extraction surface analysis, nano-DESI, laser assisted electrospray ionization, matrix-assisted laser desorption electrospray ionization, laser ablation electrospray ionization (LAESI) including infrared laser assisted desorption electrospray ionization (IR-LADESI) as well as desorption atmospheric pressure photoionization (DAPPI).

Systems of the invention also include an analyte ion analyzer. Any convenient analyte ion analyzer may be employed so long as it is capable of characterizing analyte ions, such as for example a mass analyzer which measures the mass-to-charge ratio of analyte ions. In certain embodiments, the analyte ion analyzer is a mass spectrometer. Mass spectrometer systems may be any convenient mass spectrometry system which includes a mass analyzer for separating ions, and a detector that detects the ions. In certain cases, the mass spectrometer may be a "tandem" mass spectrometer that is capable of isolating precursor ions, fragmenting the precursor ions, and analyzing the fragmented precursor ions and may include but are not limited to mass spectrometer systems described in U.S. Pat. Nos. 7,534,996, 7,531,793, 7,507,953, 7,145,133, 7,229,834 and 6,924,478, the disclosures of which are herein incorporated by reference. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap.

Any of a variety of different mass analyzers may be employed, including but not limited to time of flight (TOF), Fourier transform ion cyclotron resonance (FTICR), quadrupole ion trap, rectilinear ion trap, cylindrical ion trap, ion cyclotron resonance trap and orbittrap, quadrupole or double focusing magnetic electric sector mass analyzers, or any hybrid thereof.

Systems of the invention may also include analytical separation devices such as an ion-mobility spectrometer, liquid chromatograph (LC), including a high performance liquid chromatograph (HPLC), a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the analyte composition may be applied to the LC system by employing a nano- or micropump in certain embodiments.

Aspects of the invention may further include high-throughput and computer controlled systems for practicing methods of the invention, where the systems further include one or more computers for automation or semi-automation of a system for practicing methods of the invention. In certain embodiments, systems include a computer having a computer readable storage medium with a computer program stored thereon, where the computer program when loaded on the computer includes algorithm for contacting one or more analyte compositions with the macroporous metal organic polymer matrix, algorithm for applying a voltage to the macroporous metal organic polymer matrix sufficient to produce and expel analyte ions from the macroporous metal organic matrix, algorithm for applying a source of ionization to the macroporous metal organic polymer matrix surface sufficient to produce and expel analyte ions from the surface of the macroporous metal organic polymer matrix and instructions for analyzing the analytes ions with the mass analyzer.

In embodiments of the invention, the system includes an input module, a processing module and an output module. In some embodiments, the subject systems may include an input module such that parameters or information about each of the solvent, analyte compositions, etc. may be inputted into the computer. The processing module includes memory having a plurality of instructions for performing the steps of the subject methods. After the processing module has performed one or more of the steps of the subject methods, an output module communicates the results (e.g., characterization of the one or more components of the analyte composition) to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing one or more of the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Pert, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The processor may also have access to a communication channel to communicate with a user at a remote location. By remote location is meant the user is not directly in contact with the system and relays input information to an input manager from an external device, such as a a computer connected to a Wide Area Network ("WAN"), telephone network, satellite network, or any other suitable communication channel, including a mobile telephone (i.e, smartphone). In these embodiments, input manager receives information, e.g., coagulation activity data, chemical makeup data, molecular structure data, etc., from a user e.g., over the Internet, telephone or satellite network. Input manager processes and forwards this information to the processing module. These functions are performed using any convenient technique.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g, over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Sun Solaris, Linux, OS/400, Compaq Tru64 Unix, SGI IRIX, Siemens Reliant Unix, and others.

Kits

Also provided are kits, where kits at least include one or more, e.g., a plurality of, the subject macroporous metal organic polymer matrices, as described above. Kits may further include other components for practicing the subject methods, such as sampling or application devices (e.g., syringes or pipets) or solvents to wash the macroporous metal organic polymer matrix or to use during methods of the invention.

In some embodiments, compositions having an amount of one or more bioactive compounds (e.g., peptides, polymers, proteins, enzymes, antibodies, polysaccharides, cellular components, whole cells, microorganisms, etc.) in combination with the subject macroporous metal organic polymer matrix may be provided as packaged kit. In certain embodiments, kits include one or more protease enzymes such as a serine protease, threonine protease, cysteine protease, aspartate protease, glutamic acid protease and metalloprotease, acid protease and alkaline protease. For example, proteases of interest may include, but are not limited to, trypsin, chymotrypsin, pepsin, papain, bromelain, serratia peptidase, subtilisin, elastases, dipeptidase E, penicillin G acylase, DmpA aminopeptidase, prolyl oligopeptidase, D-Ala-D-Ala peptidase C, signal peptidase, cytomegalovirus assembling, Lon-A peptidase, peptidase C1p, E. coli phage ME endosialidase, nucleoporin, lactoferrin, murein tetrapeptidase LD-carboxypeptidase, rhomboid-1, fecal elastase, archaean proteasome, ornithine acetyltransferase, TEV protease, amidophosphoribosyltransferase, gamma-glutamyl hydrolase, hedgehog protein, caspase-1, separase, adenain, pyroglutamyl-peptidase, sortase A, dipeptidyl-peptidase VI, DeSI-1 peptidase, Beta-secretase 1, Cathepsin D, Cathepsin E, Chymosin, Napsin, Nepenthesin, calpain, plasmepsin, presenilin, renin, disintegrin and metalloproteinases, ADAM proteins, as well as other types of exopeptidases and endopeptidases, In certain embodiments, kits include one or more macroporous metal organic polymer matrices having preloaded one or more active compounds. In other embodiments kits include one or more macroporous metal organic polymer matrices having preloaded analye composition.

In addition, kits may also include instructions for how to use the subject macroporous metal organic polymer matrix, where the instructions may include information about to how apply a sample to the macroporous metal organic polymer matrix, how to dope (e.g., affix to the surface or within the pores) the macroporous metal organic polymer matrix with one or more active compounds such as but not limited to polymers, peptides, proteins, enzymes, antibodies, polysaccharides, cellular components, whole cells and microorganisms, how to wash and reuse the subject macroporous metal organic polymer matrix, protocols for separating or concentrating one or more components of an analyte composition on the macroporous metal organic polymer matrix, and record keeping devices for executing the subject methods. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

Macroporous metal organic polymer matrices and methods for using the macroporous metal organic polymer matrices according to the present disclosure find use in the analysis of one or more components in an analyte composition, such as a biological sample or products formed through chemical reaction, biochemical reaction or metabolites from cells or microorganisms. Likewise, the subject macroporous metal organic polymer matrix find use in applications for separating or concentrating one or more components of an analyte composition prior to analysis.

In certain examples, macroporous metal organic polymer matrices find use as emitters in mass spectrometry, such as for example ambient ionization mass spectrometry. Furthermore, the subject macroporous metal organic polymer matrices and methods of the invention find use in protocols that would benefit from analysis which requires no sample preparation of work-up prior to analysis.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Materials and Chemicals Methyltrimethoxysilane (MTMS) and dimethyldimethoxysilane (DMDMS) were purchased from Sigma-Aldrich Corporation, St. Louis, Mo., and were used without further purification. Polyethylene glycol (PEG) with molecular weights of 10,000; 4,000; and 1,001, cetyl trimethylammonium chloride (CTAC), urea, hydrochloric acid, aspartic acid, ascorbic acid, benzoic acid, and p-methoxybenzoic acid were purchased from Sigma-Aldrich Corporation and used without further purification. Saxitoxin and aconitine were used as provided.

Polymerization. The reaction stock solution was prepared by adding 500 μL of MTMS and 225 μL DMDMS to 275 μL of 1.47 mM aqueous CTAC and 200 μL distilled water. This solution was vigorously stirred at room temperature for approximately 60 minutes to afford an opaque solution. A volume of 600 μL of the resulting reaction solution was cast into a well of a 24-well polystyrene multiculture plate (CoStar). A lid was placed onto the plate, then placed into an 80° C. oven for approximately 12 hours of curing time. The resulting organosiloxane polymer (OSX) material was transparent, colorless, and flexible. Subsequently the lid of the plate was removed to allow evaporation of any remaining liquid by-product and placed back into the oven for 4 hours.

Porosity Test. The porosity of the material was demonstrated by placing the circular OSX material into an aqueous solution of rhodamine dye overnight, which was followed with rinsing with water and sonication in distilled water for 1.5 hours. FIG. 1 shows the OSX material after immersion in the dye solution and after sonication in water.

Example 2

Figure 2:
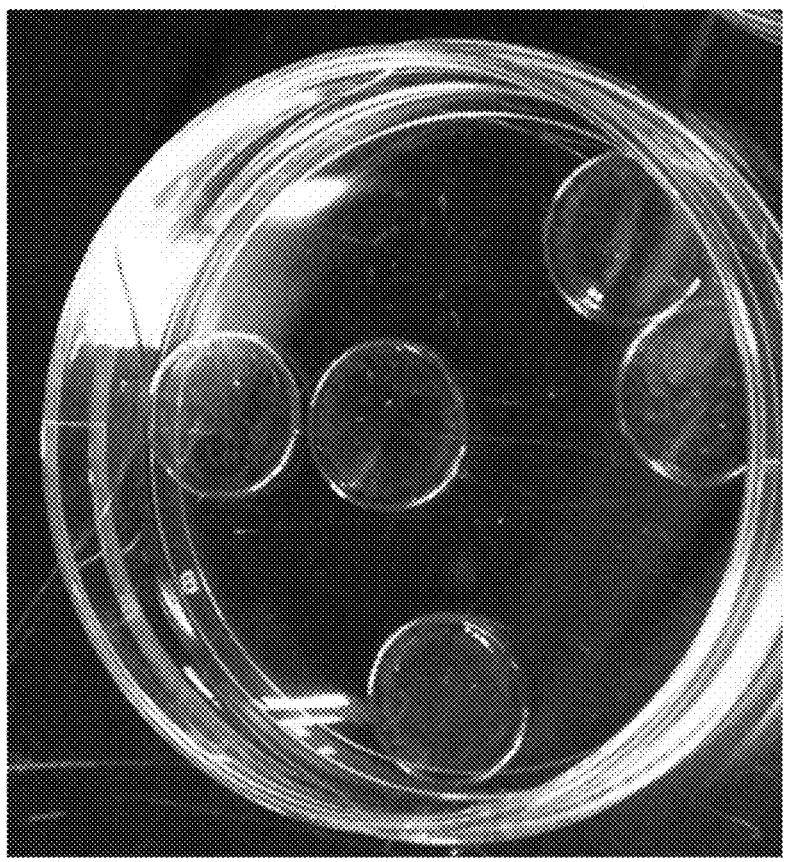
FIG. 2 shows an example of a transparent, colorless and flexible dye cast according to certain embodiments.

Polymerization. The reaction stock solution was prepared by adding 300 μL of MTMS to 50 μL of 11.4 mM polyethylene glycol, MW 10,000 (PEG-10) in 0.12 N HCl. This solution was vigorously stirred at room temperature for approximately 65 minutes to afford colorless, transparent solution. A volume of 20 µL of the resulting reaction solution was added each well of the lid of a 96-well polystyrene multiculture plate (Beckton-Dickinson) and placed into an 65° C. oven for approximately 4 days. The resulting casted OSX material was transparent, colorless, and flexible (FIG. 2).

Figure 3:
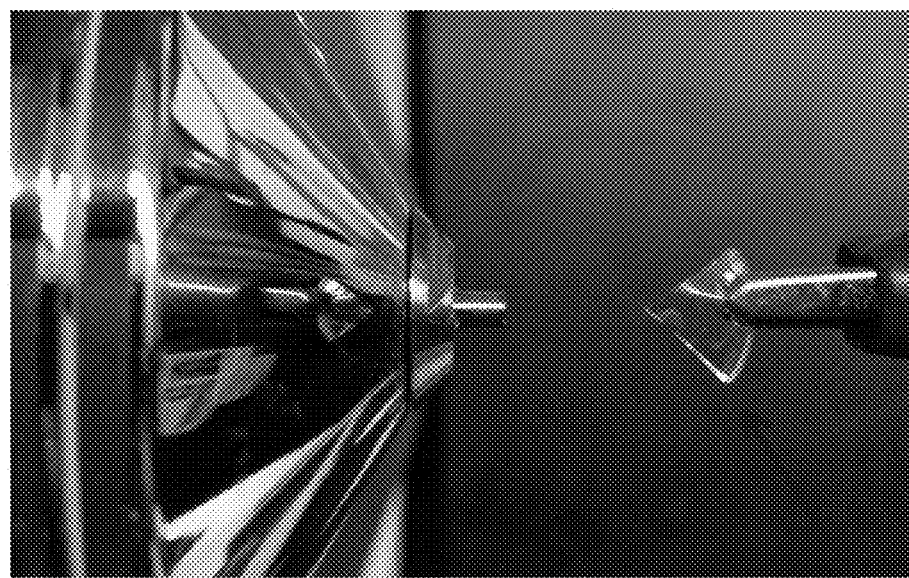
FIG. 3 shows an example where the tip of a triangular-shaped organosiloxane polymer matrix cut with conventional scissors is positioned at the inlet of the mass spectrometer capillary according to certain embodiments.
Figure 3:

Instrumentation. A Thermo Scientific LTQ-Orbitrap XL mass spectrometer was used to carry out the mass spectrometry (MS) experiments. A DC voltage ranging from 2 kV to 5 kV was applied to the organosiloxane (OSX) material wetted with 5 to 10 µL methanol. The vertex/tip of the OSX material was aligned directly in front of the heated capillary of the MS nozzle. FIG. 3 shows an example of the tip of a triangular-shaped OSX material placed at a distance of approximately 1-2 cm from the inlet of the MS capillary. Conventional scissors were used to cut a triangular piece of a round OSX material.

Figure 4:
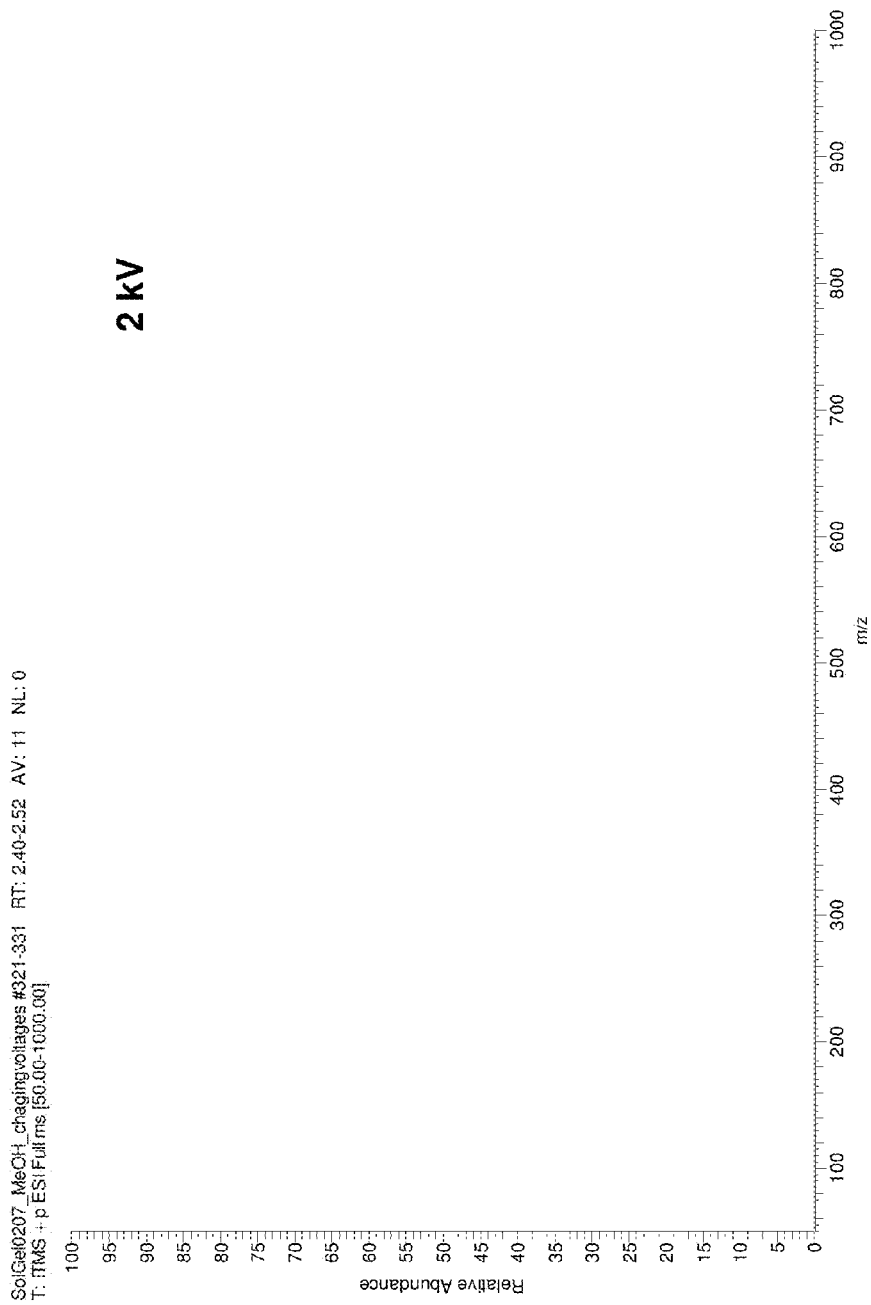
FIG. 4 shows the effect of applied voltage on a half-circle shaped organosiloxane polymer matrix material in the shape of a planar half circle on spray ionization according to certain embodiments.
Figure 4:
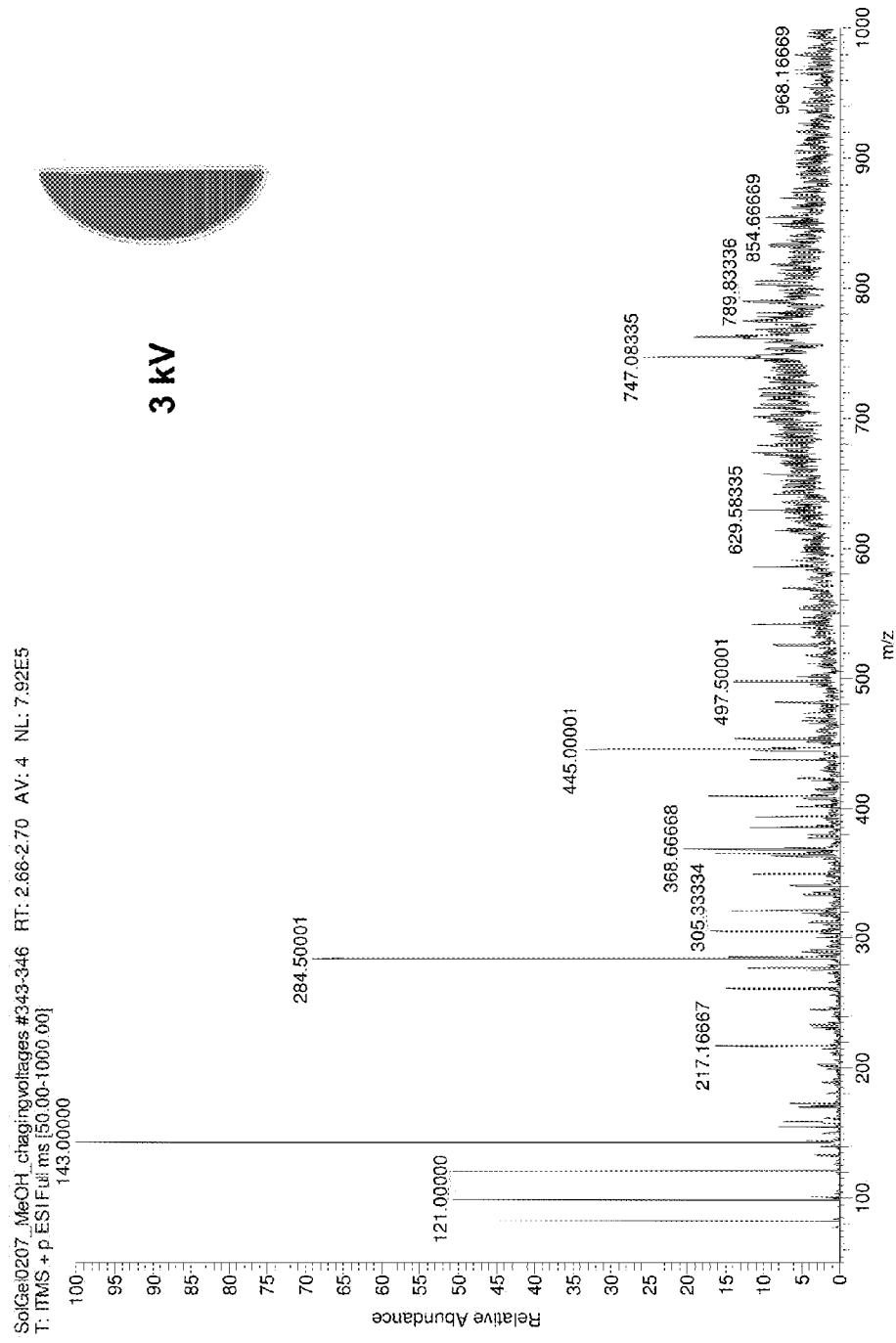
Figure 4:
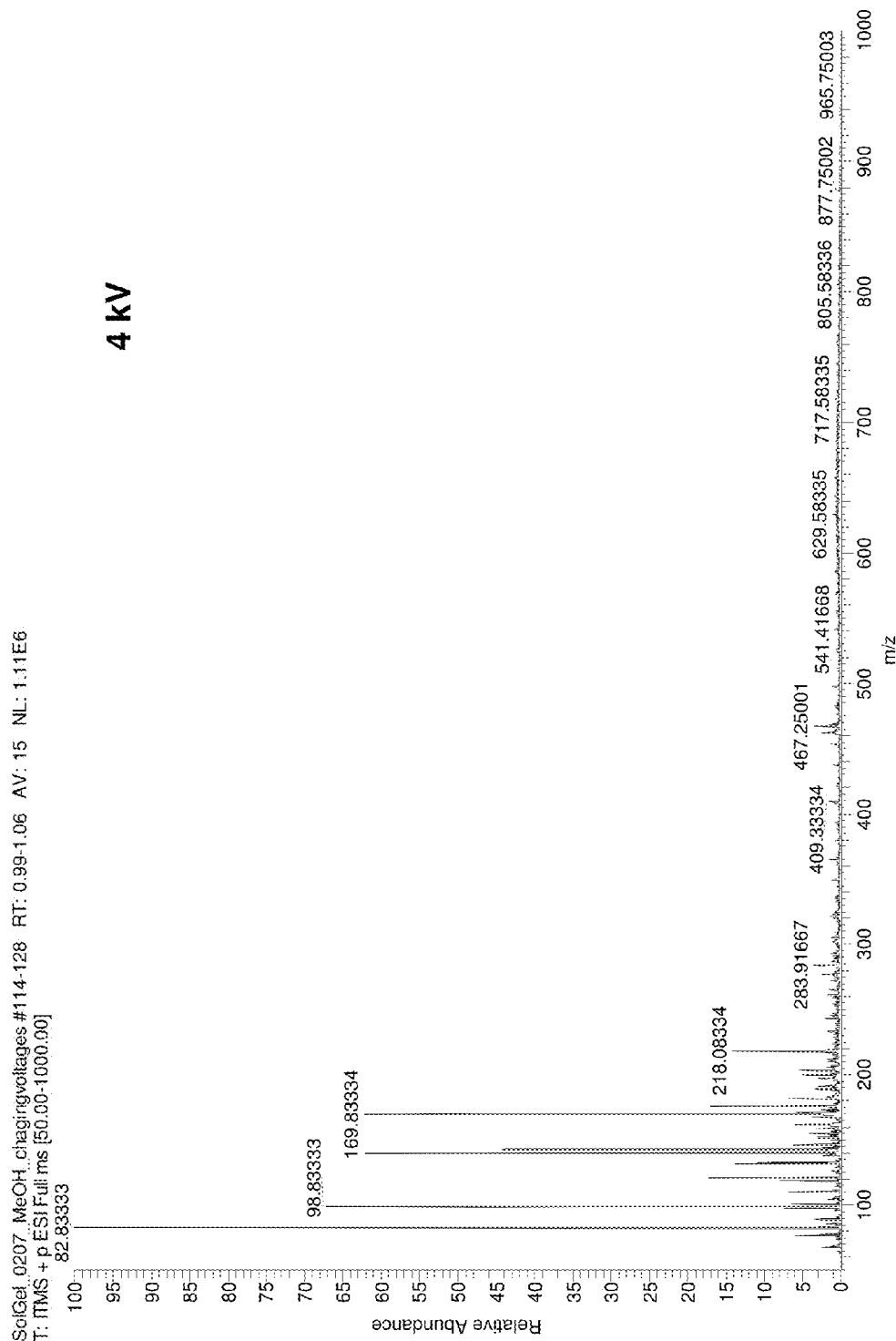
Figure 4:
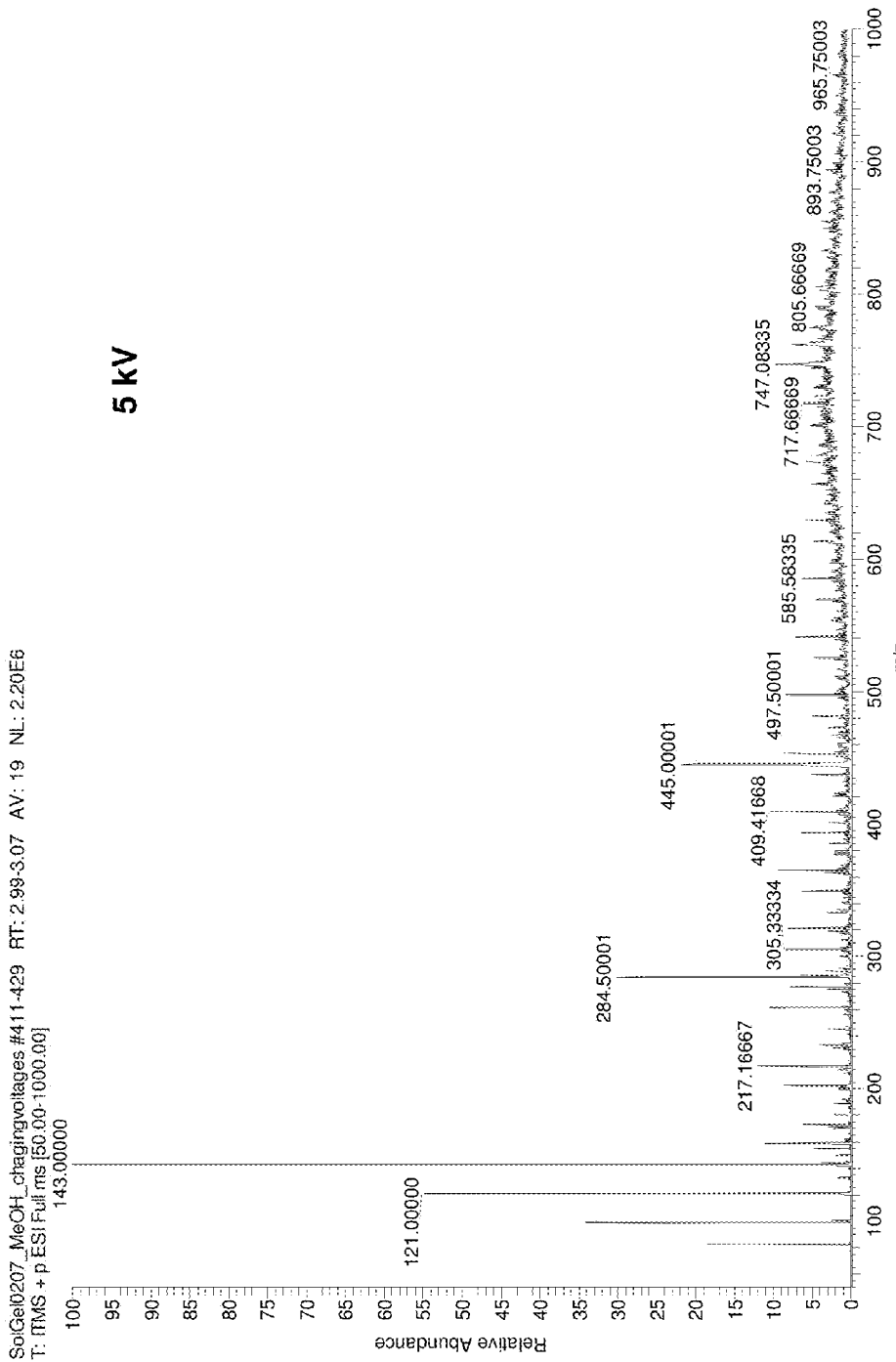
Figure 5:
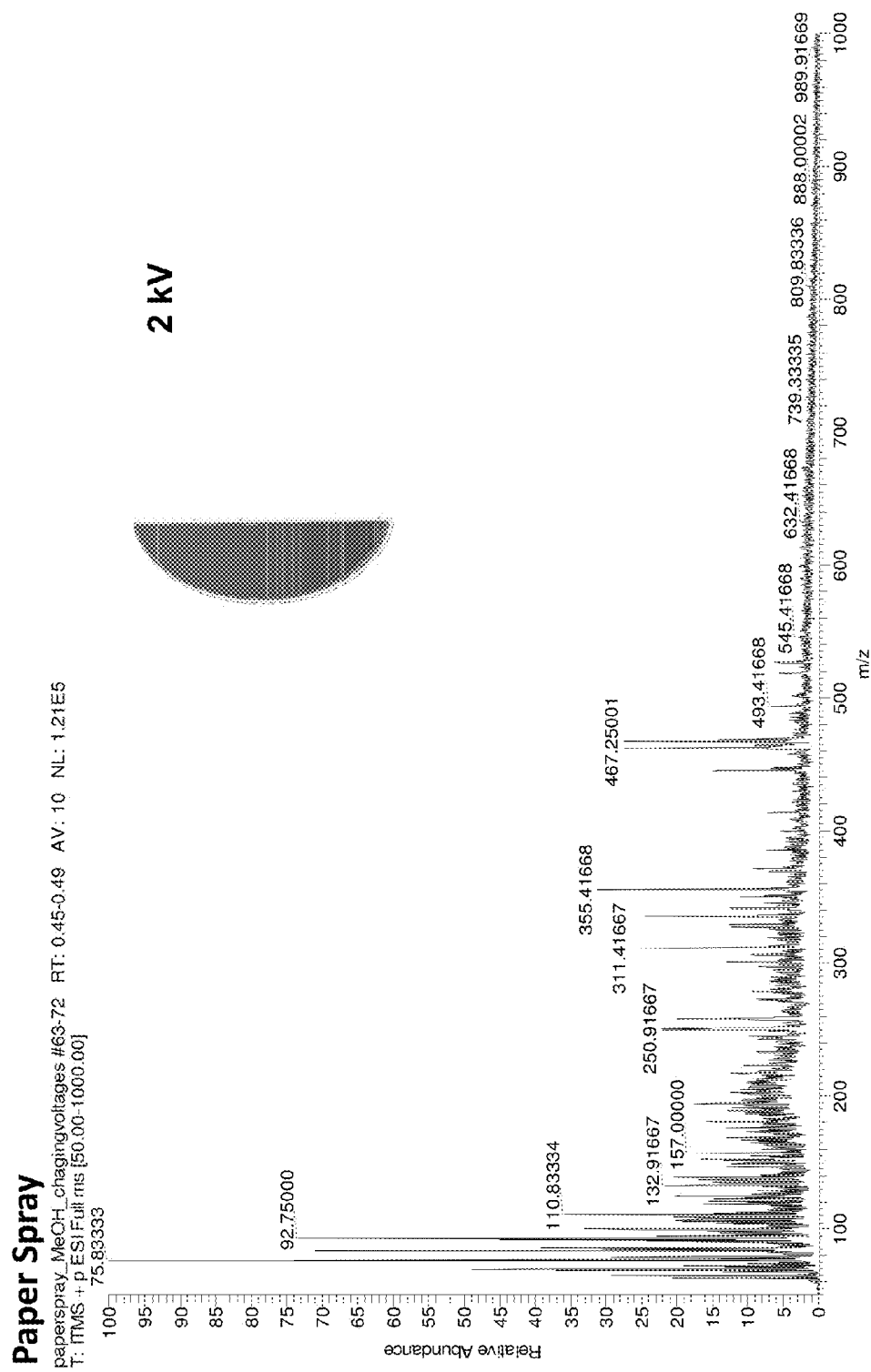
FIG. 5 shows a comparison of applied voltage on a half-circle shaped organosiloxane polymer matrix and cellulose paper according to certain embodiments.
Figure 5:
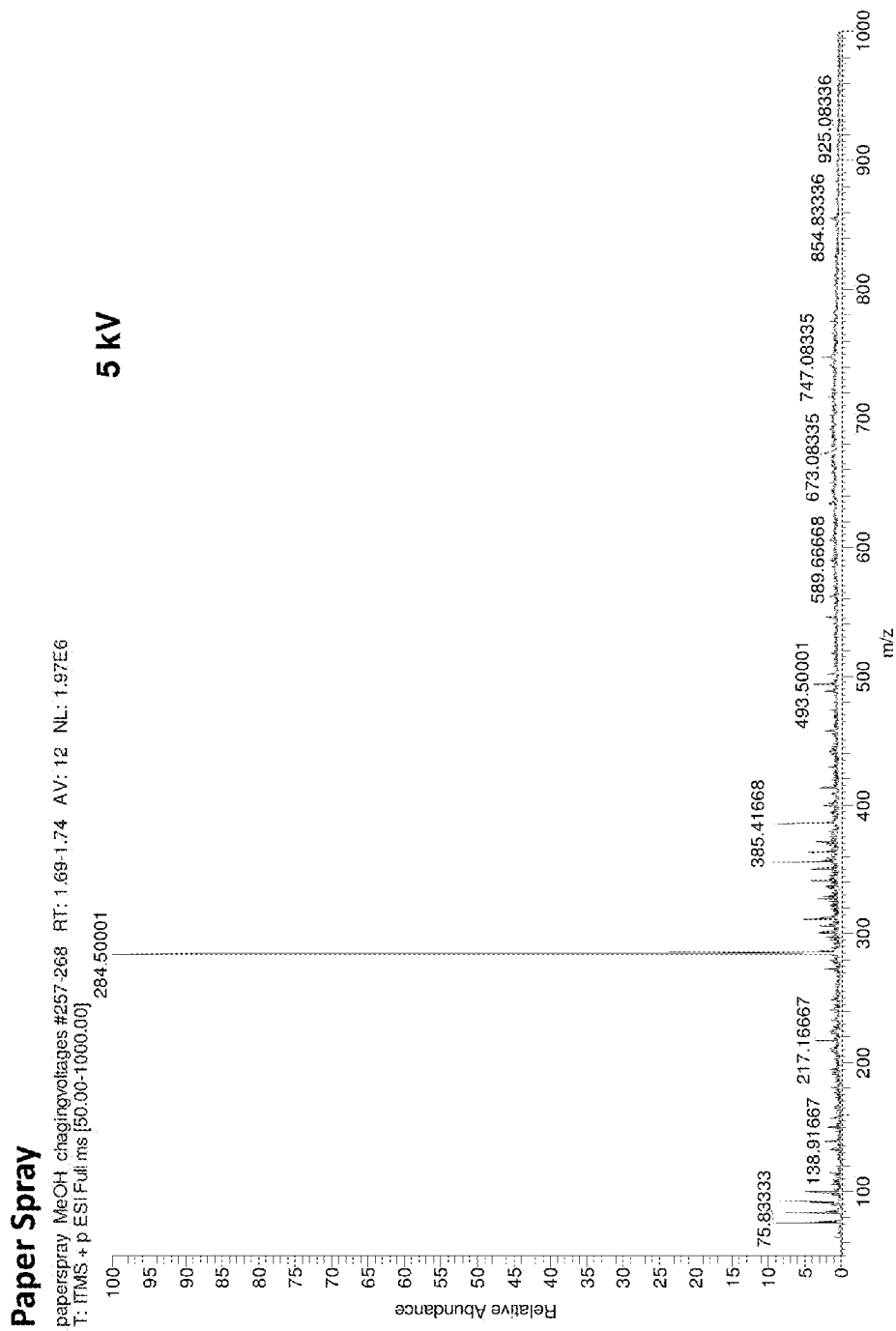
Figure 5:
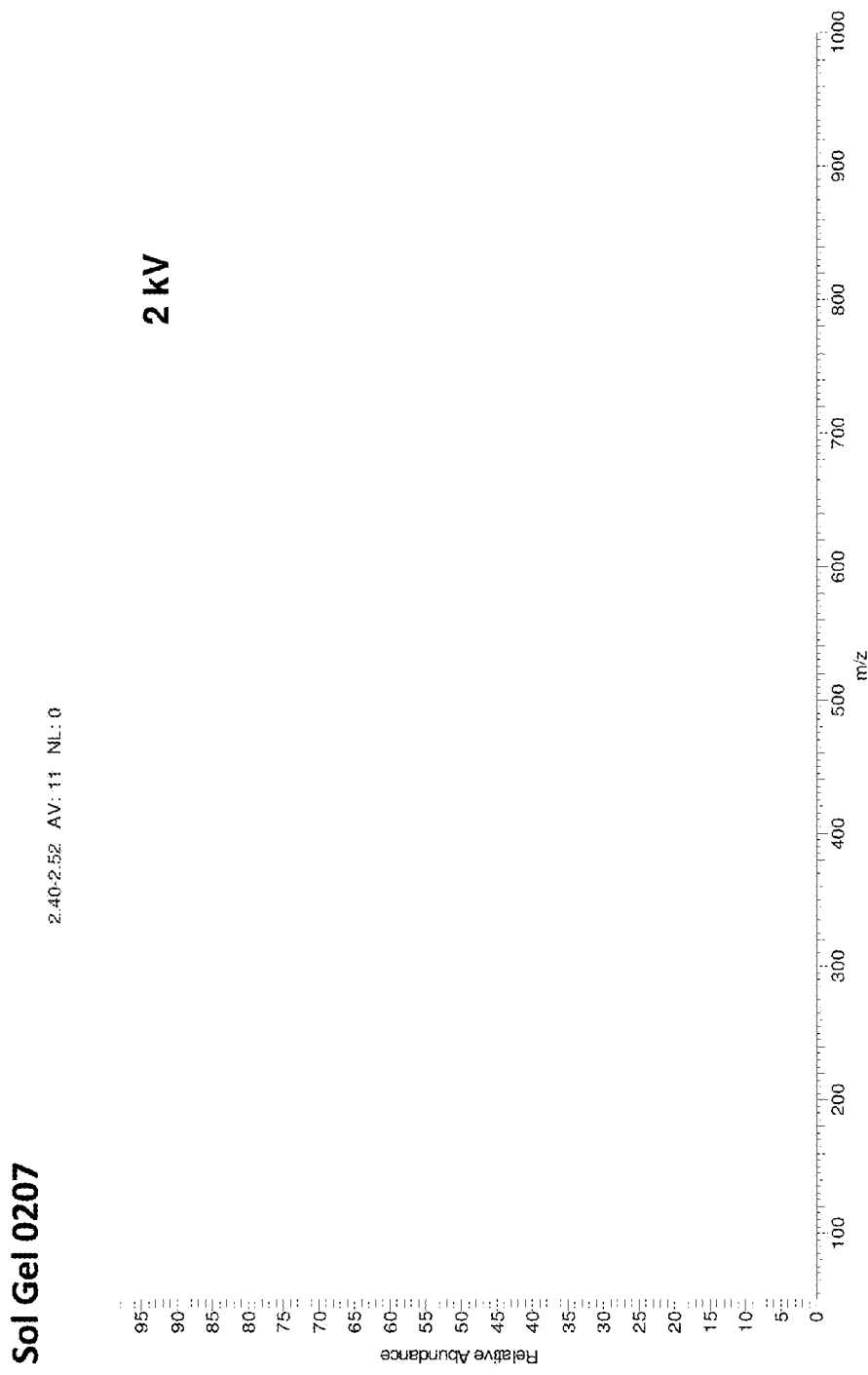
Figure 5:
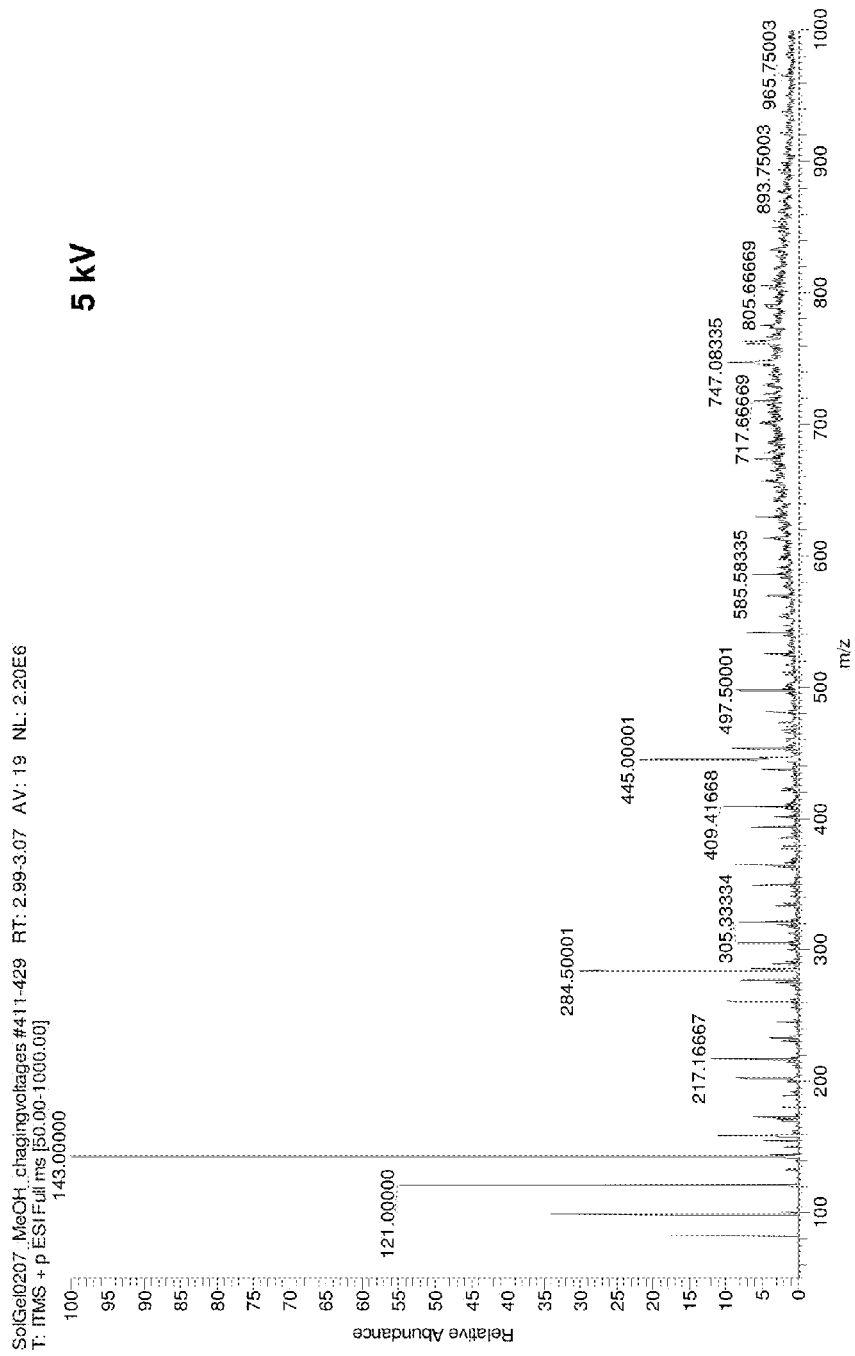

FIG. 4 shows the effect of applied voltage on the OSX material on spray ionization. The optimal applied voltage range is between 3 kV and 5 kV. Methanol was used as the solvent and the OSX material was shaped as a half moon with a thickness of approximately 1 mm and the longest length of 0.8 cm. FIG. 5 shows a comparison of paper and OSX as a function of applied voltage.

Example 3

Figure 6:
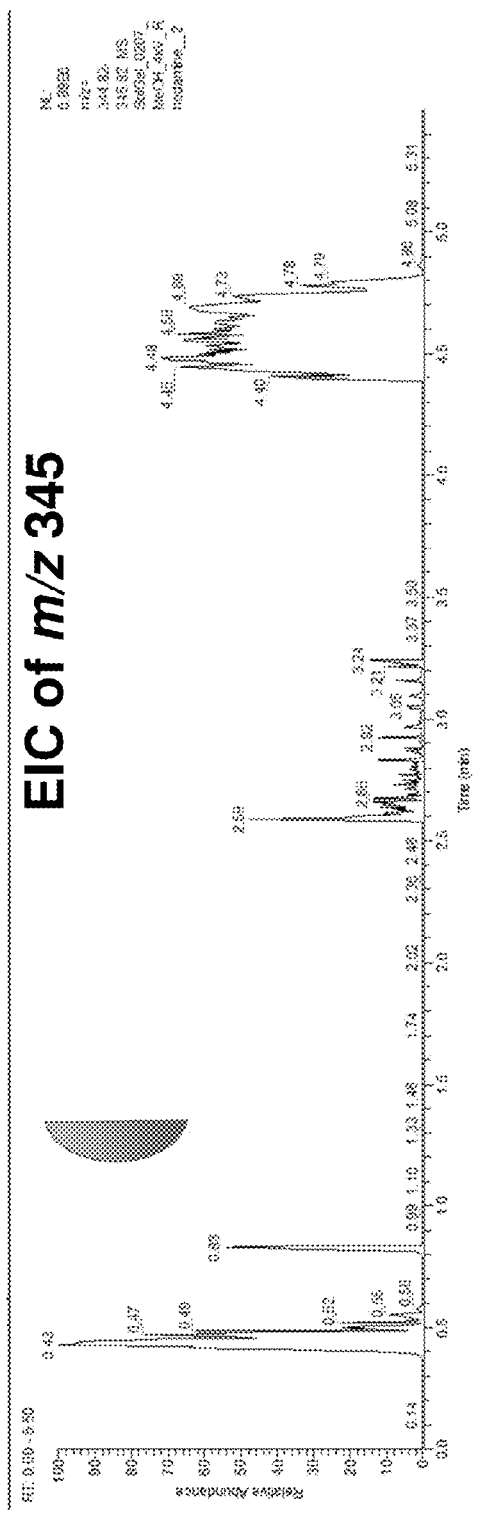
FIG. 6 shows an example of spectra taken employing an organosiloxane polymer matrix according to certain embodiments.

The OSX material was prepared and used as described in Example 2. A mixture of Rhodamine 123 in methanol was used as the analyte. A volume of 5 µL of the Rhodamine 123 solution was added as a droplet to the end of the OSX material (half moon shaped cut from a round piece using conventional scissors) furthest from the inlet of the heated capillary of the MS. Spray was achieved using 10 µL of methanol to wet the OSX material prior to the placement of the Rhodamine solution onto the OSX material surface. An applied voltage of 4 kV was used as shown in FIG. 6 where the top spectrum shows the total ion count during the 6-min data acquisition. The bottom spectrum shows the 345.33 peak ascribed to Rhodamine 123.

Example 4

Figure 7:
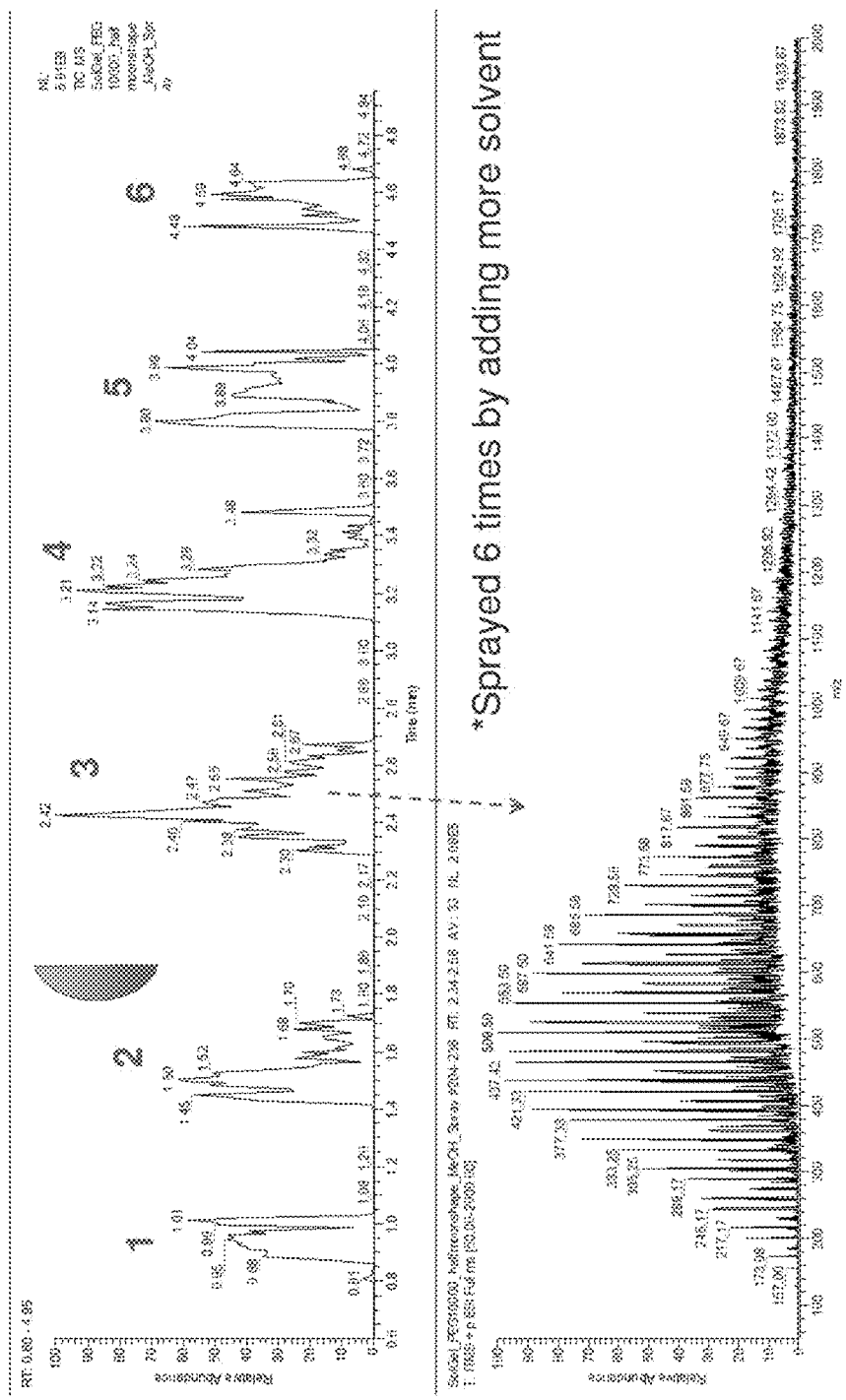
FIG. 7 shows an example of spectra taken during a 6-repeat ion spray employing a half-circle shaped organosiloxane polymer matrix according to certain embodiments.

The OSX material was prepared and used as described in Example 2. A volume of 10 µL of methanol was used to wet the half-moon-shaped OSX material prior to spray ionization with an applied voltage of 5 kV. The half-moon-shaped was cut from a round OSX piece using conventional scissors. Spray was achieved 6 times as shown in FIG. 7, which required the addition of more methanol to keep the OSX material wetted during the experiment. The total volume of methanol used during the run was 30 µL.

Example 5

Figure 8:
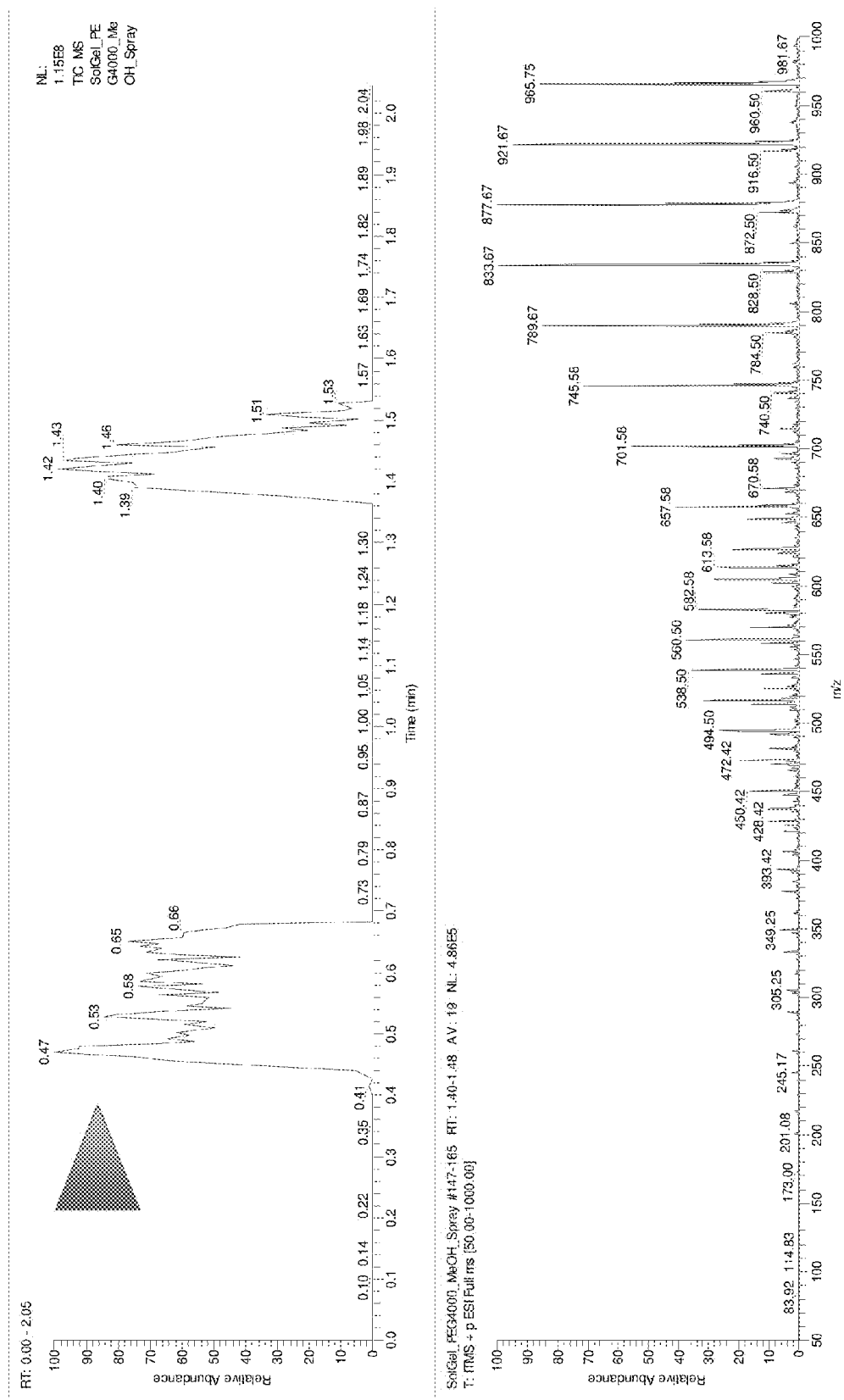
FIG. 8 shows another example of spectra taken employing a triangular organosiloxane polymer matrix according to certain embodiments.

The OSX material was prepared and used as described in Example 2 but with the use of PEG with molecular weight 4,000 instead of PEG with molecular weight 10,000. FIG. 8 illustrates the use of a triangular-shaped OSX polymer (cut from a round piece using conventional scissors) prepared with PEG-4000 with an applied voltage of 5 kV and 10 µL of methanol as the spray solvent. The top spectrum is the total ion count during the approximately 2-min run while the bottom spectrum is a representation of the mass spectrum during a portion of the run.

Example 6

Figure 9:
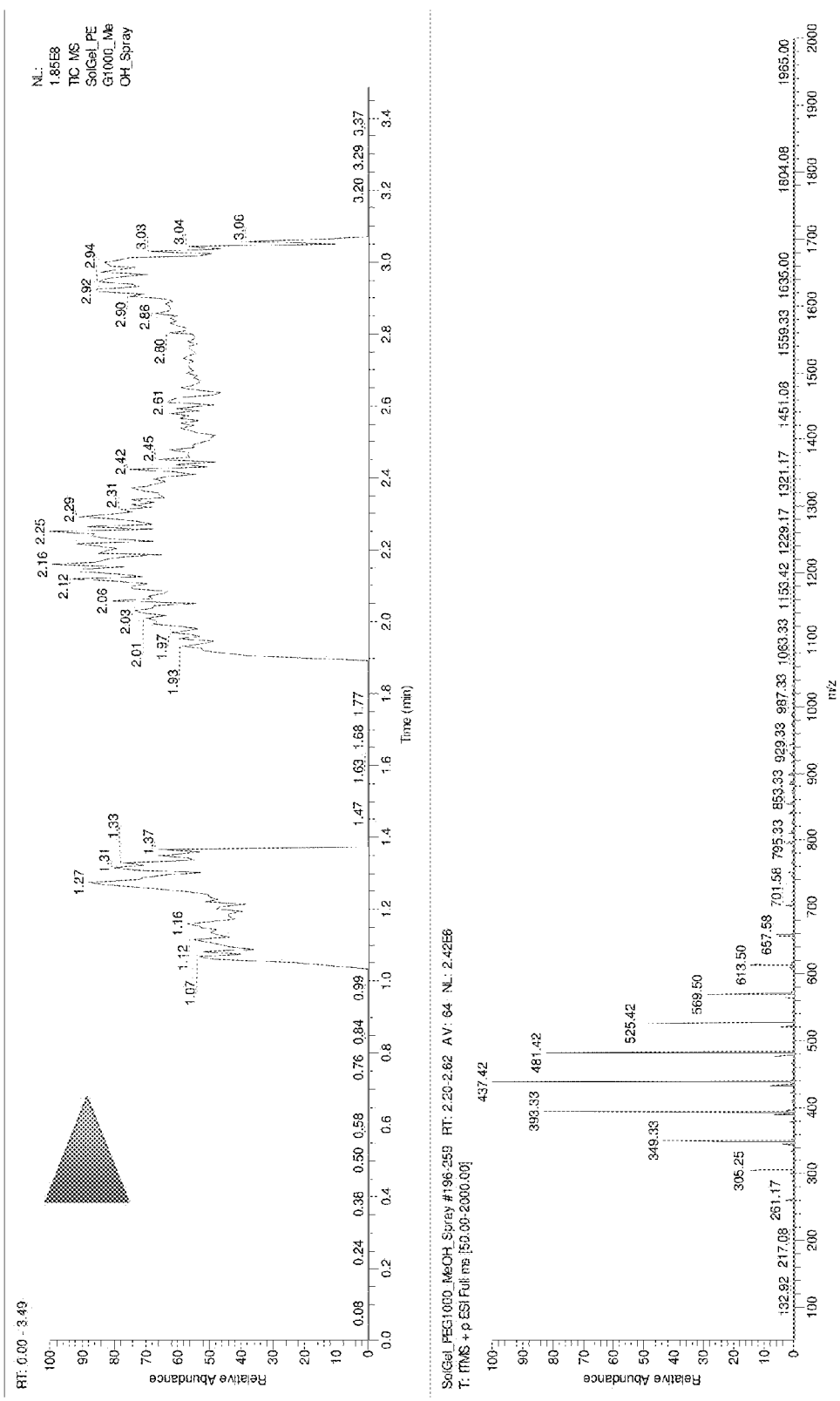
FIG. 9 shows another example of spectra taken employing a triangular organosiloxane polymer matrix according to certain embodiments.

The OSX material was prepared and used as described in Example 2 but with the use of PEG with molecular weight 1,000 instead of PEG with molecular weight 10,000. FIG. 9 illustrates the use of a triangular-shaped OSX polymer prepared with PEG-1000 with an applied voltage of 5 kV and 10 µL of methanol as the spray solvent. The triangle shape was cut from a round piece of OSX material utilizing an ordinary pair of scissors. The top spectrum is the total ion count during the approximately 3.5-min run while the bottom spectrum is a representation of the mass spectrum during a portion of the run.

Example 7

Polymerization. The reaction stock solution was prepared by adding 500 µL of MTMS and 225 µL DMDMS to 275 µL of 4.5 mM aqueous CTAC, 10 µL 6.0 M aqueous urea, and 325 µL of 0.12 N HCl. This solution was vigorously stirred at room temperature for approximately 60 minutes to afford colorless, transparent solution. Volumes of 200 µL and 400 µL of the resulting reaction solution was used to fill the wells of a 12-well polystyrene multiculture plate (Beckton-Dickinson) and placed into an 80° C. oven for approximately 7 hours. The resulting OSX material was transparent, colorless, and flexible.

Figure 10:
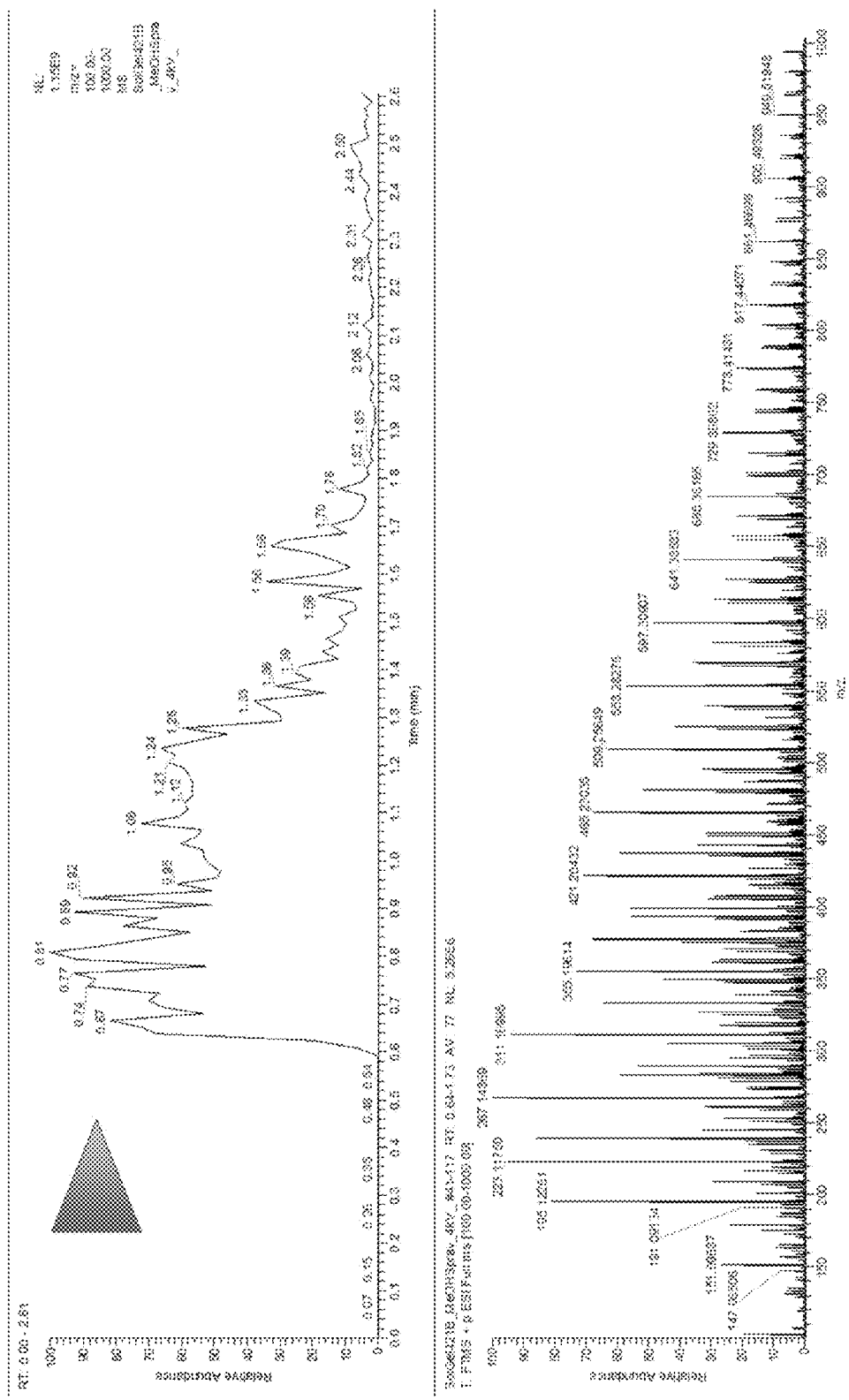
FIG. 10 shows an example of spectra taken employing a triangular organosiloxane polymer matrix demonstrating spray ionization stability over a period of time according to certain embodiments.

Instrumentation. A Thermo Scientific LTQ-Orbitrap XL mass spectrometer was used to carry out the mass spectrometry (MS) experiments. A DC voltage of 4 kV was applied to the organosiloxane (OSX) material wetted with 10 µL methanol. The vertex/tip of the OSX material was aligned directly in front of the heated capillary of the MS nozzle. FIG. 10 illustrates the spray ionization stability over a period of 2.6 min. The top spectrum in this figure is a recording of the total ion count during this run period. The bottom spectrum is a recording of the masses detected during a portion of this run.

Example 8

Figure 11:
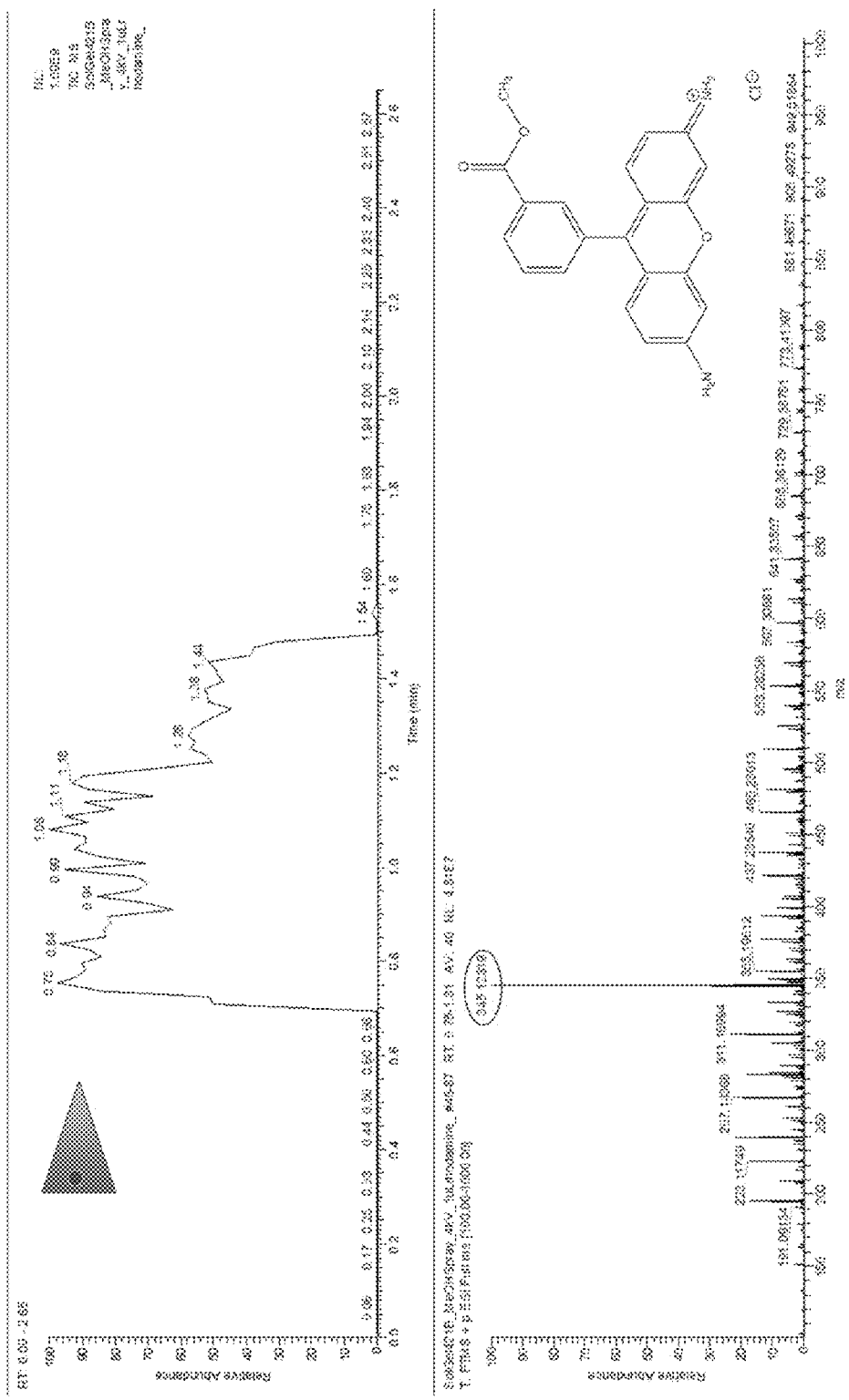
FIG. 11 shows an example of spectra demonstrating analysis of rhodamine taken employing a triangular organosiloxane polymer matrix according to certain embodiments.

The OSX material was prepared and used as described in Example 7. FIG. 11 shows the spray ionization results using a solution of Rhodamine 123 in methanol as the test analyte. 1 µL droplet of Rhodamine 123 solution was placed at the end opposite the OSX vertex/tip. The OSX was wetted with 10 µL of methanol and an applied voltage of 4 kV was used in this experiment. The top spectrum in FIG. 11 shows the total ion count during a 2.6-min run. The bottom spectrum is the mass spectrum showing the peak for Rhodamine 123 at mass 345.123.

Example 9

Figure 12:
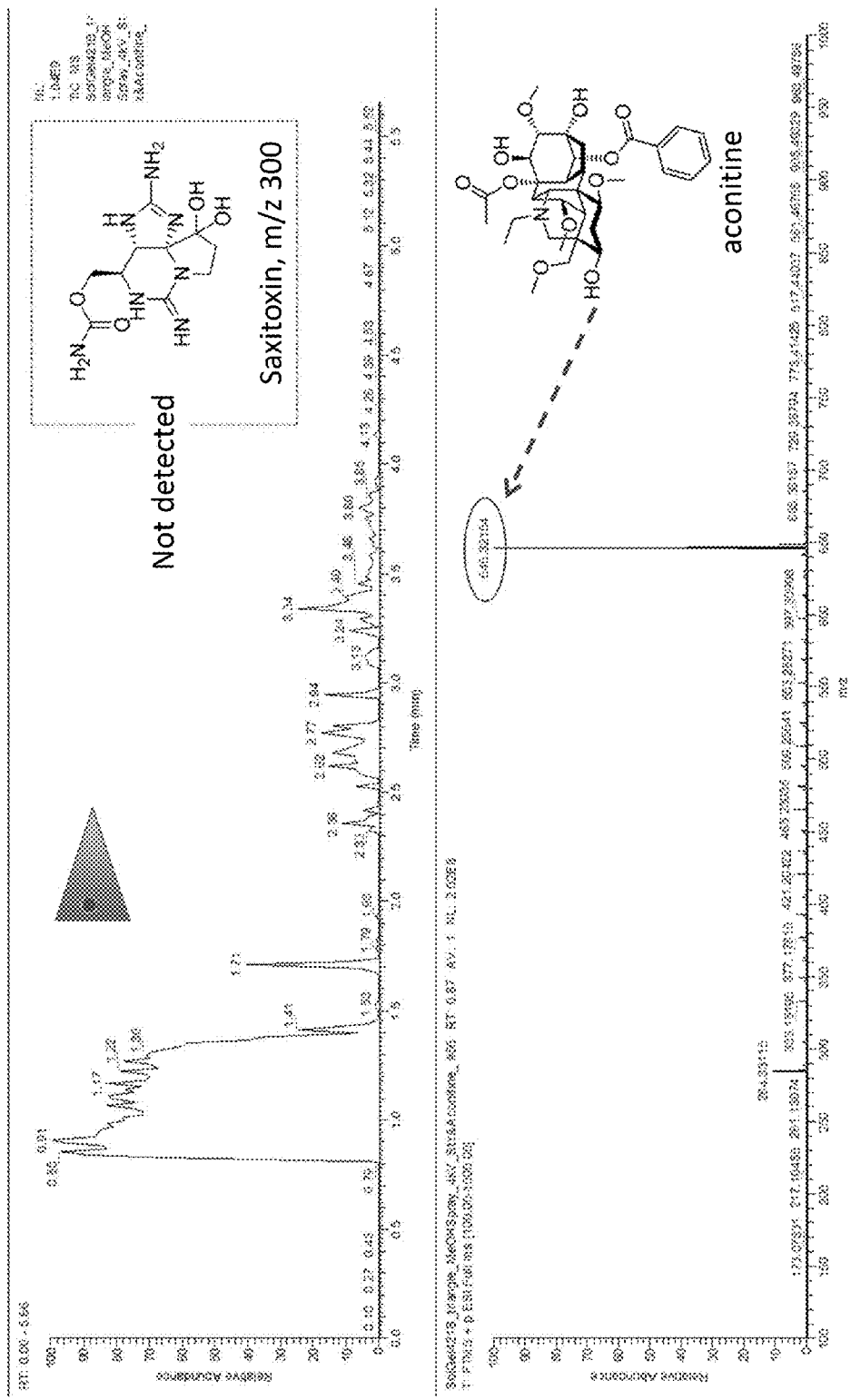
FIG. 12 shows an example of spectra demonstrating analysis of saxitoxin and aconitine taken employing an triangular organosiloxane polymer matrix according to certain embodiments.

The OSX material was prepared and used as described in Example 7. FIG. 12 shows the analysis/detection of two neurotoxins, saxitoxin and aconitine, prepared in water. The triangular-shaped OSX was wetted with 10 µL of methanol and 4 kV was applied during the spray ionization. Saxitoxin with a mass-to-charge ratio (m/z) of 300 was not detected because of degradation during the storage of the solution. Aconitine with m/z 646 was detected during the 5.5-min run.

Example 10

Figure 13:
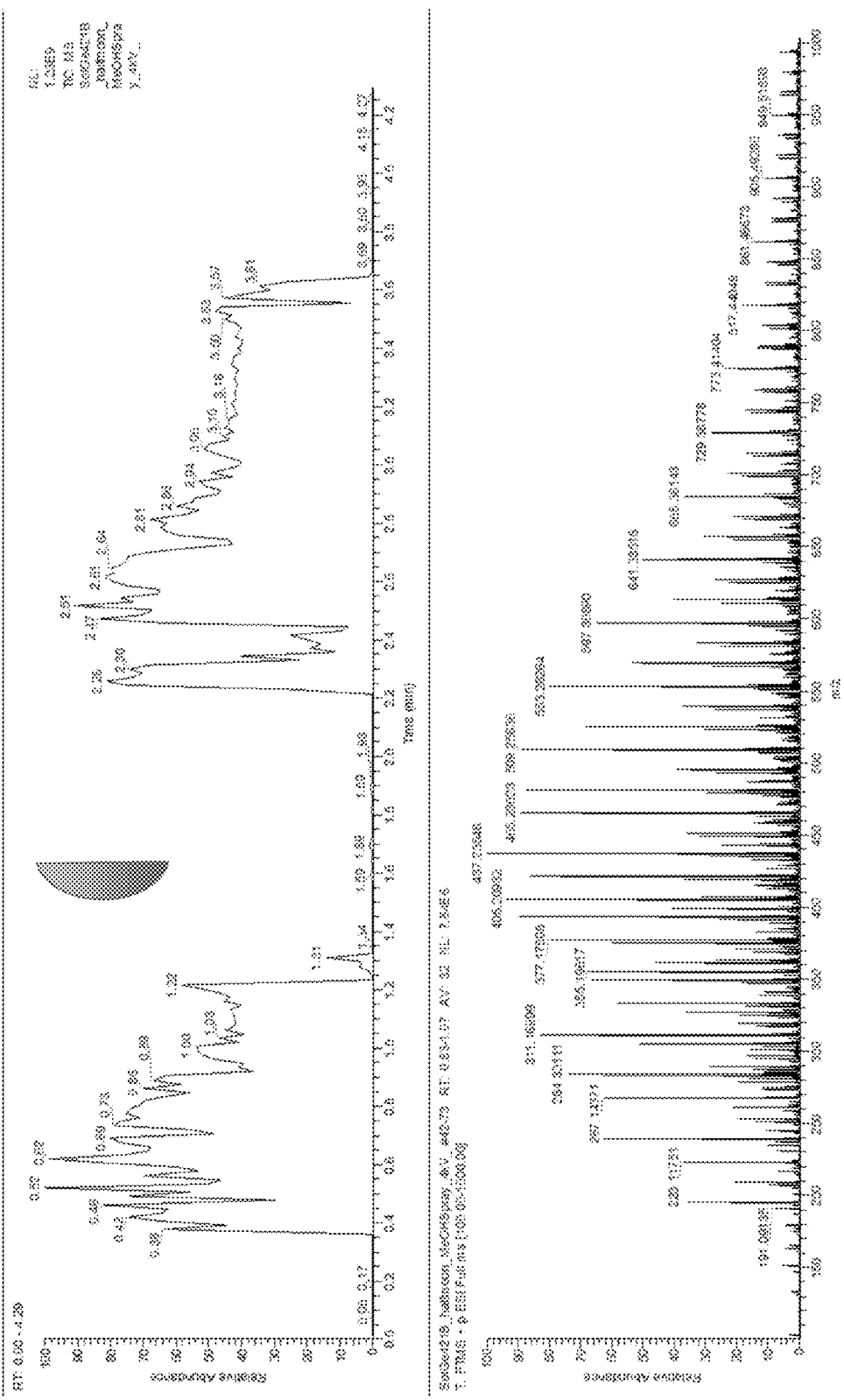
FIG. 13 shows an example of spectra taken employing a half circle-shaped organosiloxane polymer matrix demonstrating spray ionization stability over a period of time according to certain embodiments.
Figure 14:
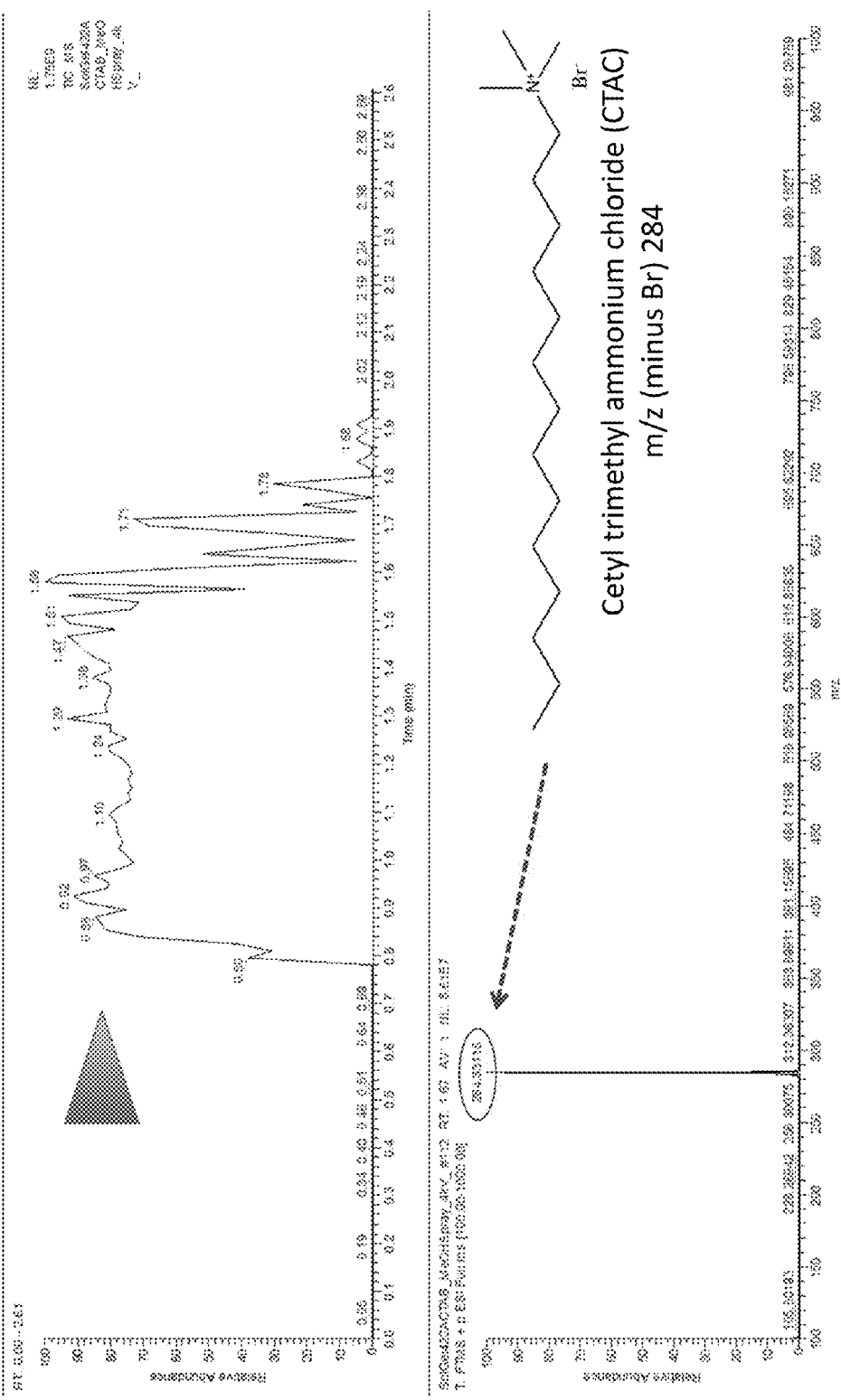
FIG. 14 shows an example of spectra taken employing a triangular organosiloxane polymer matrix demonstrating spray ionization stability over a period of time according to certain embodiments.
Figure 15:
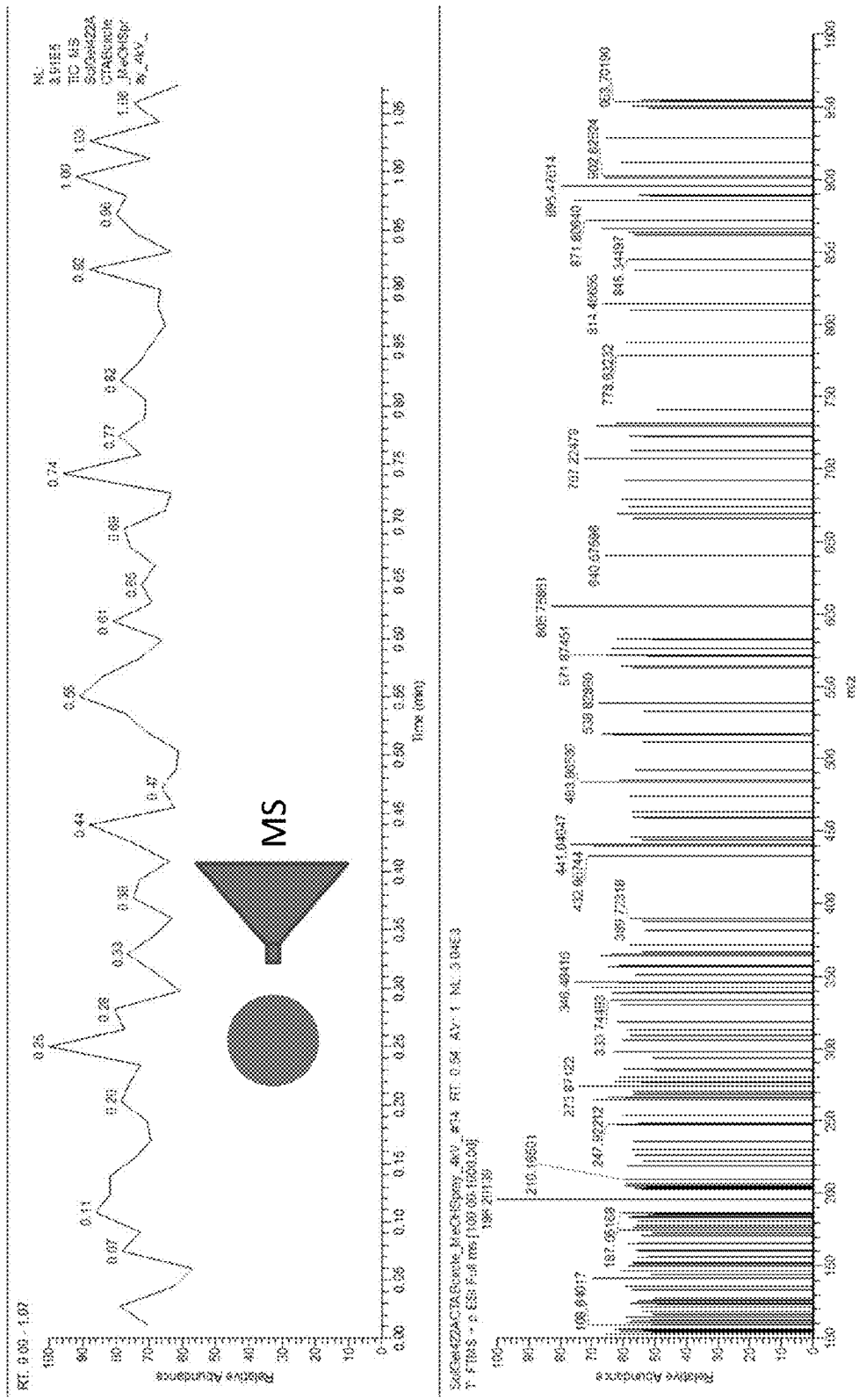
FIG. 15 shows an example of spectra taken employing a circular organosiloxane polymer matrix having no vertices according to certain embodiments.
Figure 16:
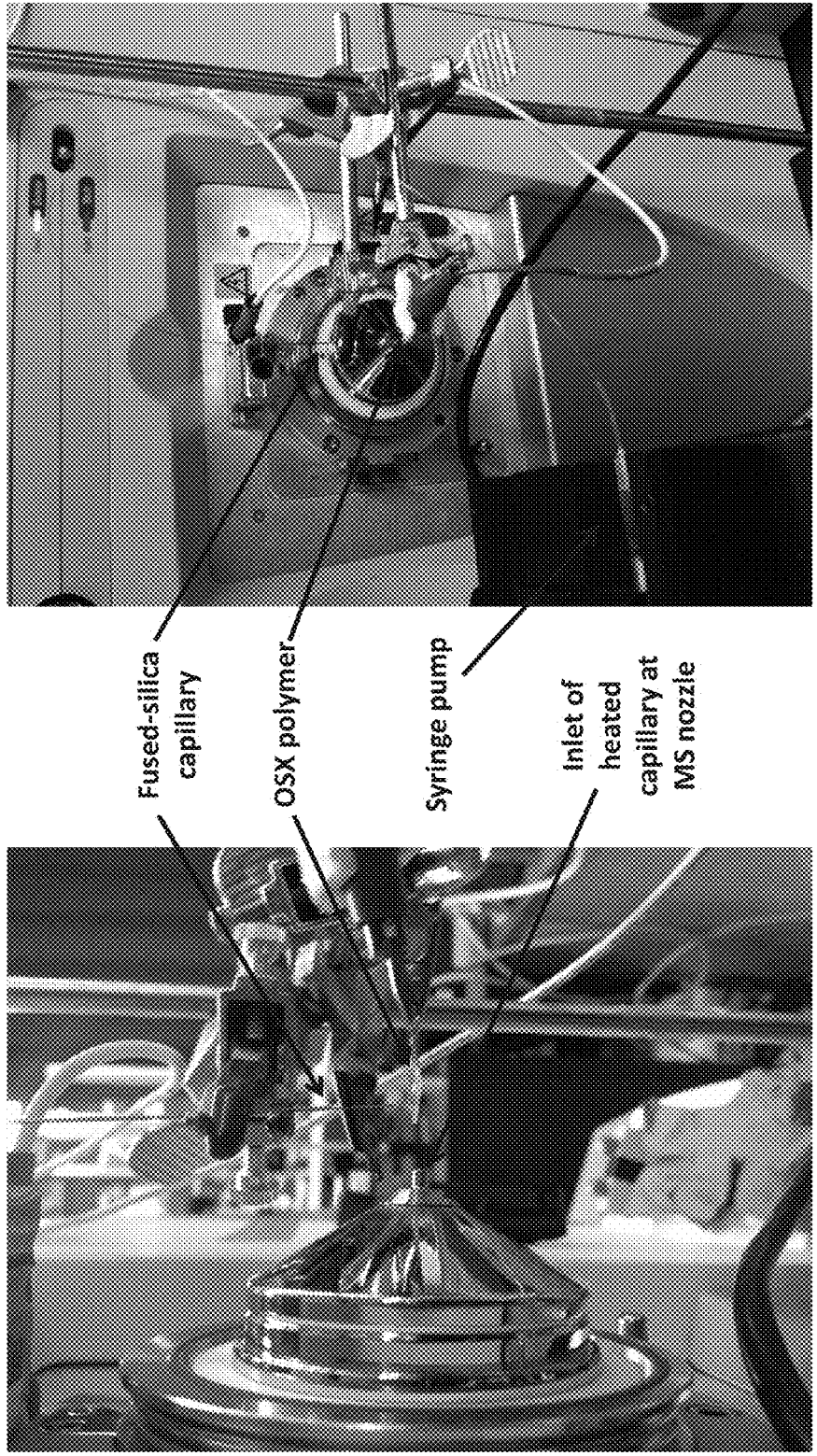
FIG. 16 illustrates an experimental set up of a system having a mass spectrometer, a metal organic polymer matrix and a source of solvent according to certain embodiments.
Figure 17:
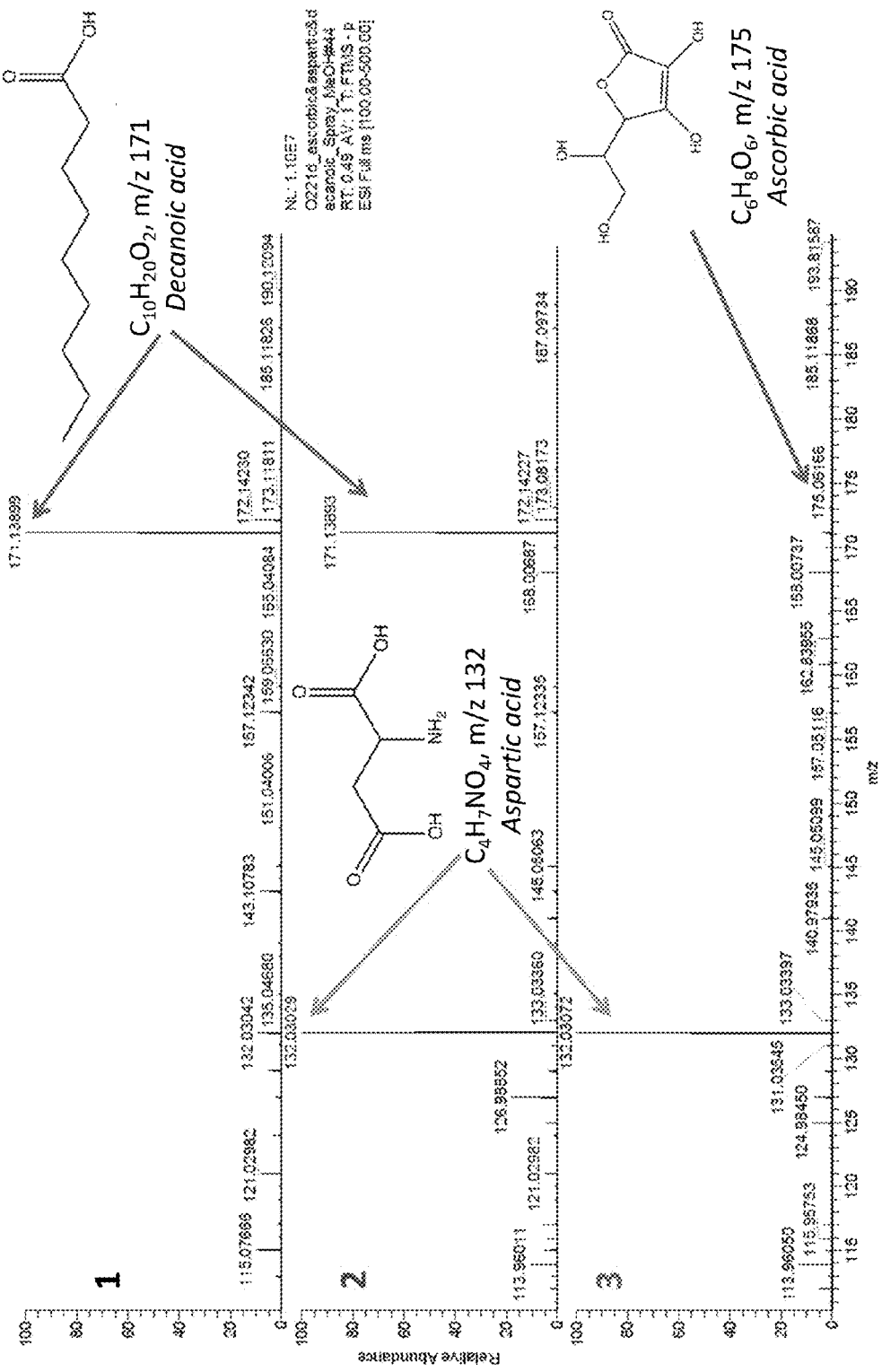
FIG. 17 shows an example of spectra demonstrating analysis of decanoic acid, aspartic acid and ascorbic acid taken employing an organosiloxane polymer matrix according to certain embodiments.

The OSX material was prepared and used as described in Example 7. The half-moon shape was cut using conventional scissors from a round piece of OSX polymer. FIG. 13 illustrates the results of spray ionization using this material over a period of 4.2 min. The top spectrum in the figure shows the total ion count during the 4.2 min period and the bottom spectrum is the mass spectrum.

Example 11

Polymerization. The reaction stock solution was prepared by adding 350 μL of MTMS and 225 μL DMDMS to 500 μL of 4.5 mM aqueous CTAC and 200 μL of 0.12 N HCl. This solution was vigorously stirred at room temperature for approximately 30 minutes to afford a transparent, colorless solution. Volumes of 200 μL, 400 μL and 600 μL of the resulting reaction solution was used to fill the wells of a 24-well polystyrene multiculture plate (Beckton-Dickinson) and placed into an 80° C. oven for approximately 2 days. The resulting OSX material was transparent, colorless, and flexible.

Figure 18:
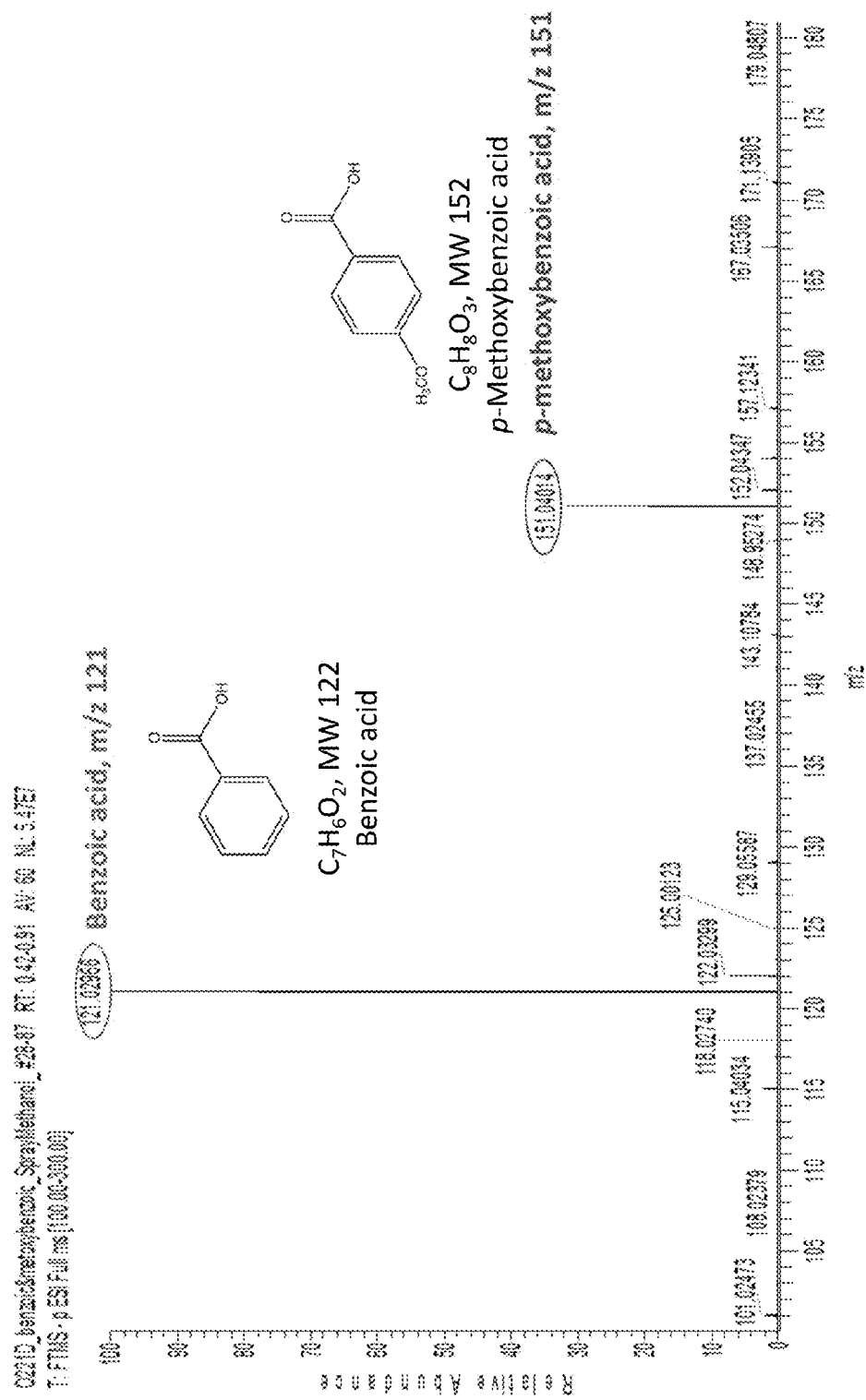
FIG. 18 shows an example of spectra demonstrating analysis of benzoic acid and p-methoxybenzoic acid taken employing an organosiloxane polymer matrix according to certain embodiments.

Instrumentation. A Thermo Scientific LTQ-Orbitrap XL mass spectrometer was used to carry out the mass spectrometry (MS) experiments. A DC voltage of 4 kV was applied to the organosiloxane (OSX) material wetted with 10 μL methanol. The vertex/tip of the OSX material was aligned directly in front of the heated capillary of the MS nozzle. FIG. 14 illustrates the spray ionization stability over a period of 2.6 min. The top spectrum in this figure is a recording of the total ion count during this run period. CTAC (m/z 284), which is not consumed in the reaction, was not removed from the OSX polymer and therefore is observed as shown in the bottom m/z spectrum, showing an m/z peak at 284 for CTAC (minus Cl).

Example 12

The OSX polymer was prepared and used as described in Example 11. FIG. 15 shows the spray ionization results using a circular OSX polymer, i.e., no vertices. A voltage of 4 kV was applied and 10 μL of methanol was used as the spray solvent. No signal was detected over a period of approximately 1-min.

Example 13

Table 1 below shows a comparison of the spray ionization performance as a function of OSX polymer shape. Stable spray with methanol as the spray solvent is achieved using an OSX polymer with one vertex. Spray ionization performance is also compared to paper spray ionization under the same conditions using the same LTQ MS instrument.

TABLE 1

| OSX | Shape | Signal | Analyte | vs. Paper |
|---|---|---|---|---|
| PEG-10 (SG0207) | Planar Half circle | Stable; 4 kV, 5 kV | — | Reusable, spray 6x from same polymer |
| PEG-10 (SG0207) | Planar Half circle | Stable; 4 kV | Rhodamine 123 (detected) | Multiple use of single polymer |
| PEG-4000 (SG4000) | Planar Triangle | Stable; 5 kV | — | Reusable |
| PEG-1000 (SG1000) | Planar Triangle | Stable; 5 kV | — | Reusable |
| PEG-10 (SG0421B) | Planar Triangle | Stable; 4 kV | — | Reusable |
| PEG-10 (SG0421B) | Planar Triangle | Stable; 4 kV | Rhodamine 123 (detected) | n/a |
| PEG-10 (SG0421B) | Planar Triangle | Stable; 4 kV | Saxitoxin (n.d.) + Aconitine (dectected) in $H_2O$ | n/a |
| PEG-10 (SG0421B) | Planar Triangle | Stable; 4 kV | Saxitoxin-fatty acid derivative (n.d.) + Aconitine (detected) in $H_2O$ | Neither compound detected |
| PEG-10 (SG0421B) | Planar Half Circle | Stable; 4 kV | — | n/a |
| CTAB (SG0422A) | Planar Triangle | Stable; 4 kV | — (CTAB detected) | n/a |
| CTAB (SG0422A) | Planar Circle | None | — | n/a |

Example 14

Polymerization. The reaction stock solution was prepared by adding 500 μL of MTMS and 225 μL DMDMS to 275 μL of 4.5 mM aqueous CTAC and 325 μL of 0.12 N HCl. This solution was vigorously stirred at room temperature for approximately 60 minutes to afford a transparent, colorless solution. Volumes of 200 μL, 400 μL and 600 μL of the resulting reaction solution was used to fill the wells of a 12-well polystyrene multiculture plate (Beckton-Dickinson) and placed into an 80° C. oven for approximately 7 hours. The resulting OSX material was transparent, colorless, and flexible.

Instrumentation. A Thermo Scientific LTQ-Orbitrap XL mass spectrometer was used to carry out the mass spectrometry (MS) experiments. A DC voltage of 4 kV was applied to the triangular-shaped organosiloxane (OSX) material wetted with 10 μL methanol. Ascorbic acid and aspartic acid were each prepared as 1 mg/mL stock solutions. A stock solution of 1 mg/mL of decanoic acid was prepared in acetonitrile. The final test mixture was prepared by adding 1:1:1 (v/v/v) of stock solutions of ascorbic acid, aspartic acid, and decanoic acid. The vertex/tip of the OSX material was aligned directly in front of the heated capillary of the MS nozzle. The test mixture was introduced to the OSX polymer using a 75-μm inner diameter fused-silica capillary filled with a 10-cm monolithic sol-gel chromatographic material. Liquid flow was achieved by applying pressure with a syringe pump that delivered flow rates in the range of 5 to 20 μL/min. FIG. 16 illustrates this set-up, using a fused-silica capillary oriented a few millimeters above the OSX polymer. FIG. 17 shows the m/z spectrum of each of these test analytes obtained with ambient spray ionization at different times during the spray—decanoic acid with m/z 171, aspartic acid with m/z 132 and ascorbic acid with m/z 175.

Example 15

The OSX material was prepared and used as described in Example 14. The triangle shape was cut using conventional scissors from a round piece of OSX polymer. A voltage of 4 kV was applied and 10 μL of methanol was used to wet the OSX polymer. Stock solutions of were prepared for benzoic acid and p-methoxybenzoic acid at concentrations of 1 mg/mL each. The test mixture was prepared by mixing 1:1 (v/v) of each of the two stock solutions. The test mixture was introduced to the OSX polymer using a 75-μm inner diameter fused-silica capillary filled with a 10-cm monolithic sol-gel chromatographic material. Liquid flow was achieved by applying pressure with a syringe pump that delivered flow rates in the range of 5 to 20 μL/min. FIG. 18 shows the m/z spectrum with the benzoic acid m/z peak at 121 and the p-methoxybenzoic acid m/z peak at 151.

Example 16

Figure 19:
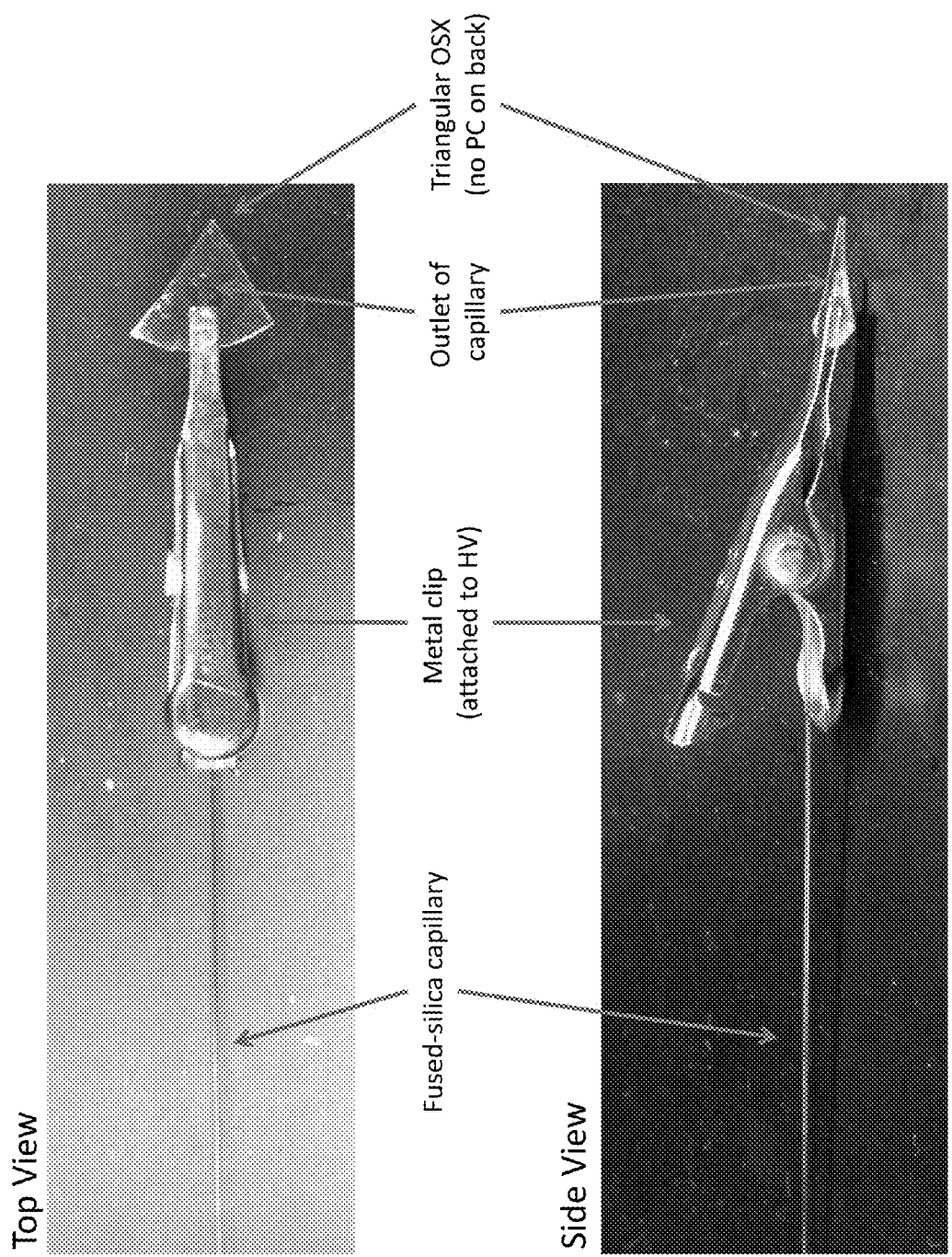
FIG. 19 shows an example of a sample experimental setup for delivering solvent and ionizing an analyte composition according to certain embodiments.
Figure 20:
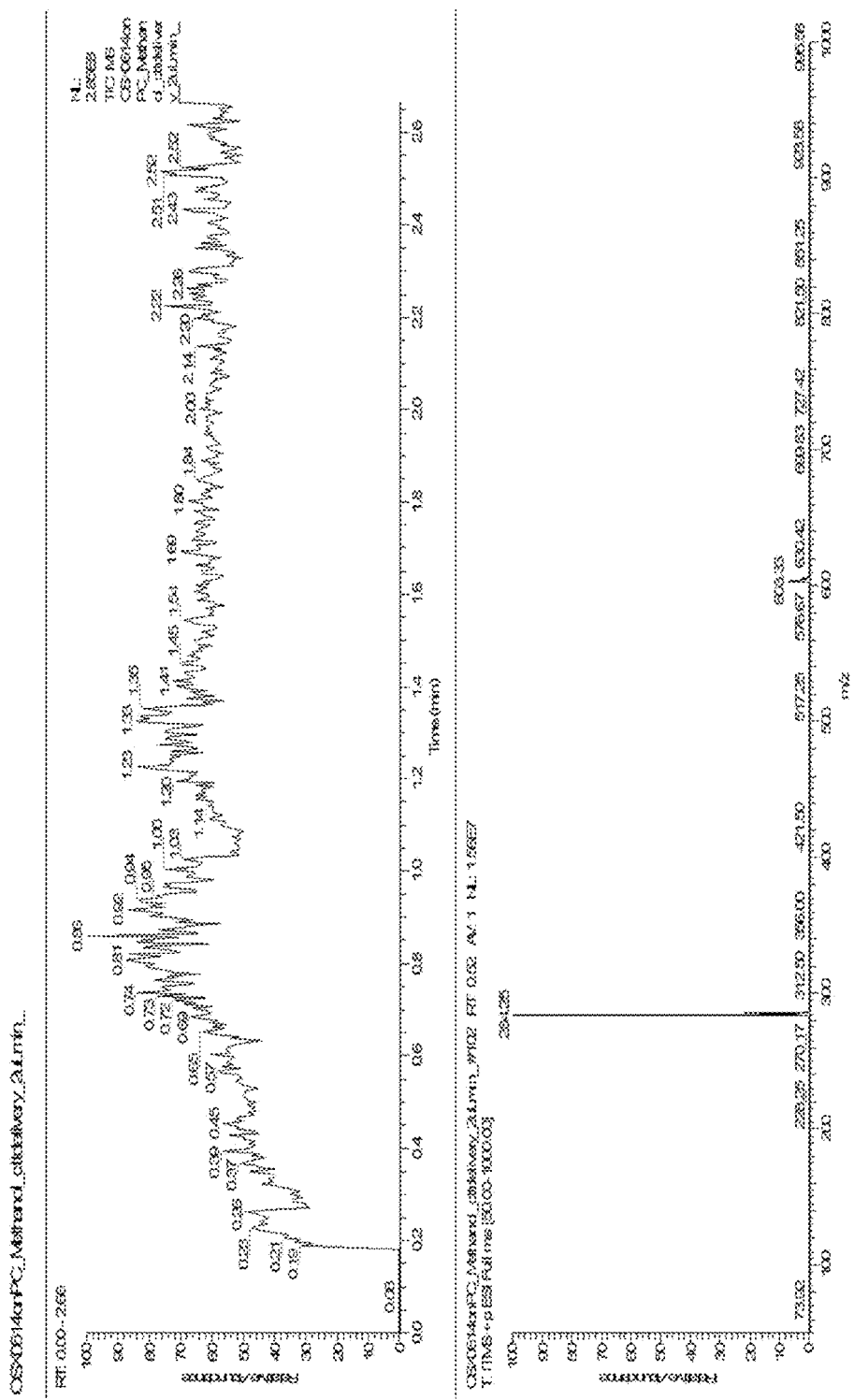
FIG. 20 shows an example of spectra demonstrating signal stability acquired with continuous solvent delivery according to certain embodiments.
Figure 21:
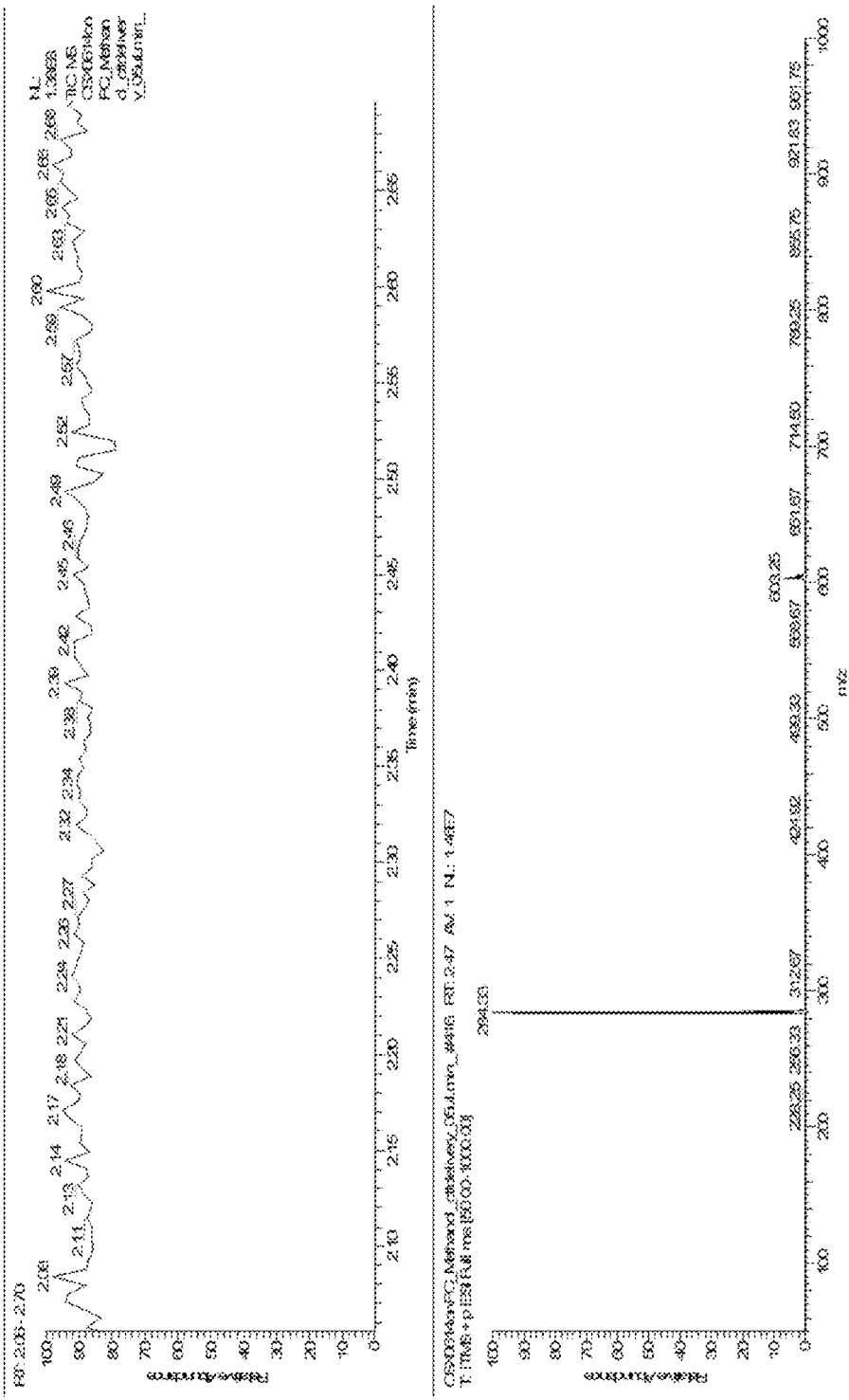
FIG. 21 shows another example of spectra demonstrating signal stability acquired with continuous solvent delivery according to certain embodiments.

Continuous Delivery of Solvent to OSX Supported on a Polycarbonate Plastic. An OSX polymer was placed atop a polycarbonate (PC) coverslip (used in microscopy). Together, both materials were cut into a triangular shape using conventional scissors. A continuous flow of methanol was achieved by placing a 75-micron inner diameter (i.d.) fused-silica capillary parallel to the base of the OSX—PC and just under the metal clip as shown in FIG. 19. Using a programmable solvent pump, methanol was delivered to the OSX at flow rates in the range of 0.5 to 5 microliters/min FIG. 20 demonstrates the usefulness of this solvent delivery approach at a flow rate of 2 microliters/min. No signal is recorded when solvent is not flowing and therefore the OSX is not wet. FIG. 21 further demonstrates the stability of signal during continuous flow of methanol at a flow rate of 1 microliter/min Example 17

Figure 22:
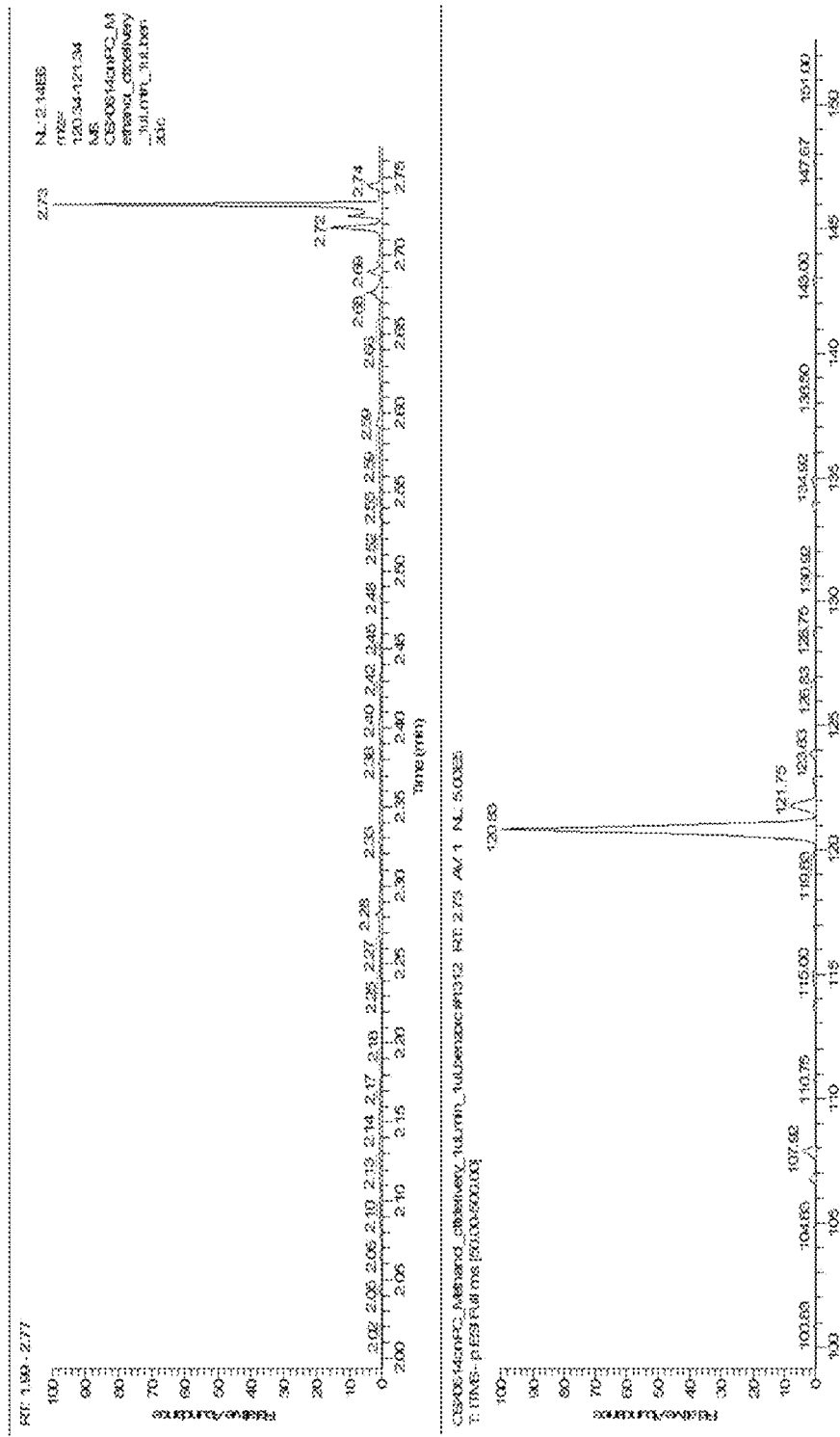
FIG. 22 shows an example of spectra demonstrating analysis of benzoic acid employing an organosiloxane polymer matrix with continuous solvent delivery according to certain embodiments.

Using the same OSX-PC design as in Example 16 and the same continuous flow setup, 2 microliters of benzoic acid (1 mg/mL in acetonitrile) was used to test sample introduction and detection during a continuous flow of methanol. FIG. 22 shows that the highest abundance of benzoic acid was detect approximately 1.5 min after the sample was introduced onto the OSX surface (starting point near the base just in front of the metal clip junction with the OSX) with methanol being delivered constantly at a flow rate of 1 microliter/min Example 18

A variety of OSX polymers were created by varying a variety of parameters as described in general terms below:
Variations in Si:water ratio
Variations in MTMS:DMDMS:water:acid catalyst ratio
Variations in MTMS:DMDMS:water:acid catalyst:urea ratios
Additions of surfactants, such as CTAB, to suppress phase separation in the reaction
Variations in the reaction temperature from 0° C. to 85° C.
Variations in catalysis using either acid or a 2-step acid/base catalyst system
Additions of pore templates such as polyethylene glycol (PEG) with molecular weights, ranging from 1,000 to 10,000
Different types of molds made from plasma-oxidized polystyrene to polycarbonate to polydimethylsiloxane (PDMS) to polypropylene (not a reaction parameter)
Variations in the stirring time (i.e., hydrolysis reaction)
Variations in the gelation and aging times (i.e., condensation reaction)

Example 19

A thin flexible, flexible and macroporous organosiloxane polymer was prepared using a reaction mixture of methyltrimethoxysilane, dilute hydrochloric acid, water, and PEG with a molecular weight of 10 kDa. The reaction mixture was allowed to hydrolyze and partially condense at room temperature prior to pouring into unreactive plastic circular molds with diameters ranging from 0.8 cm to 1.2 cm. The reaction solution in the molds were completely cured at temperatures between 37° C. and 80° C. and with curing times ranging between 18 hours and 2 weeks at a single temperature ranging between 37° C. and 80° C. to yield a macroporous organosiloxane polymer matrix. The macroporous organosiloxane polymer matrix had a thickness of 1 mm and were optically transparent, flexible and were easily cut with scissors into various shapes having at least a single straight edge and one vertex.

Fabrication of Osx-Trypsin on Glass Slides

Materials and Chemicals. Methyltrimethoxysilane (MTMS), dimethyldimethoxysilane
(DMDMS), other silanes, Trypsin (TPCK-treated, from bovine pancreas), Melittin (from honey bee venom), Neurotensin, and Insulin Chain B (oxidized, bovine pancreas) were purchased from Sigma-Aldrich (St. Louis, Mo.) and used without further purification. Acetic acid, acetonitrile, methanol, 1×PBS (pH 7.4), and molecular-grade distilled water were used without further purification. Glass slides coated with PTFE were purchased from Electron Microscopy Sciences (Hatfield, Pa.); no pretreatment or precleaning was necessary.

Figure 23:
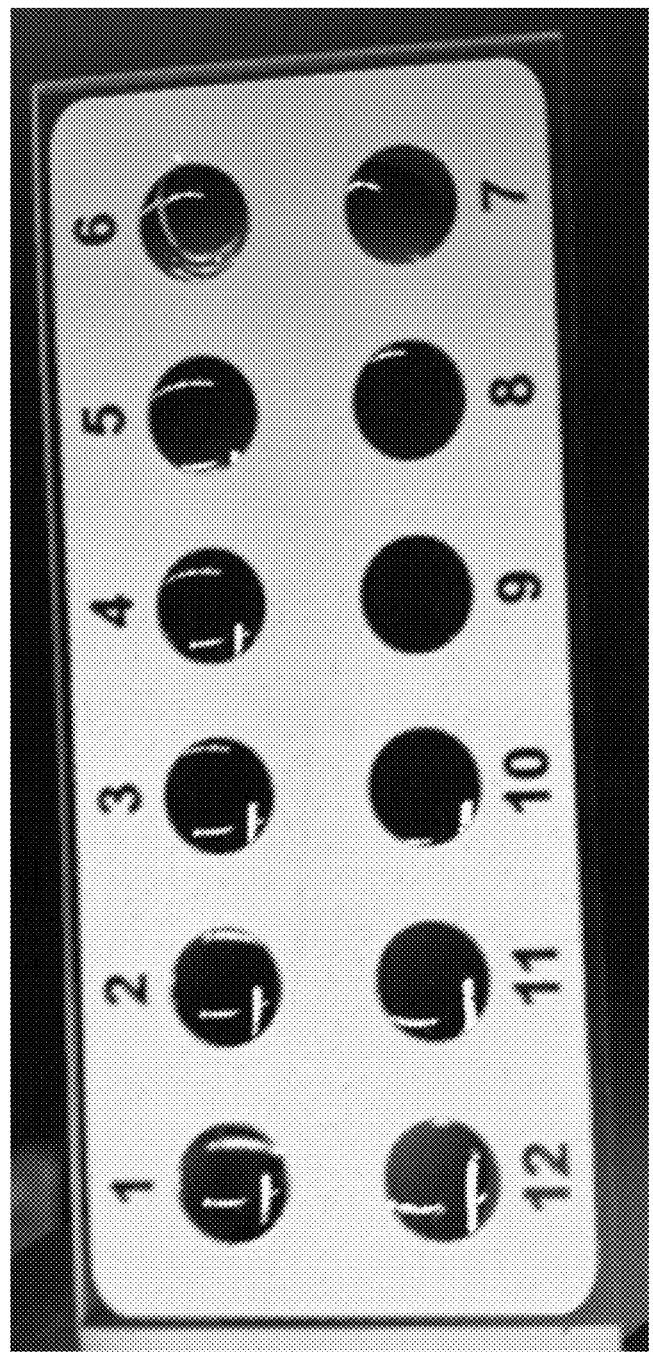
FIG. 23 shows an example of a 12-well PTFE-coated glass slide with organosilioxane polymer in each of the 12 wells according to certain embodiments.

Organosiloxane Polymerization Procedure. The reaction stock solution was prepared by adding 500 μL of MTMS and 225 μL DMDMS to 600 μL of 5 mM acetic acid. This solution was vigorously stirred in a closed glass vial at room temperature for approximately 30 minutes to afford a transparent, colorless solution. A volume of 3 to 10 μL of the resulting reaction solution was deposited to each of well, depending on the diameter of the well, on a PTFE-coated glass slide. The glass slides were placed into a Petri dish with lid, the placed into a 65° C. oven between 12 and 72 hours. The resulting organosiloxane polymer is transparent and colorless (FIG. 23). Any unreacted starting materials and byproducts formed during the polymerization was removed by immersing the entire glass slide into a glass staining jar filled with acetonitrile for 2 to 12 hours.

Trypsin Derivatization of Organosiloxane Polymer on Glass Slide. The glass slide was dried either by letting it sit in ambient air for a few minutes or gently blowing air over the surface to remove all of the acetonitrile prior to derivatization of the surface with an aldehyde-containing reagent. A 1:1 (v/v) of an aldehyde-containing silane and acetonitrile was used to modify the organosiloxane polymer surface prior to trypsin attachment. Approximately 4 to 10 μL of aldehyde solution was deposited onto each polymer, depending on the diameter of the polymers on the glass slides. The reaction was allowed to proceed for 60 min. The glass slides were then immersed into a staining jar filled with acetonitrile to remove any unreacted starting materials and byproducts. This derivatization procedure was repeated one more time for a total derivatization time of 2 hours. As a final step, the glass slides were immersed in acetonitrile for several hours.

Figure 24:
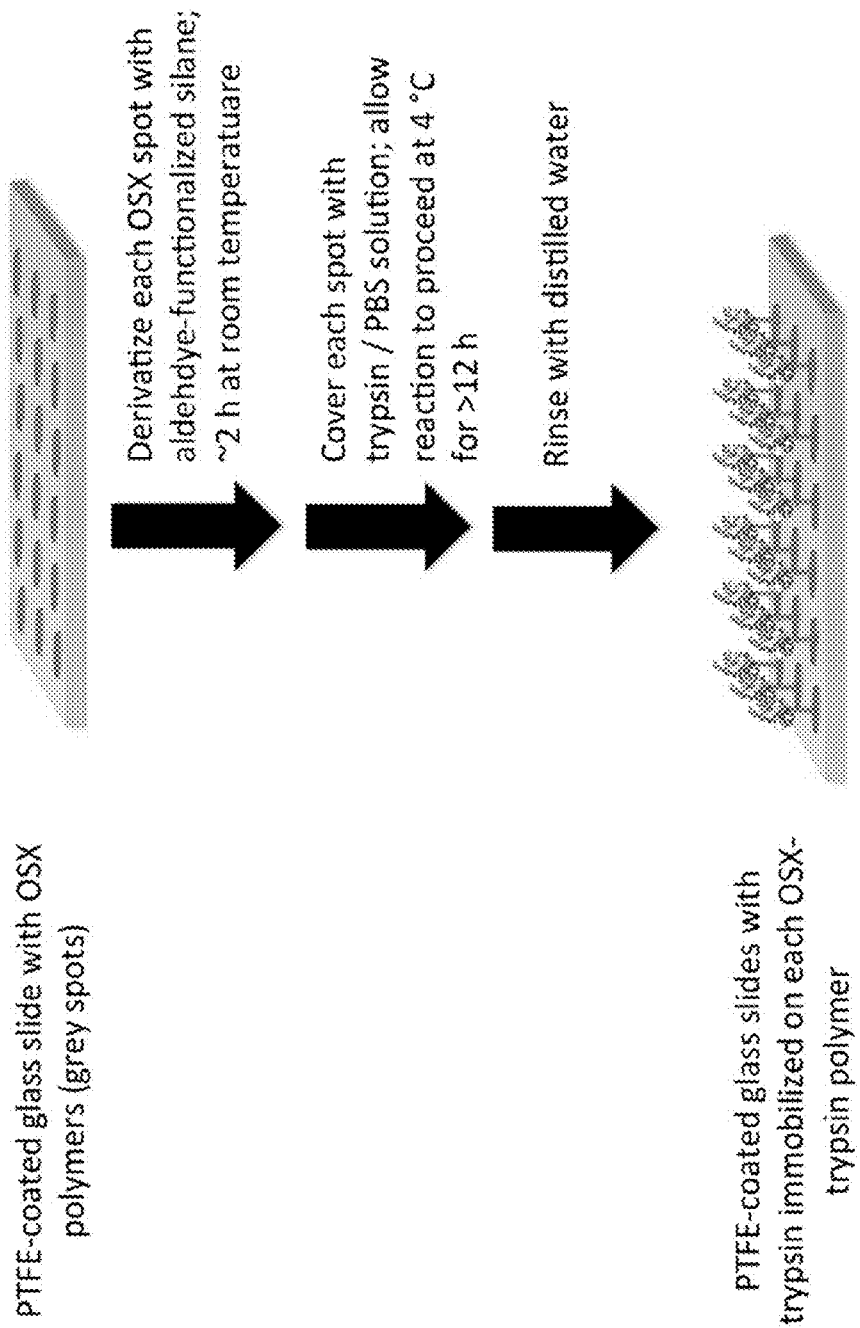
FIG. 24 shows an example of work-flow for immobilizing an enzyme on a macroporous metal organic polymer matrix surface according to certain embodiments.

Prior to trypsin attachment, the glass slides were completely immersed in distilled water for several hours to replace and to remove acetonitrile from the OSX polymer. The OSX polymers were dried by gently blowing air over the surface. A trypsin derivatizing solution was prepared by mixing 10 mg Trypsin in 1 mL distilled water. Approximately 5 to 10 μL of the Trypsin solution was deposited onto each of the OSX polymers on glass slides, depending on the diameter of the OSX polymer. The glass slides were placed in a Petri dish with lid, then placed into a 4° C. cold room for approximately 19 hours to allow the reaction to occur while minimizing Trypsin autolysis. Any remaining Trypsin and PBS buffer was removed by immersing the OSX-Trypsin glass slides in distilled water for several hours. FIG. 24 is a cartoon depiction of work-flow in trypsin immobilization on OSX polymers. When not in use, the OSX-Trypsin glass slides were stored in distilled water in a cold room or in dry state at room temperature.

Figure 25:
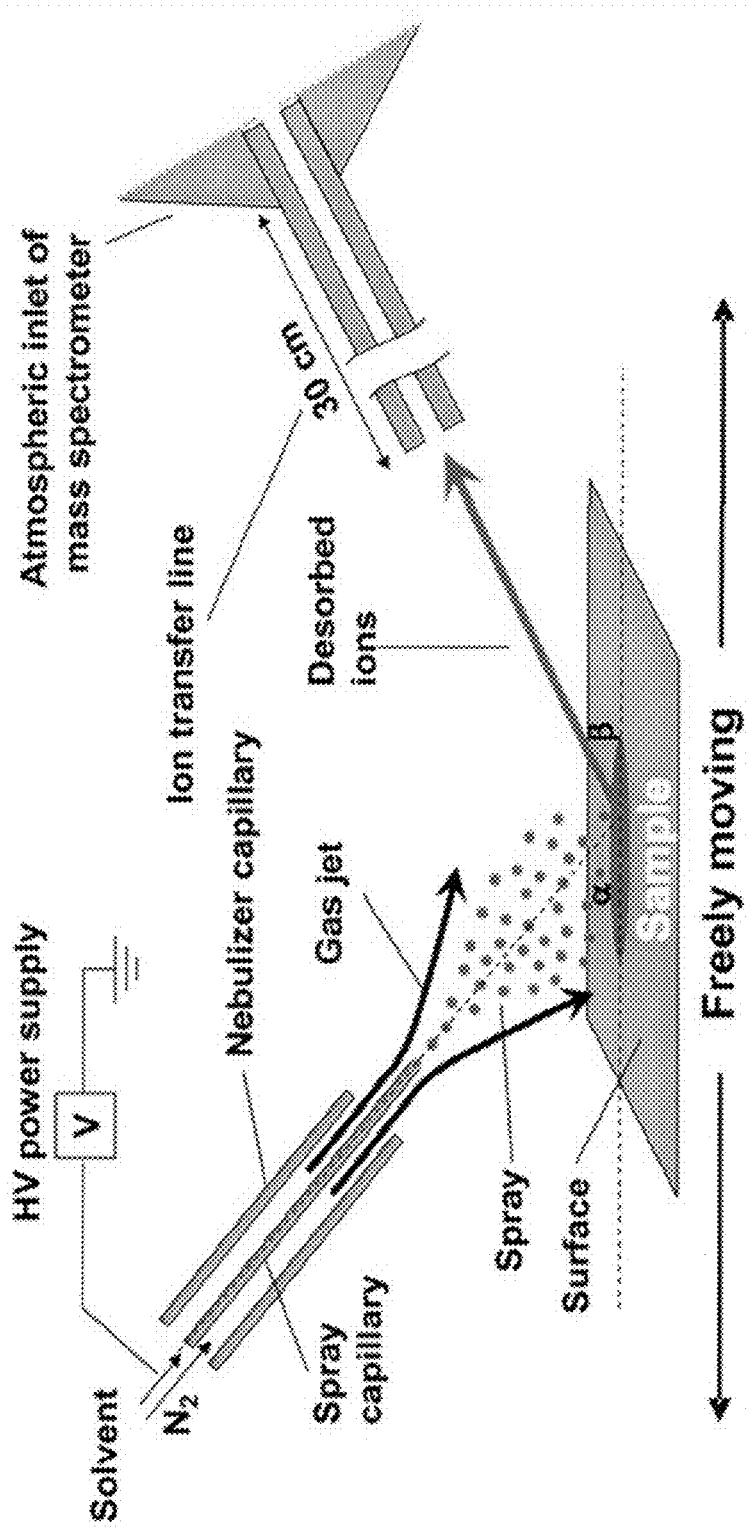
FIG. 25 shows an illustration of surface ionization and analysis by desorption electrospray ionization-mass spectrometry according to certain embodiments.

Substrate Digestion and Analysis by Desorption Electrospray Ionization (DESI) Mass Spectrometry Instrumentation. An Orbitrap LTQ XL mass spectrometer (Thermo Fisher) in positive-ion mode and with a freely moving stage was used in the analysis of Trypsin digestion of Neurotensin, Insulin Chain B and Melittin. FIG. 25 shows a schematic of DESI, a surface-based technique, droplet pick-up and micro-extraction, and the electrospray ionization (ESI) mechanism. The spray solvent was 1:1 methanol:water.

Figure 26:
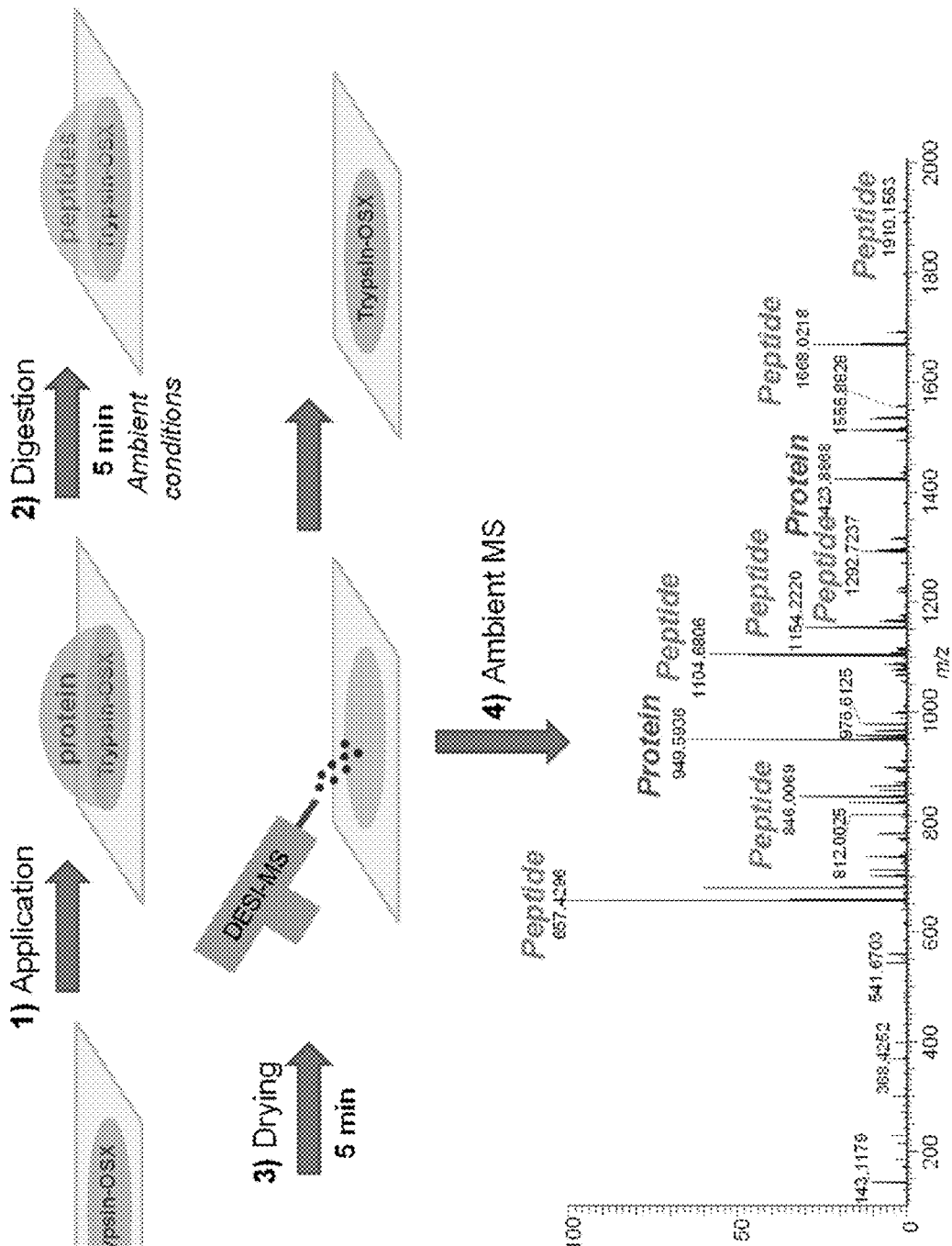
FIG. 26 shows an example of work-flow for analyzing a composition with desorption electrospray ionization-mass spectrometry applied to an enzyme-modified macroporous metal organic polymer matrix surface according to certain embodiments.

Digestion Protocol. Stock solutions of the protein substrates were prepared as 1 mg/mL in varying concentrations of methanol in distilled water. From the stock solutions, diluted samples were prepared. Volumes of 1 to 3 µL of substrate solution were deposited onto each OSX-Trypsin polymer and allowed to react for 5 to 8 minutes at room temperature in open air. This was followed by drying in a dessicator with house vacuum for 5 to 8 minutes. Used OSX-Trypsin polymer was cleaned by rinsing with distilled water. FIG. 26 is a schematic illustration of a digestion protocol according to certain embodiments as well as analysis by DESI-MS. First, a small volume (~3 µL) of protein solution is deposited onto the trypsin-OSX material (step 1). Tryptic digestion of the protein into small peptides occurs in ambient conditions, for 5 minutes or longer (step 2). The material is dried for an additional 5 minutes (step 3) and directly subjected to ambient mass spectrometry analysis (step 4), such as desorption electrospray ionization mass spectrometry (DESI-MS). The Trypsin-OSX material can be cleaned and reused for other experiments (step 5). The rich mass spectrum obtained shows peaks corresponding to specific trypic peptides from the protein, as well as peaks corresponding to different charge states of the original protein. Trypsin or trypic peptides of trypsin are not observed in the mass spectrum.

Analysis

Example 20

Figure 27:
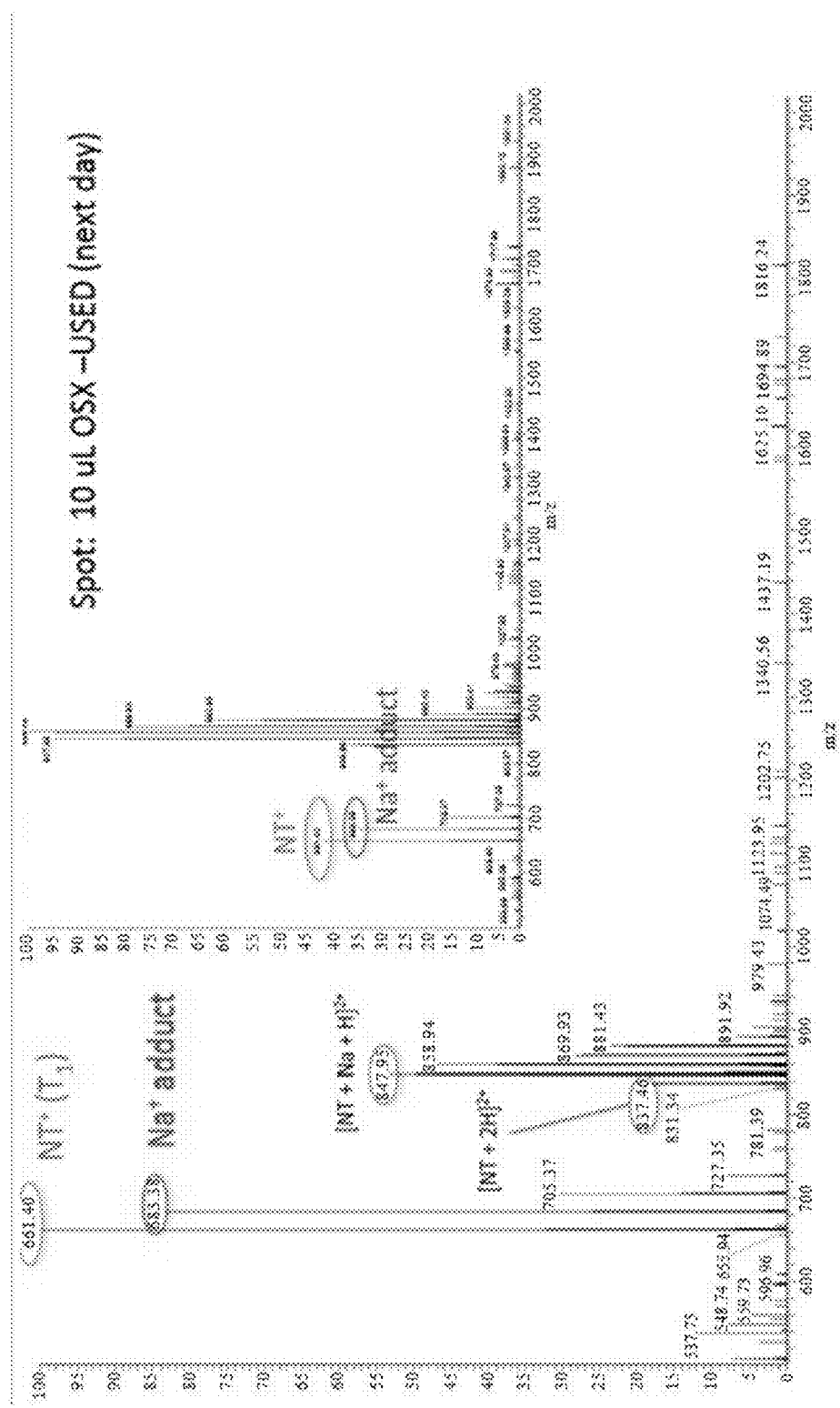
FIG. 27 shows an example of spectra demonstrating analysis of Neurotensin digested by surface-bound trypsin employing an enzyme-modified macroporous metal organic polymer matrix surface and desorption electrospray ionization-mass spectrometry according to certain embodiments.

Tryptic Digest of Neurotensin. Neurotensin is a 13-amino acid neuropeptide with a molecular mass of 1672.92 that was first used to evaluate the performance of the OSX-Trypsin polymers with DESI-MS. There are two main tryptic digest fragments: ELYENKPR ($T_1$) with an m/z of 1048.54 ($MH^+$) and RPYIL ($T_2$) with an m/z of 661.40 ($MH^+$). FIG. 27 is a positive-ion mode mass spectrum of a tryptic digest of 1 mg/mL Neurotensin in 50% aqueous methanol. A volume of 10 µL was deposited onto an OSX-Trypsin polymer and allowed to react for 5 min at room temperature. The spray solvent was methanol. FIG. 27 illustrates the digestion of Neurotensin on an OSX-Trypsin polymer within 5 min at room temperature. Fragment $T_1$ and its sodium ($Na^+$) adduct, along with undigested Neurotensin, are observed in the MS spectrum. The inset of FIG. 27 depicts the same OSX-Trypsin polymer used for the digestion of Neurotensin approximately 24 hours later.

Example 21

Figure 28:
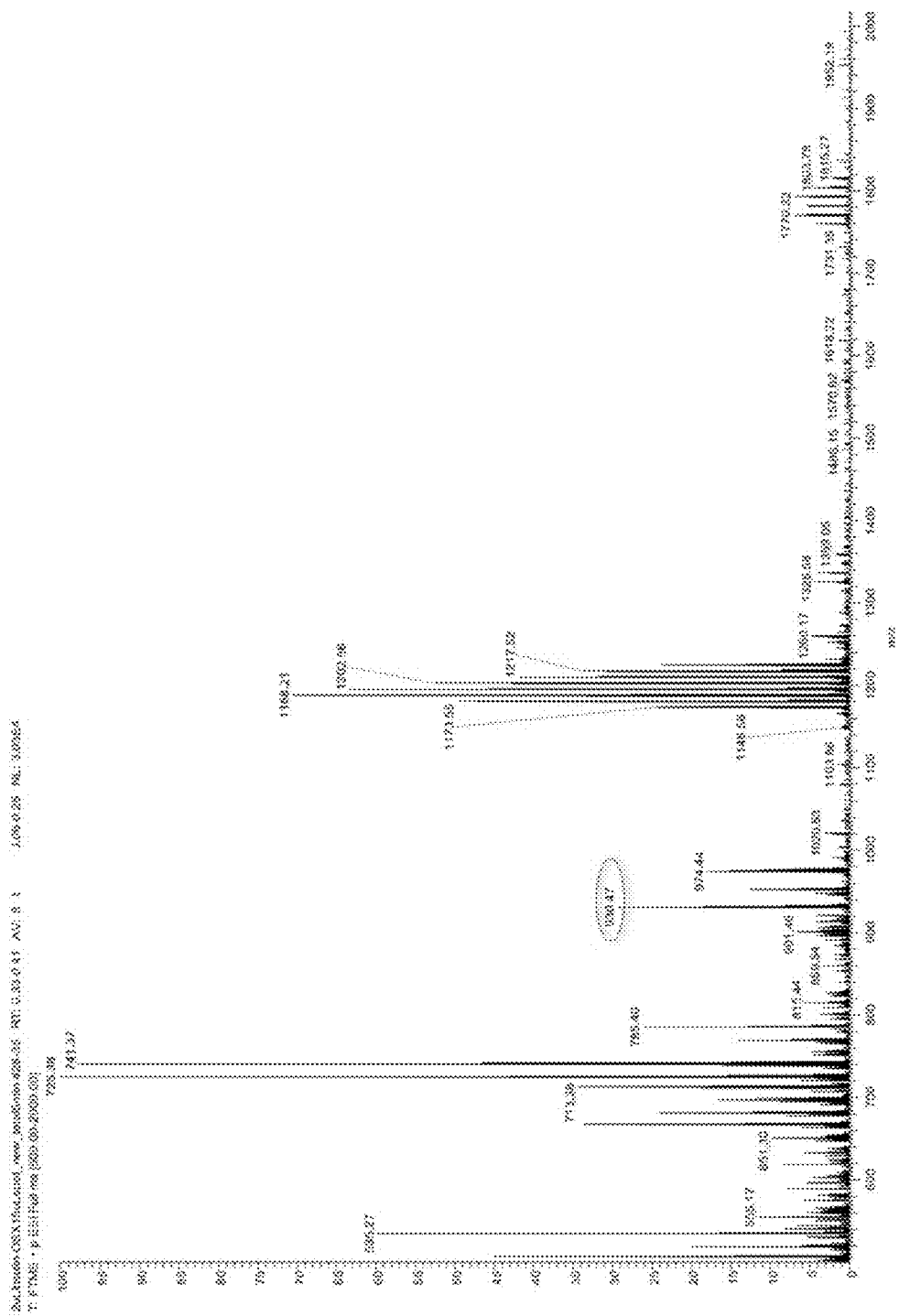
FIG. 28 shows an example of spectra demonstrating analysis of Insulin Chain B digested by surface-bound trypsin employing an enzyme-modified macroporous metal organic polymer matrix surface and desorption electrospray ionization-mass spectrometry according to certain embodiments.

Tryptic Digest of Insulin Chain B Oxidized. Insulin Chain B is a 30-amino acid polypeptide with a molecular mass of 3495.89. There are three main tryptic digest fragments: GFFYTPK ($T_1$) with an m/z of 860.00, GFFYTPKA ($T_2$) with an m/z of 930.08, and FVNQHLCG-SHLVEALYLVCGER ($T_3$) with an m/z of 2585.90. FIG. 28 is a positive-ion mode DESI mass spectrum of a tryptic digest of 1 mg/mL Insulin Chain B oxidized in 50% aqueous methanol. A volume of 10 µL was deposited onto an OSX-Trypsin polymer and allowed to react for 5 min at room temperature. The spray solvent was methanol. FIG. 28 shows the digest fragment $T_2$.

Example 22

Figure 29:
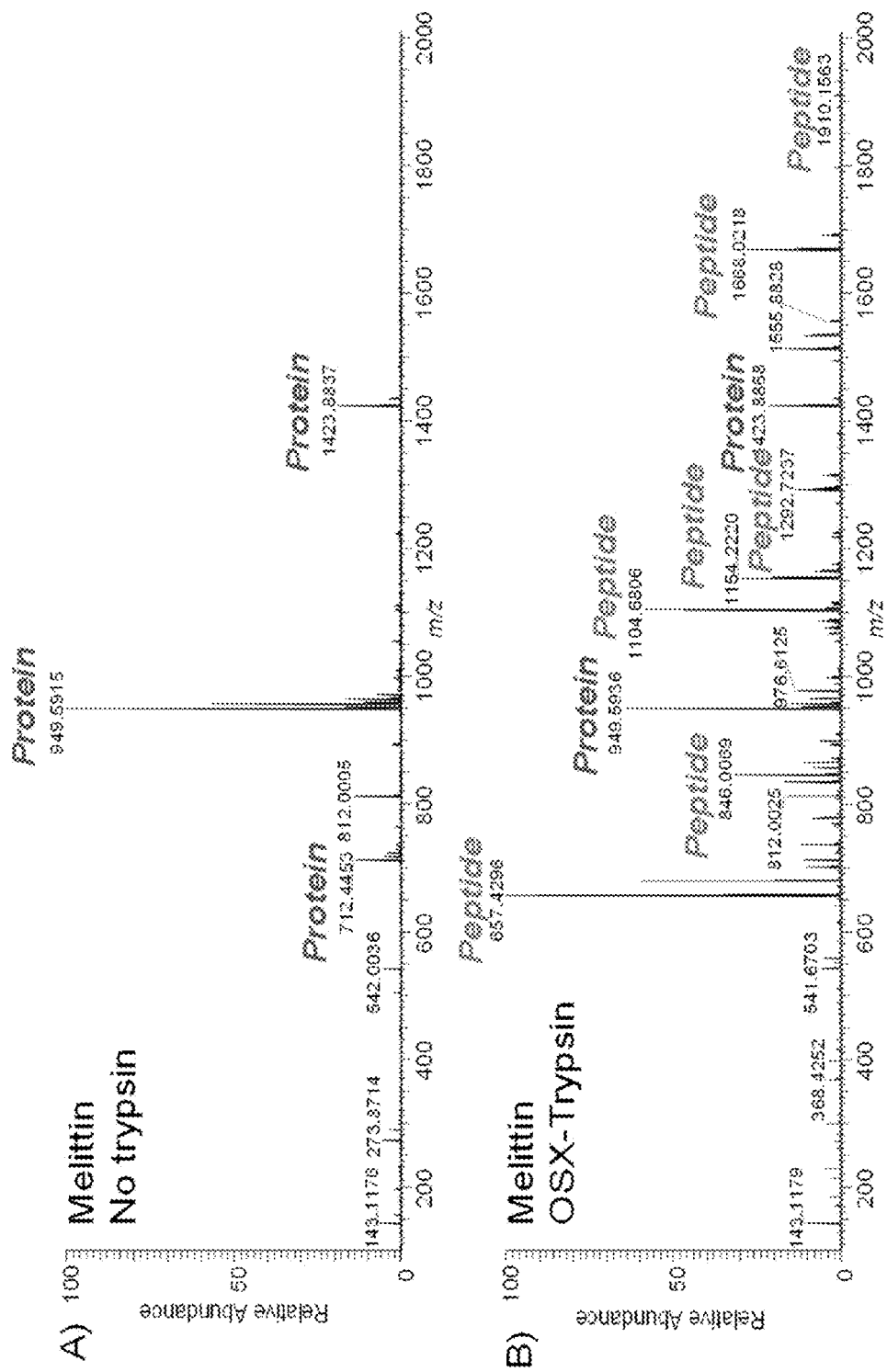
FIG. 29a shows an example of spectra demonstrating analysis by desorption electrospray ionization-mass spectrometry of Melittin employing a macroporous metal organic polymer matrix without surface-bound trypsin.
FIG. 29b shows an example of spectra demonstrating analysis of Mellitin digested by surface-bound trypsin employing an enzyme-modified macroporous metal organic polymer matrix surface and desorption electrospray ionization-mass spectrometry according to certain embodiments.

Tryptic Digest of Melittin. Melittin is a 26-amino acid polypeptide with a molecular mass of 2846.46. FIG. 29*a* is a positive-ion mode DESI mass spectrum obtained from a 3 µL of melittin solution (0.1 mg/mL in 40% methanol) deposited onto OSX material that was not derivatized with trypsin. FIG. 29*b* is a positive-ion mode DESI mass spectrum obtained from 3 µL of melittin solution (0.1 mg/mL in 40% methanol) deposited onto Trypsin-OSX material after 5 minutes of digestion and 5 minutes of drying time. FIGS. 29*a-b* show no digestion in the absence of trypsin on an OSX polymer (FIG. 29*a*) and digestion of 0.1 mg/mL Melittin in 40% aqueous methanol on an OSX-Trypsin polymer (FIG. 29*b*). All 6 digest fragments are observed after a 5-min digestion at room temperature followed by 5 min of drying time under house vacuum. Some undigested Melittin is also observed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   producing and expelling analyte ions from a macroporous metal organic polymer matrix comprising an analyte composition, wherein the macroporous metal organic polymer matrix comprises a polymer prepared from precursors of the formula $(RO)_y M_x (R_1)_z$, wherein:
x is an integer from 1 to 4;
y is an integer from 0 to 4;
z is an integer from 0 to 4;
wherein at least one of y or z is 1 or greater;
O is oxygen;
M is aluminum, barium, antimony, calcium, chromium, copper, erbium, germanium, iron, lead, lithium, phosphorus, potassium, silicon, tantalum, tin, titanium, vanadium, zinc or zirconium;
R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
$R_1$ is individually hydrogen, alkyl, substituted alkyl, aryl substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
analyzing the analyte ions by mass spectrometry.

2. The method according to claim 1, wherein the method comprises desorption ionization of the analyte composition from the macroporous metal organic polymer matrix.

3. The method according to claim 2, wherein the macroporous metal organic polymer matrix comprises one or more enzymes covalently bonded to the surface of the macroporous metal organic polymer matrix.

4. The method according to claim 3, wherein the method further comprises:
contacting the surface of the macroporous metal organic polymer matrix with an analyte composition comprising a biological macromolecule selected from the group consisting of proteins, enzymes, oligopeptides and antibodies; and
maintaining the analyte composition in contact with the surface of the macroporous metal organic polymer matrix in a manner sufficient to enzymatically cleave the biological macromolecule into peptide fragments.

5. The method according to claim 1, wherein the method comprises applying a voltage to the analyte comprising macroporous metal organic polymer matrix sufficient to produce and expel analyte ions from one or more vertices of the macroporous metal organic polymer matrix.

6. The method according to claim 5, wherein the method further comprises separating components of the analyte composition on the analyte comprising macroporous metal organic matrix.

7. The method according to claim 1, wherein the macroporous metal organic polymer matrix comprises an organosiloxane polymer.

8. A mass spectrometry emitter comprising a macroporous metal organic polymer matrix configured for expelling analyte ions from an analyte composition, wherein the macroporous metal organic polymer is prepared from metal alkoxide precursors of the formula:

$(RO)_y M_x (R_1)_z$, wherein
x is an integer from 1 to 4;
y is an integer from 0 to 4;
z is an integer from 0 to 4;
wherein at least one of y or z is 1 or greater;
O is oxygen;
M is aluminum, barium, antimony, calcium, chromium, copper, erbium, germanium, iron, lead, lithium, phosphorus, potassium, silicon, tantalum, tin, titanium, vanadium, zinc, zirconium or combinations thereof;
R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and
$R_1$ is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl.

9. The mass spectrometry emitter according to claim 8, wherein the macroporous metal organic polymer matrix comprises an organosiloxane polymer.

10. The mass spectrometry emitter according to claim 8, wherein the macroporous metal organic polymer matrix comprises one or more enzymes covalently bonded at or near the surface of the macroporous metal organic polymer matrix.

11. The mass spectrometry emitter according to claim 10, wherein the enzymes are covalently bonded at or near the surface of the macroporous metal organic polymer matrix in an array configuration.

12. The mass spectrometry emitter according to claim 8, wherein the macroporous metal organic polymer matrix has pore sizes of 0.01 μm or greater.

13. The mass spectrometry emitter according to claim 8, wherein the macroporous metal organic polymer matrix is a chromatographic or electrophoretic matrix.

14. A kit comprising:
a mass spectrometry emitter comprising a macroporous metal organic polymer matrix according to claim 8; and
an applicator for applying an analyte composition to the macroporous metal organic polymer matrix.

15. A system comprising:
a mass spectrometry emitter comprising a macroporous metal organic polymer matrix configured for expelling analyte ions from an analyte composition, wherein the macroporous metal organic polymer is prepared from metal alkoxide precursors of the formula:

$(RO)_y M_x (R_1)_z$, wherein
x is an integer from 1 to 4;
y is an integer from 0 to 4;

z is an integer from 0 to 4;

wherein at least one of y or z is 1 or greater;

O is oxygen;

M is aluminum, barium, antimony, calcium, chromium, copper, erbium, germanium, iron, lead, lithium, phosphorus, potassium, silicon, tantalum, tin, titanium, vanadium, zinc, zirconium or combinations thereof;

R is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and $R_1$ is individually hydrogen, alkyl, substituted alkyl, aryl, substituted aryl, allyl, substituted allyl, vinyl, substituted vinyl, propargyl, substituted propargyl, arylalkyl, substituted arylalkyl, heteroalkyl, substituted heteroalkyl, heteroaryl, substituted heteroaryl, heteroarylalkyl, substituted heteroarylalkyl, acyl, substituted acyl, alkoxycarbonyl, substituted alkoxycarbonyl, vinyl carbonyl, substituted vinyl carbonyl, propargyl carbonyl, substituted propargyl carbonyl, aryl, substituted aryl, arylalkyl or substituted arylalkyl; and a mass analyzer.

16. The system according to claim 15, wherein the macroporous metal organic polymer matrix comprises one or more enzymes covalently bonded at or near the surface of the macroporous metal organic polymer matrix.

17. The system according to claim 15, wherein the system further comprises:

a surface desorption ionization source; or a voltage source for applying a voltage to the macroporous metal organic polymer matrix.

18. The system according to claim 15, wherein the macroporous metal organic polymer matrix has pore sizes of 0.01 µm or greater.

19. The system according to claim 15, wherein the macroporous metal organic polymer matrix is a chromatographic or electrophoretic matrix.

* * * * *